(12) United States Patent
Roberts et al.

(10) Patent No.: US 11,651,535 B2
(45) Date of Patent: May 16, 2023

(54) INTERACTIVE GRAPHICAL USER INTERFACE FOR MONITORING COMPUTER MODELS

(71) Applicant: SAS Institute Inc., Cary, NC (US)

(72) Inventors: Terisa Roberts, Cherrybrook (AU); Vipul Manoj Katiyar, Pune (IN); Amol Kishor Malani, Pune (IN)

(73) Assignee: SAS Institute Inc., Cary, NC (US)

( * ) Notice: Subject to any disclaimer, the term of this patent is extended or adjusted under 35 U.S.C. 154(b) by 0 days.

(21) Appl. No.: 17/860,501

(22) Filed: Jul. 8, 2022

(65) Prior Publication Data

US 2022/0357821 A1 Nov. 10, 2022

Related U.S. Application Data

(63) Continuation-in-part of application No. 17/527,889, filed on Nov. 16, 2021.

(30) Foreign Application Priority Data

Nov. 16, 2020 (IN) .............................. 202011049888
Nov. 16, 2021 (IN) .............................. 202114052608
Jul. 7, 2022 (IN) .............................. 202216039073

(51) Int. Cl.
*G06T 11/20* (2006.01)
*G06F 3/0482* (2013.01)
(Continued)

(52) U.S. Cl.
CPC .......... *G06T 11/206* (2013.01); *G06F 3/0482* (2013.01); *G06F 3/04847* (2013.01); *G06F 11/3495* (2013.01); *G06T 2200/24* (2013.01)

(58) Field of Classification Search
None
See application file for complete search history.

(56) References Cited

U.S. PATENT DOCUMENTS 7,689,572 B2 3/2010 Chu et al.
7,809,729 B2 10/2010 Chu et al.
(Continued)

OTHER PUBLICATIONS

Nair V, Raul A, Khanduja S, Bahirwani V, Shao Q, Sellamanickam S, Keerthi S, Herbert S, Dhulipalla S. Learning a hierarchical monitoring system for detecting and diagnosing service issues. InProceedings of the 21th ACM SIGKDD international conference on knowledge discovery and data mining Aug. 10, 2015 (Year: 2015).*

(Continued)

*Primary Examiner* — Sarah Le
(74) *Attorney, Agent, or Firm* — Coats & Bennett, PLLC

(57) ABSTRACT

A computing system establishes a hierarchy for monitoring model(s). The hierarchy comprises an association between each of multiple measures of a measure level of the hierarchy and intermediate level(s) of the hierarchy. An intermediate level comprises one or more of a measurement category or analysis type. The hierarchy comprises an association between the intermediate level(s) and at least one model. The system monitors the model(s) by generating health measurements. Each of the health measurements corresponds to one of the multiple measures. Each of the health measurements indicates a performance of a monitored model according to a measurement category or analysis type associated in the hierarchy with the respective measure of the multiple measures. The system generates a visualization in a graphical user interface. The visualization comprises a graphical representation of an indication of a health measurement for each of measure(s), and associations in the hierarchy.

30 Claims, 38 Drawing Sheets
(22 of 38 Drawing Sheet(s) Filed in Color)

(51) Int. Cl.
*G06F 11/34* (2006.01)
*G06F 3/04847* (2022.01)

(56) References Cited

U.S. PATENT DOCUMENTS

| | | | |
|---|---|---|---|
| 8,661,065 B2 | 2/2014 | Rausch et al. | |
| 10,380,214 B1 | 8/2019 | Rausch et al. | |
| 10,909,460 B2 | 2/2021 | Rausch et al. | |
| 2014/0274181 A1* | 9/2014 | Lovegren | H04W 72/1205 455/73 |
| 2016/0321574 A1* | 11/2016 | Peterson | G06Q 10/063 |
| 2019/0317952 A1* | 10/2019 | Li | G06F 16/2246 |
| 2022/0067181 A1* | 3/2022 | Carley | G06N 20/00 |

OTHER PUBLICATIONS

Chillibreeze, "Visualizing Hub and Spoke Model in PPT Presentations", posted 2015, https://www.24point0.com/examples-hub-spoke-model/ (Year: 2015).*

The Microsoft 365 Marketing Team, "Breaking down hierarchical data with Treemap and Sunburst charts", posted 2015, https://www.microsoft.com/en-us/microsoft-365/blog/2015/08/11/breaking-down-hierarchical-data-with-treemap-and-sunburst-charts/ (Year: 2015).*

* cited by examiner

Health identifying rules at each Level

Mechanism to enable user to define health identifying rules

Examples of Variables that can be used in expression

| Of Measure Category 2402 | Of Analysis Type 2404 | Of Analysis Object (e.g. a model) 2406 |
|---|---|---|
| | All variables that can be used Measure category | All variables that can be used Measure category, Analysis Type |
| | and following: | and following: |
| PRCTG_OF_MSRS_IN_RED | PRCTG_OF_MSR_CTGRY_IN_RED | PRCTG_OF_AT_IN_RED |
| PRCTG_OF_MSRS_IN_AMBER | PRCTG_OF_MSR_CTGRY_IN_AMBER | PRCTG_OF_AT_IN_AMBER |
| PRCTG_OF_MSRS_IN_GREEN | PRCTG_OF_MSR_CTGRY_IN_GREEN | PRCTG_OF_AT_IN_GREEN |
| COUNT_OF_MSRS_IN_RED | COUNT_OF_MSR_CTGRY_IN_RED | COUNT_OF_AT_IN_RED |
| COUNT_OF_MSRS_IN_AMBER | COUNT_OF_MSR_CTGRY_IN_AMBER | COUNT_OF_AT_IN_AMBER |
| COUNT_OF_MSRS_IN_GREEN | COUNT_OF_MSR_CTGRY_IN_GREEN | COUNT_OF_AT_IN_GREEN |
| HEALTH_OF_MSR_<MSR1> | HEALTH_OF_MSR_CTGRY_<MSR_CTG1> | HEALTH_OF_AT_<AT1> |
| HEALTH_OF_MSR_<MSR2> | HEALTH_OF_MSR_CTGRY_<MSR_CTG2> | HEALTH_OF_AT_<AT2> |
| HEALTH_OF_MSR_<MSR3> | HEALTH_OF_MSR_CTGRY_<MSR_CTG3> | HEALTH_OF_AT_<AT3> |
| | One such for every measure category under Analysis Type for which health is being identified | One such for every Analysis Type under Analysis Object for which health is being identified |
| VALUE_OF_MEASURE_<MSR1> | | |
| VALUE_OF_MEASURE_<MSR2> | | |
| VALUE_OF_MEASURE_<MSR3> | | |
| One such for every measure under measure category for which health is being identified | | |

*FIG. 24A*

INTERACTIVE GRAPHICAL USER INTERFACE FOR MONITORING COMPUTER MODELS

CROSS-REFERENCE TO RELATED APPLICATIONS

This application is a continuation-in-part of U.S. application Ser. No. 17/527,889, filed Nov. 16, 2021, which claims the benefit and priority of Indian Application No. 202114052608, filed Nov. 16, 2021, which claims the benefit and priority of Provisional Indian Application No. 202011049888, filed Nov. 16, 2020, and this application claims the benefit and priority to a patent of addition of Indian Application No. 202114052608, filed Jul. 7, 2022, disclosures of each of which are incorporated herein by reference in their entirety.

BACKGROUND

Computer models may become unreliable or otherwise fail to accurately model a system. For instance, a computer model may rely on assumptions that change over time, or the computer model may be updated based on new data that corrupts the computer model. Aspects of a computer model can be measured to determine the continued health of the computer model.

SUMMARY

In an example embodiment, a computer-program product tangibly embodied in a non-transitory machine-readable storage medium is provided. The computer-program product includes instructions to cause a computing system to establish a hierarchy for monitoring one or more trained models. The hierarchy comprises an association between each of multiple measures of a measure level of the hierarchy and one or more intermediate levels of the hierarchy. An intermediate level comprises one or more of a measurement category or analysis type. The hierarchy comprises an association between the one or more intermediate levels and at least one trained model of the one or more trained models. The computer-program product includes instructions to cause a computing system to monitor the one or more trained models by generating health measurements. Each of the health measurements corresponds to one of the multiple measures. Each of the health measurements indicates a performance of a monitored model of the one or more trained models according to a measurement category or analysis type associated in the hierarchy with the respective measure of the multiple measures. The computer-program product includes instructions to cause a computing system to generate a visualization in a graphical user interface. The visualization comprises a graphical representation of an indication of a health measurement for each of one or more measures of the multiple measures. The visualization comprises a graphical representation of associations, in the hierarchy, with the one or more measures of the multiple measures, the measure level of the hierarchy, the intermediate level, and the at least one trained model. The computer-program product includes instructions to cause a computing system to update the visualization responsive to an updated measurement for a measurement in the visualization.

In another example embodiment, a computing device is provided. The computing device includes, but is not limited to, a processor and memory. The memory contains instructions that when executed by the processor control the computing device to establish a hierarchy for monitoring one or more trained models. The hierarchy comprises an association between each of multiple measures of a measure level of the hierarchy and one or more intermediate levels of the hierarchy. An intermediate level comprises one or more of a measurement category or analysis type. The hierarchy comprises an association between the one or more intermediate levels and at least one trained model of the one or more trained models. The memory contains instructions that when executed by the processor control the computing device to monitor the one or more trained models by generating health measurements. Each of the health measurements corresponds to one of the multiple measures. Each of the health measurements indicates a performance of a monitored model of the one or more trained models according to a measurement category or analysis type associated in the hierarchy with the respective measure of the multiple measures. The memory contains instructions that when executed by the processor control the computing device to generate a visualization in a graphical user interface. The visualization comprises a graphical representation of an indication of a health measurement for each of one or more measures of the multiple measures. The visualization comprises a graphical representation of associations, in the hierarchy, with the one or more measures of the multiple measures, the measure level of the hierarchy, the intermediate level, and the at least one trained model. The memory contains instructions that when executed by the processor control the computing device to update the visualization responsive to an updated measurement for a measurement in the visualization.

In another example embodiment, a method is provided. The method comprises establishing a hierarchy for monitoring one or more trained models. The hierarchy comprises an association between each of multiple measures of a measure level of the hierarchy and one or more intermediate levels of the hierarchy. An intermediate level comprises one or more of a measurement category or analysis type. The hierarchy comprises an association between the one or more intermediate levels and at least one trained model of the one or more trained models. The method comprises monitoring the one or more trained models by generating health measurements. Each of the health measurements corresponds to one of the multiple measures. Each of the health measurements indicates a performance of a monitored model of the one or more trained models according to a measurement category or analysis type associated in the hierarchy with the respective measure of the multiple measures. The method comprises generating a visualization in a graphical user interface. The visualization comprises a graphical representation of an indication of a health measurement for each of one or more measures of the multiple measures. The visualization comprises a graphical representation of associations, in the hierarchy, with the one or more measures of the multiple measures, the measure level of the hierarchy, the intermediate level, and the at least one trained model. The method comprises updating the visualization responsive to an updated measurement for a measurement in the visualization. In one or more embodiments, a computing system is configured to implement the method.

Other features and aspects of example embodiments are presented below in the Detailed Description when read in connection with the drawings presented with this application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 19A-19B illustrate example interactive graphical user interfaces for generating an intermediate level according to at least one embodiment of the present technology.

FIGS. 20A-20C illustrate example interactive graphical user interfaces for generating a measure according to at least one embodiment of the present technology.

FIGS. 24A-24D illustrate example graphical user interfaces for configuring a visualization according to at least one embodiment of the present technology.

DETAILED DESCRIPTION

In the following description, for the purposes of explanation, specific details are set forth in order to provide a thorough understanding of embodiments of the technology. However, it will be apparent that various embodiments may be practiced without these specific details. The figures and description are not intended to be restrictive.

The ensuing description provides example embodiments only, and is not intended to limit the scope, applicability, or configuration of the disclosure. Rather, the ensuing description of the example embodiments will provide those skilled in the art with an enabling description for implementing an example embodiment. It should be understood that various changes may be made in the function and arrangement of elements without departing from the spirit and scope of the technology as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional operations not included in a figure. A process may correspond to a method, a function, a procedure, a subroutine, a subprogram, etc. When a process corresponds to a function, its termination can correspond to a return of the function to the calling function or the main function.

Systems depicted in some of the figures may be provided in various configurations. In some embodiments, the systems may be configured as a distributed system where one or more components of the system are distributed across one or more networks in a cloud computing system.

Figure 1:
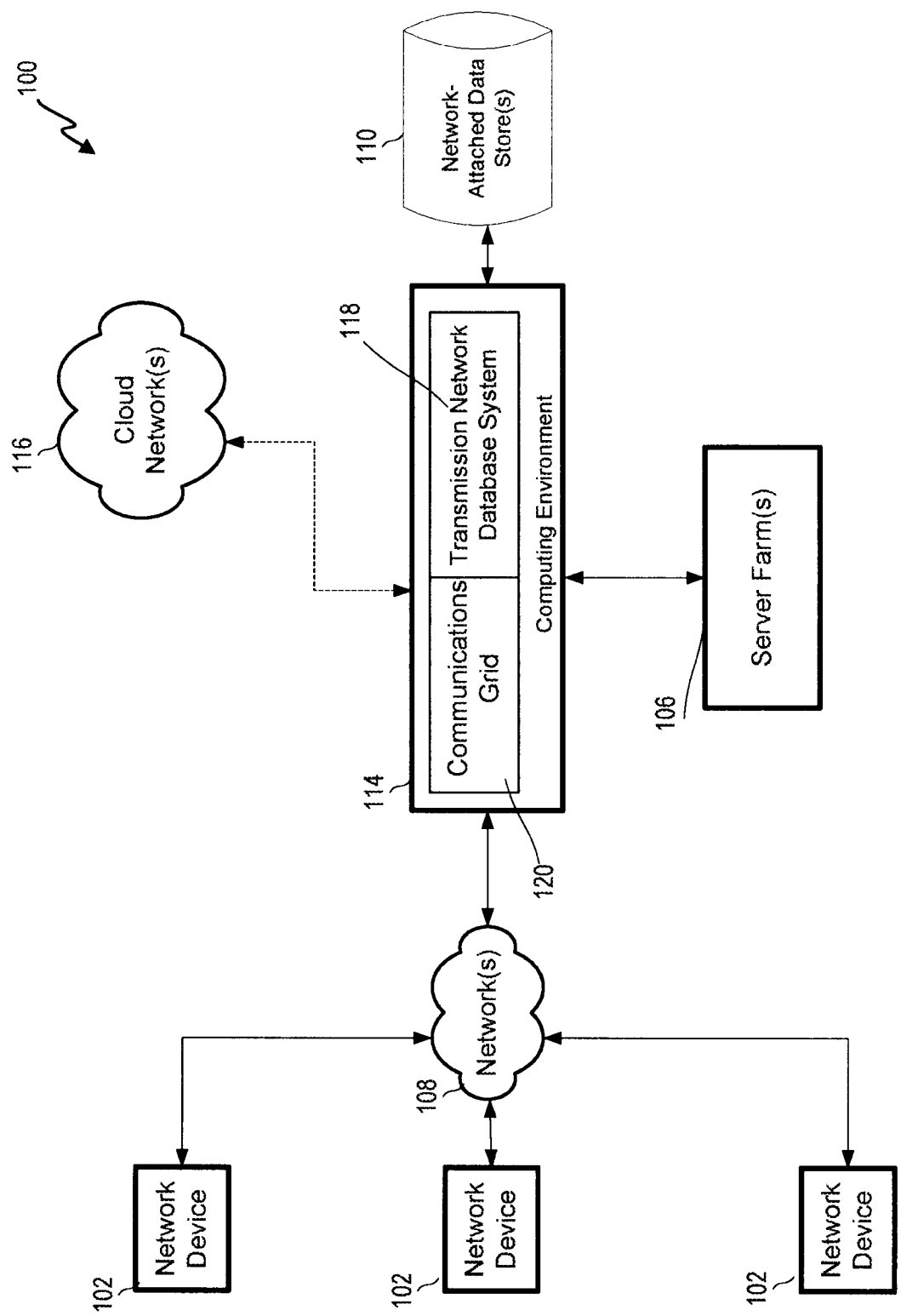
FIG. 1 illustrates a block diagram that provides an illustration of the hardware components of a computing system, according to at least one embodiment of the present technology.

FIG. 1 is a block diagram that provides an illustration of the hardware components of a data transmission network 100, according to embodiments of the present technology. Data transmission network 100 is a specialized computer system that may be used for processing large amounts of data where a large number of computer processing cycles are required.

Data transmission network 100 may also include computing environment 114. Computing environment 114 may be a specialized computer or other machine that processes the data received within the data transmission network 100. Data transmission network 100 also includes one or more network devices 102. Network devices 102 may include client devices that attempt to communicate with computing environment 114. For example, network devices 102 may send data to the computing environment 114 to be processed, may send signals to the computing environment 114 to control different aspects of the computing environment or the data it is processing, among other reasons. Network devices 102 may interact with the computing environment 114 through a number of ways, such as, for example, over one or more networks 108. As shown in FIG. 1, computing environment 114 may include one or more other systems. For example, computing environment 114 may include a database system 118 and/or a communications grid 120.

Figure 8:
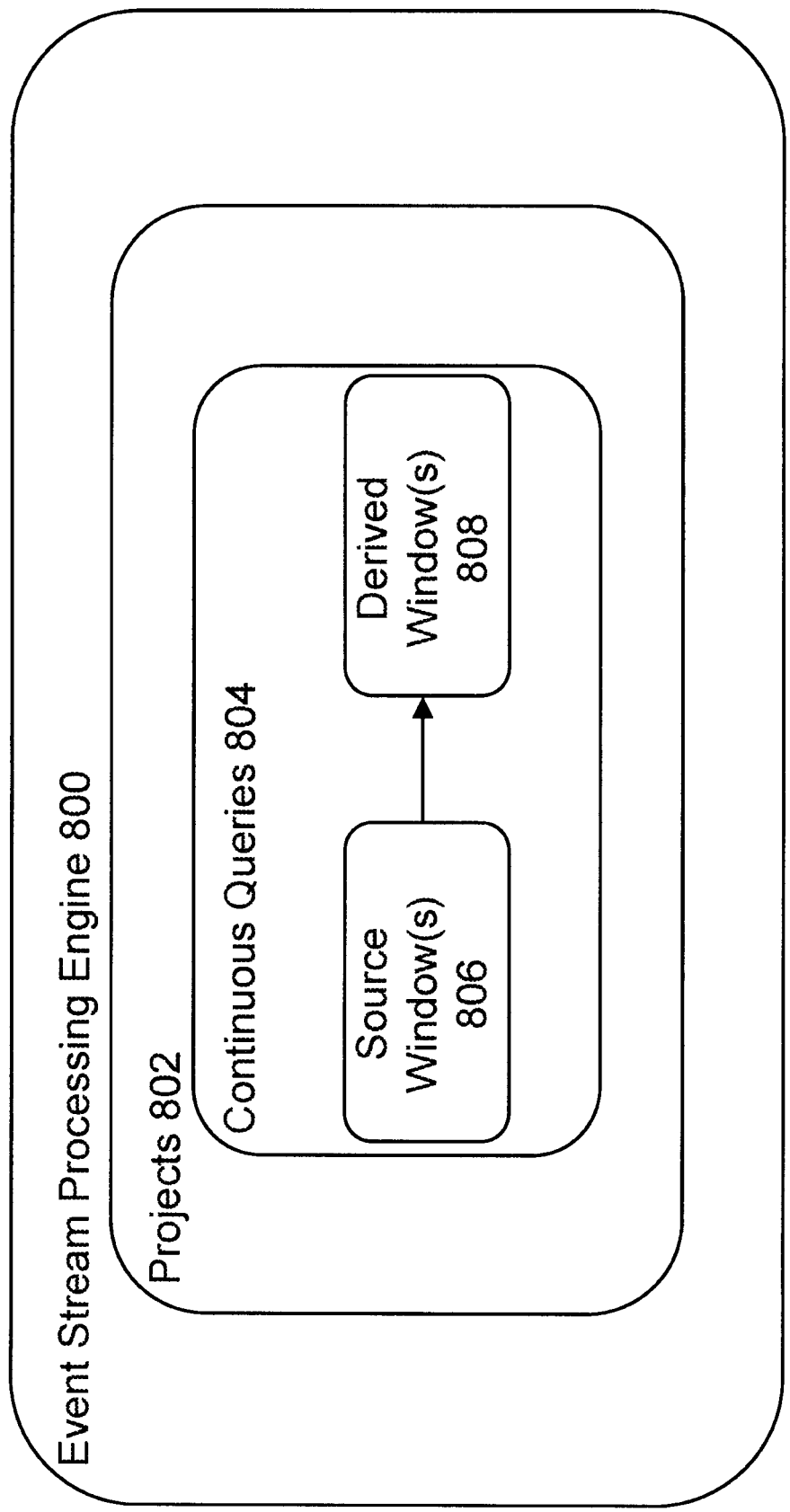
FIG. 8 illustrates a block diagram including components of an Event Stream Processing Engine (ESPE), according to at least one embodiment of the present technology.
Figure 9:
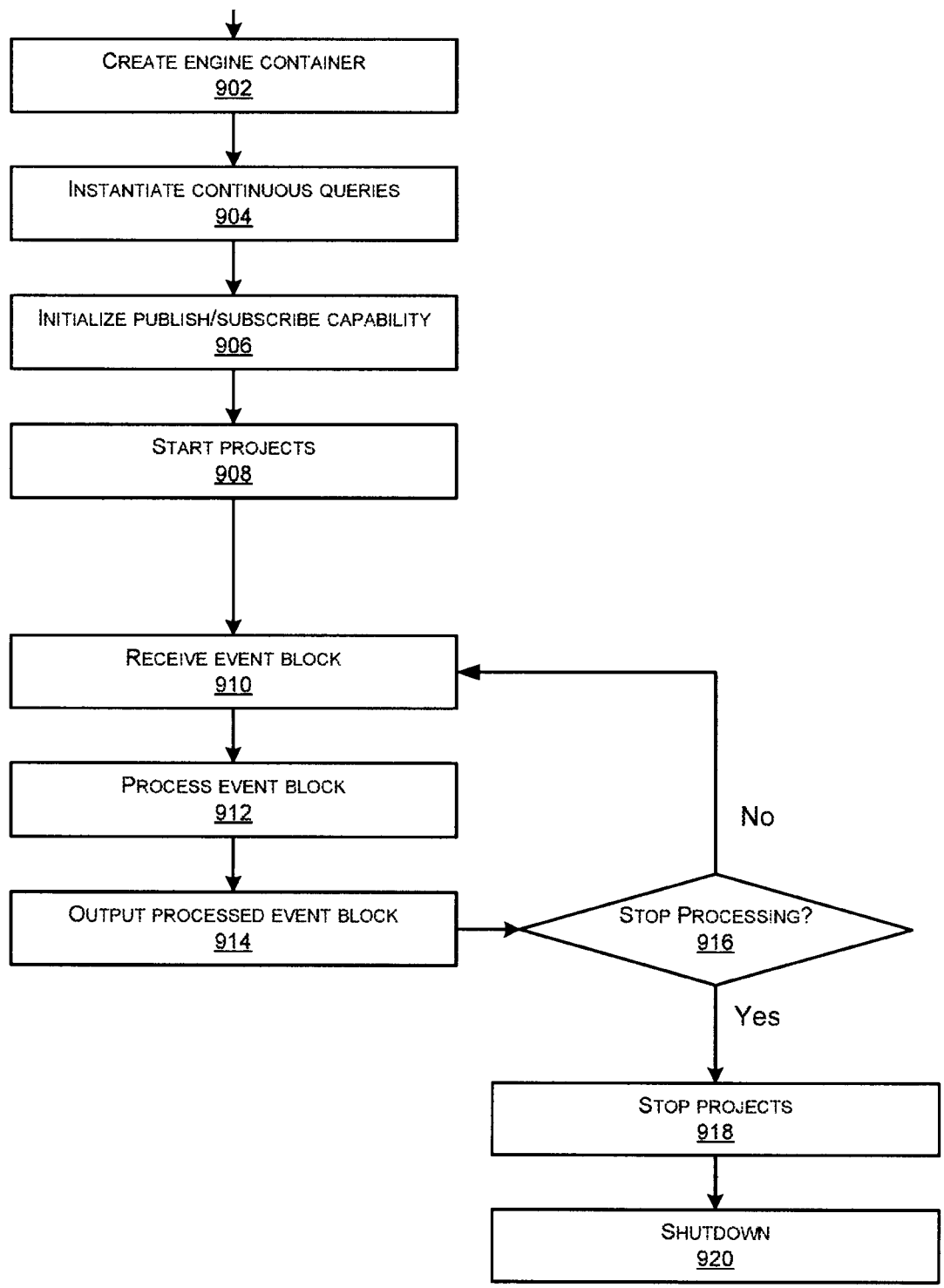
FIG. 9 illustrates a flow chart showing an example process including operations performed by an event stream processing engine, according to at least one embodiment of the present technology.
Figure 10:
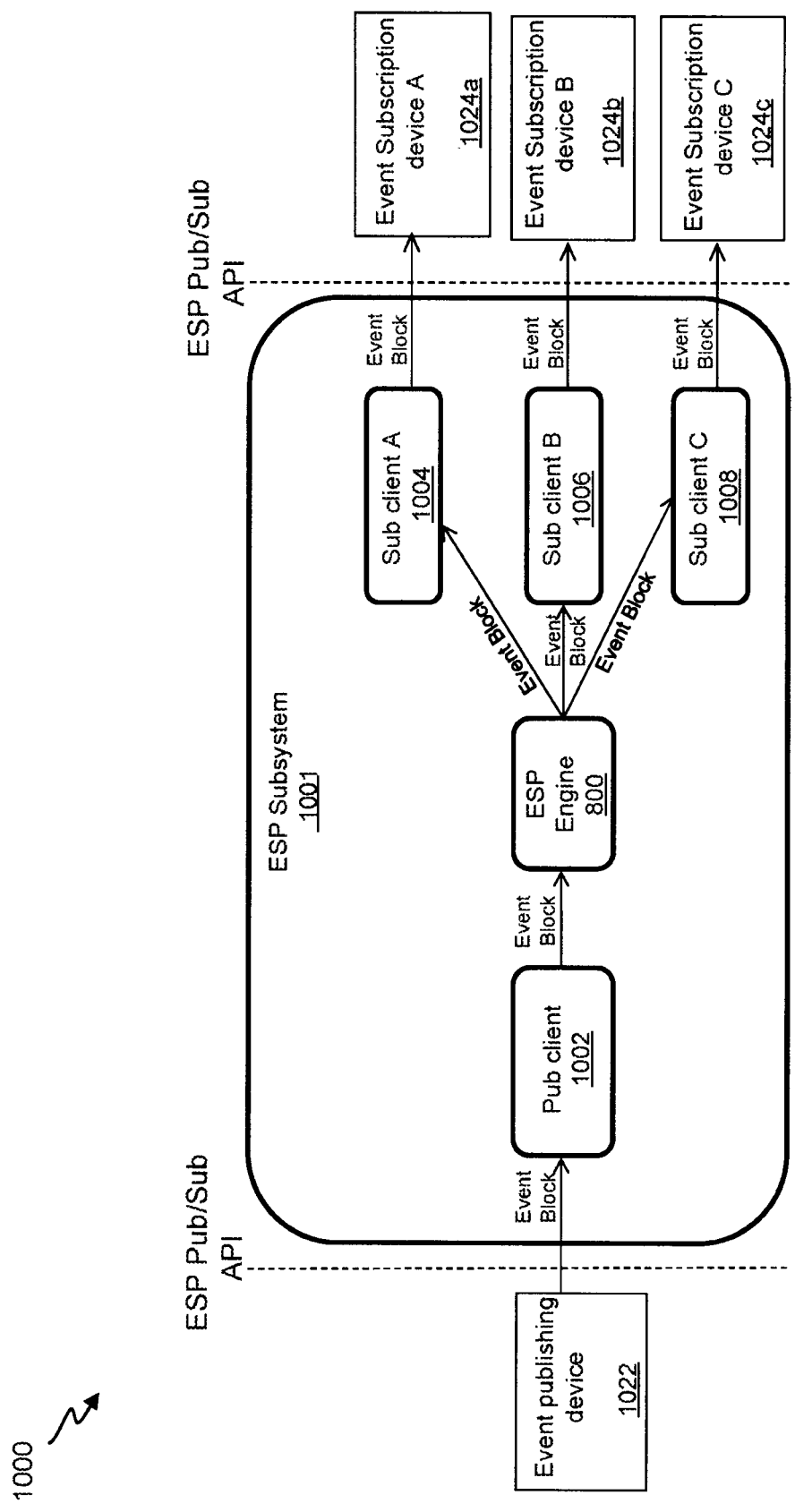
FIG. 10 illustrates an ESP system interfacing between a publishing device and multiple event subscribing devices, according to at least one embodiment of the present technology.

In other embodiments, network devices may provide a large amount of data, either all at once or streaming over a period of time (e.g., using event stream processing (ESP), described further with respect to FIGS. 8-10), to the computing environment 114 via networks 108. For example, network devices 102 may include network computers, sensors, databases, or other devices that may transmit or otherwise provide data to computing environment 114. For example, network devices may include local area network devices, such as routers, hubs, switches, or other computer networking devices. These devices may provide a variety of stored or generated data, such as network data or data specific to the network devices themselves. Network devices may also include sensors that monitor their environment or other devices to collect data regarding that environment or those devices, and such network devices may provide data they collect over time. Network devices may also include devices within the internet of things, such as devices within a home automation network. Some of these devices may be referred to as edge devices, and may involve edge computing circuitry. Data may be transmitted by network devices directly to computing environment 114 or to network-attached data stores, such as network-attached data stores 110 for storage so that the data may be retrieved later by the computing environment 114 or other portions of data transmission network 100.

Data transmission network 100 may also include one or more network-attached data stores 110. Network-attached data stores 110 are used to store data to be processed by the computing environment 114 as well as any intermediate or final data generated by the computing system in non-volatile memory. However in certain embodiments, the configuration of the computing environment 114 allows its operations to be performed such that intermediate and final data results can be stored solely in volatile memory (e.g., RAM), without a requirement that intermediate or final data results be stored to non-volatile types of memory (e.g., disk). This can be useful in certain situations, such as when the computing environment 114 receives ad hoc queries from a user and when responses, which are generated by processing large amounts of data, need to be generated on-the-fly. In this non-limiting situation, the computing environment 114 may be configured to retain the processed information within memory so that responses can be generated for the user at different levels of detail as well as allow a user to interactively query against this information.

Network-attached data stores may store a variety of different types of data organized in a variety of different ways and from a variety of different sources. For example, network-attached data storage may include storage other than primary storage located within computing environment 114 that is directly accessible by processors located therein. Network-attached data storage may include secondary, tertiary or auxiliary storage, such as large hard drives, servers, virtual memory, among other types. Storage devices may include portable or non-portable storage devices, optical storage devices, and various other mediums capable of storing, containing data. A machine-readable storage medium or computer-readable storage medium may include a non-transitory medium in which data can be stored and that does not include carrier waves and/or transitory electronic signals. Examples of a non-transitory medium may include, for example, a magnetic disk or tape, optical storage media such as compact disk or digital versatile disk, flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. Furthermore, the data stores may hold a variety of different types of data. For example, network-attached data stores 110 may hold unstructured (e.g., raw) data, such as manufacturing data (e.g., a database containing records identifying products being manufactured with parameter data for each product, such as colors and models) or product sales databases (e.g., a database containing individual data records identifying details of individual product sales).

The unstructured data may be presented to the computing environment 114 in different forms such as a flat file or a conglomerate of data records, and may have data values and accompanying time stamps. The computing environment 114 may be used to analyze the unstructured data in a variety of ways to determine the best way to structure (e.g., hierarchically) that data, such that the structured data is tailored to a type of further analysis that a user wishes to perform on the data. For example, after being processed, the unstructured time stamped data may be aggregated by time (e.g., into daily time period units) to generate time series data and/or structured hierarchically according to one or more dimensions (e.g., parameters, attributes, and/or variables). For example, data may be stored in a hierarchical data structure, such as a ROLAP OR MOLAP database, or may be stored in another tabular form, such as in a flat-hierarchy form.

Data transmission network 100 may also include one or more server farms 106. Computing environment 114 may route select communications or data to the one or more sever farms 106 or one or more servers within the server farms. Server farms 106 can be configured to provide information in a predetermined manner. For example, server farms 106 may access data to transmit in response to a communication. Server farms 106 may be separately housed from each other device within data transmission network 100, such as computing environment 114, and/or may be part of a device or system.

Server farms 106 may host a variety of different types of data processing as part of data transmission network 100. Server farms 106 may receive a variety of different data from network devices, from computing environment 114, from cloud network 116, or from other sources. The data may have been obtained or collected from one or more sensors, as inputs from a control database, or may have been received as inputs from an external system or device. Server farms 106 may assist in processing the data by turning raw data into processed data based on one or more rules implemented by the server farms. For example, sensor data may be analyzed to determine changes in an environment over time or in real-time.

Data transmission network 100 may also include one or more cloud networks 116. Cloud network 116 may include a cloud infrastructure system that provides cloud services. In certain embodiments, services provided by the cloud network 116 may include a host of services that are made available to users of the cloud infrastructure system on demand. Cloud network 116 is shown in FIG. 1 as being connected to computing environment 114 (and therefore having computing environment 114 as its client or user), but cloud network 116 may be connected to or utilized by any of the devices in FIG. 1. Services provided by the cloud network can dynamically scale to meet the needs of its users. The cloud network 116 may include one or more computers, servers, and/or systems. In some embodiments, the computers, servers, and/or systems that make up the cloud network 116 are different from the user's own on-premises computers, servers, and/or systems. For example, the cloud network 116 may host an application, and a user may, via a communication network such as the Internet, on demand, order and use the application.

While each device, server and system in FIG. 1 is shown as a single device, it will be appreciated that multiple devices may instead be used. For example, a set of network devices can be used to transmit various communications from a single user, or a remote server may include a server stack. As another example, data may be processed as part of computing environment 114.

Each communication within data transmission network 100 (e.g., between client devices, between a device and connection management system, between servers 106 and computing environment 114 or between a server and a device) may occur over one or more networks 108. Networks 108 may include one or more of a variety of different types of networks, including a wireless network, a wired network, or a combination of a wired and wireless network. Examples of suitable networks include the Internet, a personal area network, a local area network (LAN), a wide area network (WAN), or a wireless local area network (WLAN). A wireless network may include a wireless interface or combination of wireless interfaces. As an example, a network in the one or more networks 108 may include a short-range communication channel, such as a Bluetooth or a Bluetooth Low Energy channel. A wired network may include a wired interface. The wired and/or wireless networks may be implemented using routers, access points, bridges, gateways, or the like, to connect devices in the network 108, as will be further described with respect to FIG. 2. The one or more networks 108 can be incorporated entirely within or can include an intranet, an extranet, or a combination thereof. In one embodiment, communications between two or more systems and/or devices can be achieved by a secure communications protocol, such as secure sockets layer (SSL) or transport layer security (TLS). In addition, data and/or transactional details may be encrypted.

Some aspects may utilize the Internet of Things (IoT), where things (e.g., machines, devices, phones, sensors) can be connected to networks and the data from these things can be collected and processed within the things and/or external to the things. For example, the IoT can include sensors in many different devices, and high value analytics can be applied to identify hidden relationships and drive increased efficiencies. This can apply to both big data analytics and real-time (e.g., ESP) analytics. IoT may be implemented in various areas, such as for access (technologies that get data and move it), embed-ability (devices with embedded sensors), and services. Industries in the IoT space may include automotive (connected car), manufacturing (connected factory), smart cities, energy and retail. This will be described further below with respect to FIG. 2.

As noted, computing environment 114 may include a communications grid 120 and a transmission network database system 118. Communications grid 120 may be a grid-based computing system for processing large amounts of data. The transmission network database system 118 may be for managing, storing, and retrieving large amounts of data that are distributed to and stored in the one or more network-attached data stores 110 or other data stores that reside at different locations within the transmission network database system 118. The compute nodes in the grid-based computing system 120 and the transmission network database system 118 may share the same processor hardware, such as processors that are located within computing environment 114.

Figure 2:
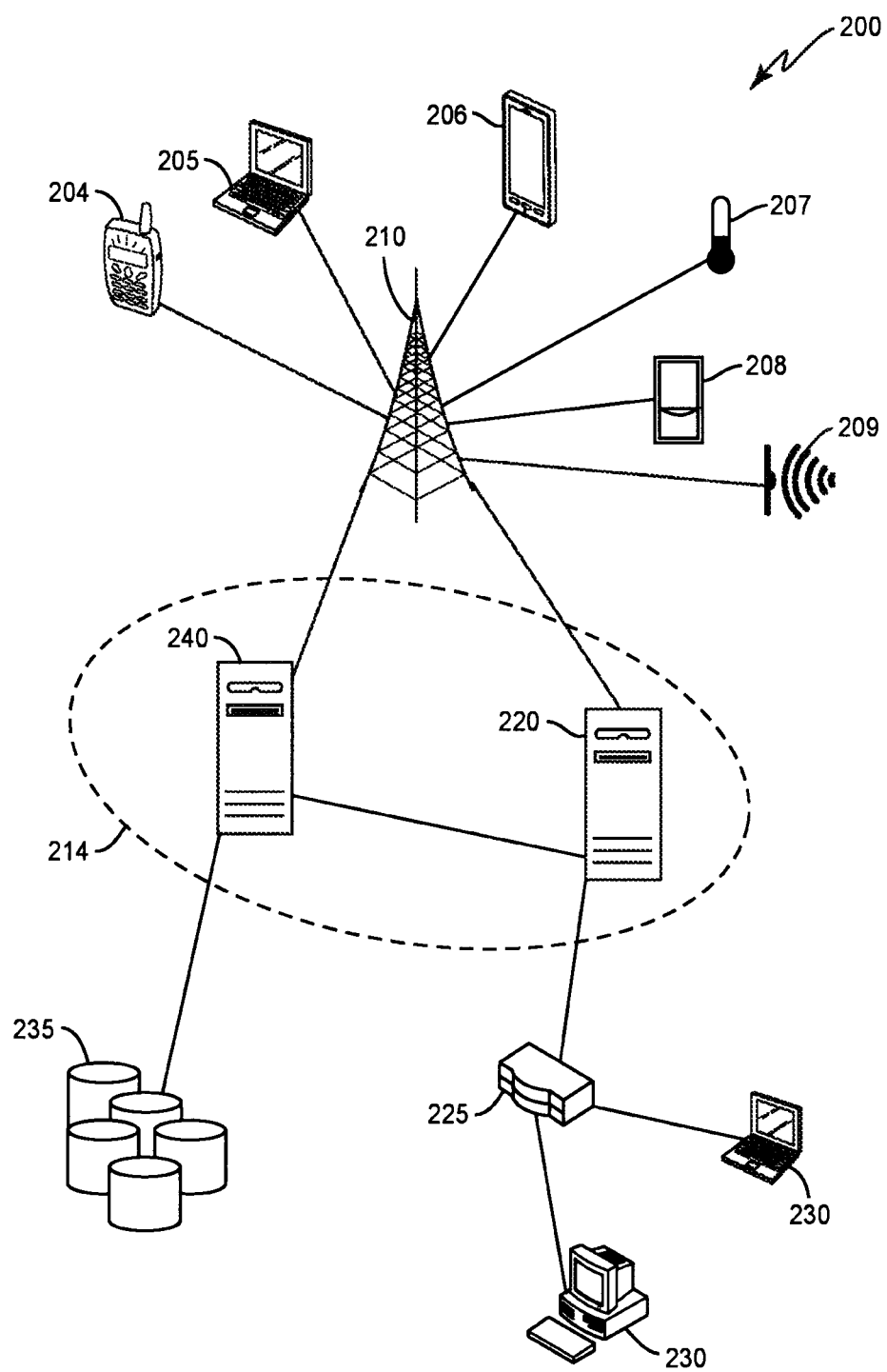
FIG. 2 illustrates an example network including an example set of devices communicating with each other over an exchange system and via a network, according to at least one embodiment of the present technology.

FIG. 2 illustrates an example network including an example set of devices communicating with each other over an exchange system and via a network, according to embodiments of the present technology. As noted, each communication within data transmission network 100 may occur over one or more networks. System 200 includes a network device 204 configured to communicate with a variety of types of client devices, for example client devices 230, over a variety of types of communication channels.

As shown in FIG. 2, network device 204 can transmit a communication over a network (e.g., a cellular network via a base station 210). The communication can be routed to another network device, such as network devices 205-209, via base station 210. The communication can also be routed to computing environment 214 via base station 210. For example, network device 204 may collect data either from its surrounding environment or from other network devices (such as network devices 205-209) and transmit that data to computing environment 214.

Although network devices 204-209 are shown in FIG. 2 as a mobile phone, laptop computer, tablet computer, temperature sensor, motion sensor, and audio sensor respectively, the network devices may be or include sensors that are sensitive to detecting aspects of their environment. For example, the network devices may include sensors such as water sensors, power sensors, electrical current sensors, chemical sensors, optical sensors, pressure sensors, geographic or position sensors (e.g., GPS), velocity sensors, acceleration sensors, flow rate sensors, among others. Examples of characteristics that may be sensed include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, electrical current, among others. The sensors may be mounted to various components used as part of a variety of different types of systems (e.g., an oil drilling operation). The network devices may detect and record data related to the environment that it monitors, and transmit that data to computing environment 214.

As noted, one type of system that may include various sensors that collect data to be processed and/or transmitted to a computing environment according to certain embodiments includes an oil drilling system. For example, the one or more drilling operation sensors may include surface sensors that measure a hook load, a fluid rate, a temperature and a density in and out of the wellbore, a standpipe pressure, a surface torque, a rotation speed of a drill pipe, a rate of penetration, a mechanical specific energy, etc. and downhole sensors that measure a rotation speed of a bit, fluid densities, downhole torque, downhole vibration (axial, tangential, lateral), a weight applied at a drill bit, an annular pressure, a differential pressure, an azimuth, an inclination, a dog leg severity, a measured depth, a vertical depth, a downhole temperature, etc. Besides the raw data collected directly by the sensors, other data may include parameters either developed by the sensors or assigned to the system by a client or other controlling device. For example, one or more drilling operation control parameters may control settings such as a mud motor speed to flow ratio, a bit diameter, a predicted formation top, seismic data, weather data, etc. Other data may be generated using physical models such as an earth model, a weather model, a seismic model, a bottom hole assembly model, a well plan model, an annular friction model, etc. In addition to sensor and control settings, predicted outputs, of for example, the rate of penetration, mechanical specific energy, hook load, flow in fluid rate, flow out fluid rate, pump pressure, surface torque, rotation speed of the drill pipe, annular pressure, annular friction pressure, annular temperature, equivalent circulating density, etc. may also be stored in the data warehouse.

In another example, another type of system that may include various sensors that collect data to be processed and/or transmitted to a computing environment according to certain embodiments includes a home automation or similar automated network in a different environment, such as an office space, school, public space, sports venue, or a variety of other locations. Network devices in such an automated network may include network devices that allow a user to access, control, and/or configure various home appliances located within the user's home (e.g., a television, radio, light, fan, humidifier, sensor, microwave, iron, and/or the like), or outside of the user's home (e.g., exterior motion sensors, exterior lighting, garage door openers, sprinkler systems, or the like). For example, network device 102 may include a home automation switch that may be coupled with a home appliance. In another embodiment, a network device can allow a user to access, control, and/or configure devices, such as office-related devices (e.g., copy machine, printer, or fax machine), audio and/or video related devices (e.g., a receiver, a speaker, a projector, a DVD player, or a television), media-playback devices (e.g., a compact disc player, a CD player, or the like), computing devices (e.g., a home computer, a laptop computer, a tablet, a personal digital assistant (PDA), a computing device, or a wearable device), lighting devices (e.g., a lamp or recessed lighting), devices associated with a security system, devices associated with an alarm system, devices that can be operated in an automobile (e.g., radio devices, navigation devices), and/or the like. Data may be collected from such various sensors in raw form, or data may be processed by the sensors to create parameters or other data either developed by the sensors based on the raw data or assigned to the system by a client or other controlling device.

In another example, another type of system that may include various sensors that collect data to be processed and/or transmitted to a computing environment according to certain embodiments includes a power or energy grid. A variety of different network devices may be included in an energy grid, such as various devices within one or more power plants, energy farms (e.g., wind farm, solar farm, among others) energy storage facilities, factories, homes and businesses of consumers, among others. One or more of such devices may include one or more sensors that detect energy gain or loss, electrical input or output or loss, and a variety of other efficiencies. These sensors may collect data to inform users of how the energy grid, and individual devices within the grid, may be functioning and how they may be made more efficient.

Network device sensors may also perform processing on data it collects before transmitting the data to the computing environment 114, or before deciding whether to transmit data to the computing environment 114. For example, network devices may determine whether data collected meets certain rules, for example by comparing data or values calculated from the data and comparing that data to one or more thresholds. The network device may use this data and/or comparisons to determine if the data should be transmitted to the computing environment 214 for further use or processing.

Computing environment 214 may include machines 220 and 240. Although computing environment 214 is shown in FIG. 2 as having two machines, 220 and 240, computing environment 214 may have only one machine or may have more than two machines. The machines that make up computing environment 214 may include specialized computers, servers, or other machines that are configured to individually and/or collectively process large amounts of data. The computing environment 214 may also include storage devices that include one or more databases of structured data, such as data organized in one or more hierarchies, or unstructured data. The databases may communicate with the processing devices within computing environment 214 to distribute data to them. Since network devices may transmit data to computing environment 214, that data may be received by the computing environment 214 and subsequently stored within those storage devices. Data used by computing environment 214 may also be stored in data stores 235, which may also be a part of or connected to computing environment 214.

Computing environment 214 can communicate with various devices via one or more routers 225 or other inter-network or intra-network connection components. For example, computing environment 214 may communicate with devices 230 via one or more routers 225. Computing environment 214 may collect, analyze and/or store data from or pertaining to communications, client device operations, client rules, and/or user-associated actions stored at one or more data stores 235. Such data may influence communication routing to the devices within computing environment 214, how data is stored or processed within computing environment 214, among other actions.

Notably, various other devices can further be used to influence communication routing and/or processing between devices within computing environment 214 and with devices outside of computing environment 214. For example, as shown in FIG. 2, computing environment 214 may include a web server 240. Thus, computing environment 214 can retrieve data of interest, such as client information (e.g., product information, client rules, etc.), technical product details, news, current or predicted weather, and so on.

In addition to computing environment 214 collecting data (e.g., as received from network devices, such as sensors, and client devices or other sources) to be processed as part of a big data analytics project, it may also receive data in real time as part of a streaming analytics environment. As noted, data may be collected using a variety of sources as communicated via different kinds of networks or locally. Such data may be received on a real-time streaming basis. For example, network devices may receive data periodically from network device sensors as the sensors continuously sense, monitor and track changes in their environments. Devices within computing environment 214 may also perform pre-analysis on data it receives to determine if the data received should be processed as part of an ongoing project. The data received and collected by computing environment 214, no matter what the source or method or timing of receipt, may be processed over a period of time for a client to determine results data based on the client's needs and rules.

Figure 3:
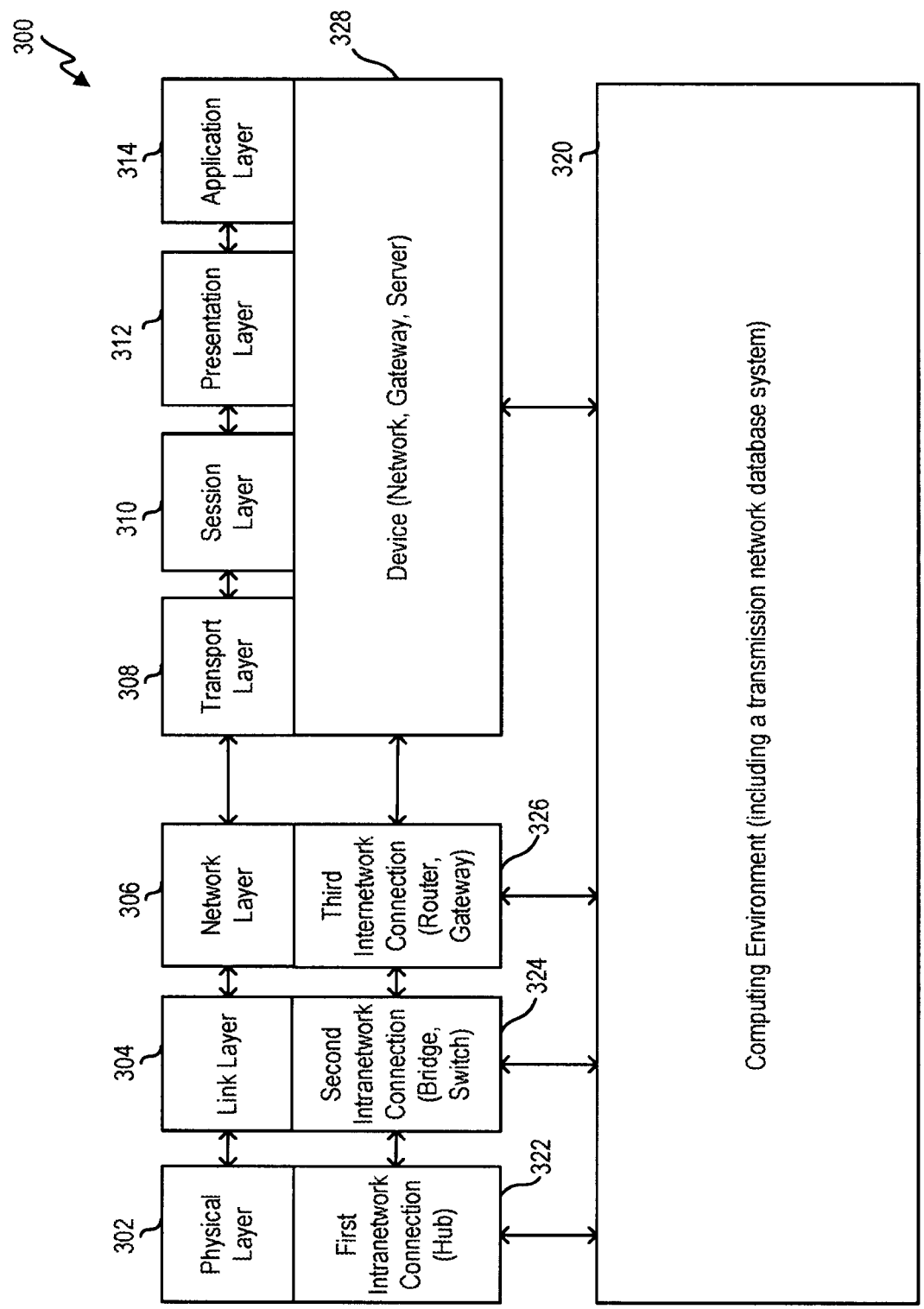
FIG. 3 illustrates a representation of a conceptual model of a communications protocol system, according to at least one embodiment of the present technology.

FIG. 3 illustrates a representation of a conceptual model of a communications protocol system, according to embodiments of the present technology. More specifically, FIG. 3 identifies operation of a computing environment in an Open Systems Interaction model that corresponds to various connection components. The model 300 shows, for example, how a computing environment, such as computing environment 320 (or computing environment 214 in FIG. 2) may communicate with other devices in its network, and control how communications between the computing environment and other devices are executed and under what conditions.

The model can include layers 302-314. The layers are arranged in a stack. Each layer in the stack serves the layer one level higher than it (except for the application layer, which is the highest layer), and is served by the layer one level below it (except for the physical layer, which is the lowest layer). The physical layer is the lowest layer because it receives and transmits raw bytes of data and is the farthest layer from the user in a communications system. On the other hand, the application layer is the highest layer because it interacts directly with a software application.

As noted, the model includes a physical layer 302. Physical layer 302 represents physical communication and can define parameters of that physical communication. For example, such physical communication may come in the form of electrical, optical, or electromagnetic signals. Physical layer 302 also defines protocols that may control communications within a data transmission network.

Link layer 304 defines links and mechanisms used to transmit (i.e., move) data across a network. The link layer manages node-to-node communications, such as within a grid computing environment. Link layer 304 can detect and correct errors (e.g., transmission errors in the physical layer 302). Link layer 304 can also include a media access control (MAC) layer and logical link control (LLC) layer.

Network layer 306 defines the protocol for routing within a network. In other words, the network layer coordinates transferring data across nodes in a same network (e.g., such as a grid computing environment). Network layer 306 can also define the processes used to structure local addressing within the network.

Transport layer 308 can manage the transmission of data and the quality of the transmission and/or receipt of that data. Transport layer 308 can provide a protocol for transferring data, such as, for example, a Transmission Control Protocol (TCP). Transport layer 308 can assemble and disassemble data frames for transmission. The transport layer can also detect transmission errors occurring in the layers below it.

Session layer 310 can establish, maintain, and manage communication connections between devices on a network. In other words, the session layer controls the dialogues or nature of communications between network devices on the network. The session layer may also establish checkpointing, adjournment, termination, and restart procedures.

Presentation layer 312 can provide translation for communications between the application and network layers. In other words, this layer may encrypt, decrypt and/or format data based on data types known to be accepted by an application or network layer.

Application layer 314 interacts directly with software applications and end users, and manages communications between them. Application layer 314 can identify destinations, local resource states or availability and/or communication content or formatting using the applications.

Intra-network connection components 322 and 324 are shown to operate in lower levels, such as physical layer 302 and link layer 304, respectively. For example, a hub can operate in the physical layer and a switch can operate in the link layer. Inter-network connection components 326 and 328 are shown to operate on higher levels, such as layers 306-314. For example, routers can operate in the network layer and network devices can operate in the transport, session, presentation, and application layers.

As noted, a computing environment 320 can interact with and/or operate on, in various embodiments, one, more, all or any of the various layers. For example, computing environment 320 can interact with a hub (e.g., via the link layer) so as to adjust which devices the hub communicates with. The physical layer may be served by the link layer, so it may implement such data from the link layer. For example, the computing environment 320 may control which devices it will receive data from. For example, if the computing environment 320 knows that a certain network device has turned off, broken, or otherwise become unavailable or unreliable, the computing environment 320 may instruct the hub to prevent any data from being transmitted to the computing environment 320 from that network device. Such a process may be beneficial to avoid receiving data that is inaccurate or that has been influenced by an uncontrolled environment. As another example, computing environment 320 can communicate with a bridge, switch, router or gateway and influence which device within the system (e.g., system 200) the component selects as a destination. In some embodiments, computing environment 320 can interact with various layers by exchanging communications with equipment operating on a particular layer by routing or modifying existing communications. In another embodiment, such as in a grid computing environment, a node may determine how data within the environment should be routed (e.g., which node should receive certain data) based on certain parameters or information provided by other layers within the model.

As noted, the computing environment 320 may be a part of a communications grid environment, the communications of which may be implemented as shown in the protocol of FIG. 3. For example, referring back to FIG. 2, one or more of machines 220 and 240 may be part of a communications grid computing environment. A gridded computing environment may be employed in a distributed system with non-interactive workloads where data resides in memory on the machines, or compute nodes. In such an environment, analytic code, instead of a database management system, controls the processing performed by the nodes. Data is co-located by pre-distributing it to the grid nodes, and the analytic code on each node loads the local data into memory. Each node may be assigned a particular task such as a portion of a processing project, or to organize or control other nodes within the grid.

Figure 4:
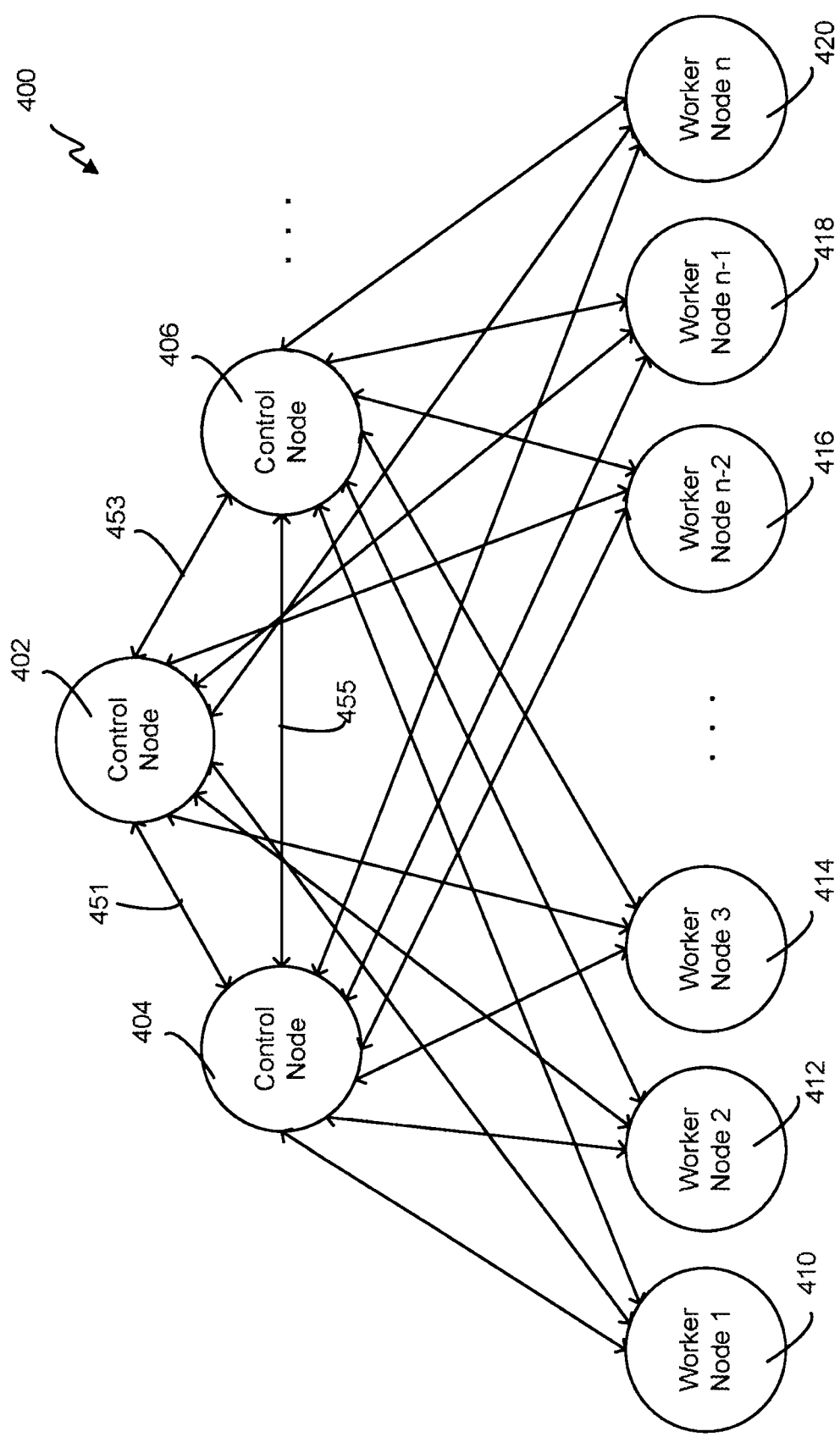
FIG. 4 illustrates a communications grid computing system including a variety of control and worker nodes, according to at least one embodiment of the present technology.

FIG. 4 illustrates a communications grid computing system 400 including a variety of control and worker nodes, according to embodiments of the present technology. Communications grid computing system 400 includes three control nodes and one or more worker nodes. Communications grid computing system 400 includes control nodes 402, 404, and 406. The control nodes are communicatively connected via communication paths 451, 453, and 455. Therefore, the control nodes may transmit information (e.g., related to the communications grid or notifications), to and receive information from each other. Although communications grid computing system 400 is shown in FIG. 4 as including three control nodes, the communications grid may include more or less than three control nodes.

Communications grid computing system (or just "communications grid") 400 also includes one or more worker nodes. Shown in FIG. 4 are six worker nodes 410-420. Although FIG. 4 shows six worker nodes, a communications grid according to embodiments of the present technology may include more or less than six worker nodes. The number of worker nodes included in a communications grid may be dependent upon how large the project or data set is being processed by the communications grid, the capacity of each worker node, the time designated for the communications grid to complete the project, among others. Each worker node within the communications grid 400 may be connected (wired or wirelessly, and directly or indirectly) to control nodes 402-406. Therefore, each worker node may receive information from the control nodes (e.g., an instruction to perform work on a project) and may transmit information to the control nodes (e.g., a result from work performed on a project). Furthermore, worker nodes may communicate with each other (either directly or indirectly). For example, worker nodes may transmit data between each other related to a job being performed or an individual task within a job being performed by that worker node. However, in certain embodiments, worker nodes may not, for example, be connected (communicatively or otherwise) to certain other worker nodes. In an embodiment, worker nodes may only be able to communicate with the control node that controls it, and may not be able to communicate with other worker nodes in the communications grid, whether they are other worker nodes controlled by the control node that controls the worker node, or worker nodes that are controlled by other control nodes in the communications grid.

A control node may connect with an external device with which the control node may communicate (e.g., a grid user, such as a server or computer, may connect to a controller of the grid). For example, a server or computer may connect to control nodes and may transmit a project or job to the node. The project may include a data set. The data set may be of any size. Once the control node receives such a project including a large data set, the control node may distribute the data set or projects related to the data set to be performed by worker nodes. Alternatively, for a project including a large data set, the data set may be received or stored by a machine other than a control node (e.g., a Hadoop data node).

Control nodes may maintain knowledge of the status of the nodes in the grid (i.e., grid status information), accept work requests from clients, subdivide the work across worker nodes, coordinate the worker nodes, among other responsibilities. Worker nodes may accept work requests from a control node and provide the control node with results of the work performed by the worker node. A grid may be started from a single node (e.g., a machine, computer, server, etc.). This first node may be assigned or may start as the primary control node that will control any additional nodes that enter the grid.

When a project is submitted for execution (e.g., by a client or a controller of the grid) it may be assigned to a set of nodes. After the nodes are assigned to a project, a data structure (i.e., a communicator) may be created. The communicator may be used by the project for information to be shared between the project code running on each node. A communication handle may be created on each node. A handle, for example, is a reference to the communicator that is valid within a single process on a single node, and the handle may be used when requesting communications between nodes.

A control node, such as control node 402, may be designated as the primary control node. A server, computer or other external device may connect to the primary control node. Once the control node receives a project, the primary control node may distribute portions of the project to its worker nodes for execution. For example, when a project is initiated on communications grid 400, primary control node 402 controls the work to be performed for the project in order to complete the project as requested or instructed. The primary control node may distribute work to the worker nodes based on various factors, such as which subsets or portions of projects may be completed most efficiently and in the correct amount of time. For example, a worker node may perform analysis on a portion of data that is already local (e.g., stored on) the worker node. The primary control node also coordinates and processes the results of the work performed by each worker node after each worker node executes and completes its job. For example, the primary control node may receive a result from one or more worker nodes, and the control node may organize (e.g., collect and assemble) the results received and compile them to produce a complete result for the project received from the end user.

Any remaining control nodes, such as control nodes 404 and 406, may be assigned as backup control nodes for the project. In an embodiment, backup control nodes may not control any portion of the project. Instead, backup control nodes may serve as a backup for the primary control node and take over as primary control node if the primary control node were to fail. If a communications grid were to include only a single control node, and the control node were to fail (e.g., the control node is shut off or breaks) then the communications grid as a whole may fail and any project or job being run on the communications grid may fail and may not complete. While the project may be run again, such a failure may cause a delay (severe delay in some cases, such as overnight delay) in completion of the project. Therefore, a grid with multiple control nodes, including a backup control node, may be beneficial.

To add another node or machine to the grid, the primary control node may open a pair of listening sockets, for example. A socket may be used to accept work requests from clients, and the second socket may be used to accept connections from other grid nodes. The primary control node may be provided with a list of other nodes (e.g., other machines, computers, servers) that will participate in the grid, and the role that each node will fill in the grid. Upon startup of the primary control node (e.g., the first node on the grid), the primary control node may use a network protocol to start the server process on every other node in the grid. Command line parameters, for example, may inform each node of one or more pieces of information, such as: the role that the node will have in the grid, the host name of the primary control node, the port number on which the primary control node is accepting connections from peer nodes, among others. The information may also be provided in a configuration file, transmitted over a secure shell tunnel, recovered from a configuration server, among others. While the other machines in the grid may not initially know about the configuration of the grid, that information may also be sent to each other node by the primary control node. Updates of the grid information may also be subsequently sent to those nodes.

For any control node other than the primary control node added to the grid, the control node may open three sockets. The first socket may accept work requests from clients, the second socket may accept connections from other grid members, and the third socket may connect (e.g., permanently) to the primary control node. When a control node (e.g., primary control node) receives a connection from another control node, it first checks to see if the peer node is in the list of configured nodes in the grid. If it is not on the list, the control node may clear the connection. If it is on the list, it may then attempt to authenticate the connection. If authentication is successful, the authenticating node may transmit information to its peer, such as the port number on which a node is listening for connections, the host name of the node, information about how to authenticate the node, among other information. When a node, such as the new control node, receives information about another active node, it will check to see if it already has a connection to that other node. If it does not have a connection to that node, it may then establish a connection to that control node.

Any worker node added to the grid may establish a connection to the primary control node and any other control nodes on the grid. After establishing the connection, it may authenticate itself to the grid (e.g., any control nodes, including both primary and backup, or a server or user controlling the grid). After successful authentication, the worker node may accept configuration information from the control node.

When a node joins a communications grid (e.g., when the node is powered on or connected to an existing node on the grid or both), the node is assigned (e.g., by an operating system of the grid) a universally unique identifier (UUID). This unique identifier may help other nodes and external entities (devices, users, etc.) to identify the node and distinguish it from other nodes. When a node is connected to the grid, the node may share its unique identifier with the other nodes in the grid. Since each node may share its unique identifier, each node may know the unique identifier of every other node on the grid. Unique identifiers may also designate a hierarchy of each of the nodes (e.g., backup control nodes) within the grid. For example, the unique identifiers of each of the backup control nodes may be stored in a list of backup control nodes to indicate an order in which the backup control nodes will take over for a failed primary control node to become a new primary control node. However, a hierarchy of nodes may also be determined using methods other than using the unique identifiers of the nodes. For example, the hierarchy may be predetermined, or may be assigned based on other predetermined factors.

The grid may add new machines at any time (e.g., initiated from any control node). Upon adding a new node to the grid, the control node may first add the new node to its table of grid nodes. The control node may also then notify every other control node about the new node. The nodes receiving the notification may acknowledge that they have updated their configuration information.

Primary control node 402 may, for example, transmit one or more communications to backup control nodes 404 and 406 (and, for example, to other control or worker nodes within the communications grid). Such communications may sent periodically, at fixed time intervals, between known fixed stages of the project's execution, among other protocols. The communications transmitted by primary control node 402 may be of varied types and may include a variety of types of information. For example, primary control node 402 may transmit snapshots (e.g., status information) of the communications grid so that backup control node 404 always has a recent snapshot of the communications grid. The snapshot or grid status may include, for example, the structure of the grid (including, for example, the worker nodes in the grid, unique identifiers of the nodes, or their relationships with the primary control node) and the status of a project (including, for example, the status of each worker node's portion of the project). The snapshot may also include analysis or results received from worker nodes in the communications grid. The backup control nodes may receive and store the backup data received from the primary control node. The backup control nodes may transmit a request for such a snapshot (or other information) from the primary control node, or the primary control node may send such information periodically to the backup control nodes.

As noted, the backup data may allow the backup control node to take over as primary control node if the primary control node fails without requiring the grid to start the project over from scratch. If the primary control node fails, the backup control node that will take over as primary control node may retrieve the most recent version of the snapshot received from the primary control node and use the snapshot to continue the project from the stage of the project indicated by the backup data. This may prevent failure of the project as a whole.

A backup control node may use various methods to determine that the primary control node has failed. In one example of such a method, the primary control node may transmit (e.g., periodically) a communication to the backup control node that indicates that the primary control node is working and has not failed, such as a heartbeat communication. The backup control node may determine that the primary control node has failed if the backup control node has not received a heartbeat communication for a certain predetermined period of time. Alternatively, a backup control node may also receive a communication from the primary control node itself (before it failed) or from a worker node that the primary control node has failed, for example because the primary control node has failed to communicate with the worker node.

Different methods may be performed to determine which backup control node of a set of backup control nodes (e.g., backup control nodes 404 and 406) will take over for failed primary control node 402 and become the new primary control node. For example, the new primary control node may be chosen based on a ranking or "hierarchy" of backup control nodes based on their unique identifiers. In an alternative embodiment, a backup control node may be assigned to be the new primary control node by another device in the communications grid or from an external device (e.g., a system infrastructure or an end user, such as a server or computer, controlling the communications grid). In another alternative embodiment, the backup control node that takes over as the new primary control node may be designated based on bandwidth or other statistics about the communications grid.

A worker node within the communications grid may also fail. If a worker node fails, work being performed by the failed worker node may be redistributed amongst the operational worker nodes. In an alternative embodiment, the primary control node may transmit a communication to each of the operable worker nodes still on the communications grid that each of the worker nodes should purposefully fail also. After each of the worker nodes fail, they may each retrieve their most recent saved checkpoint of their status and re-start the project from that checkpoint to minimize lost progress on the project being executed.

Figure 5:
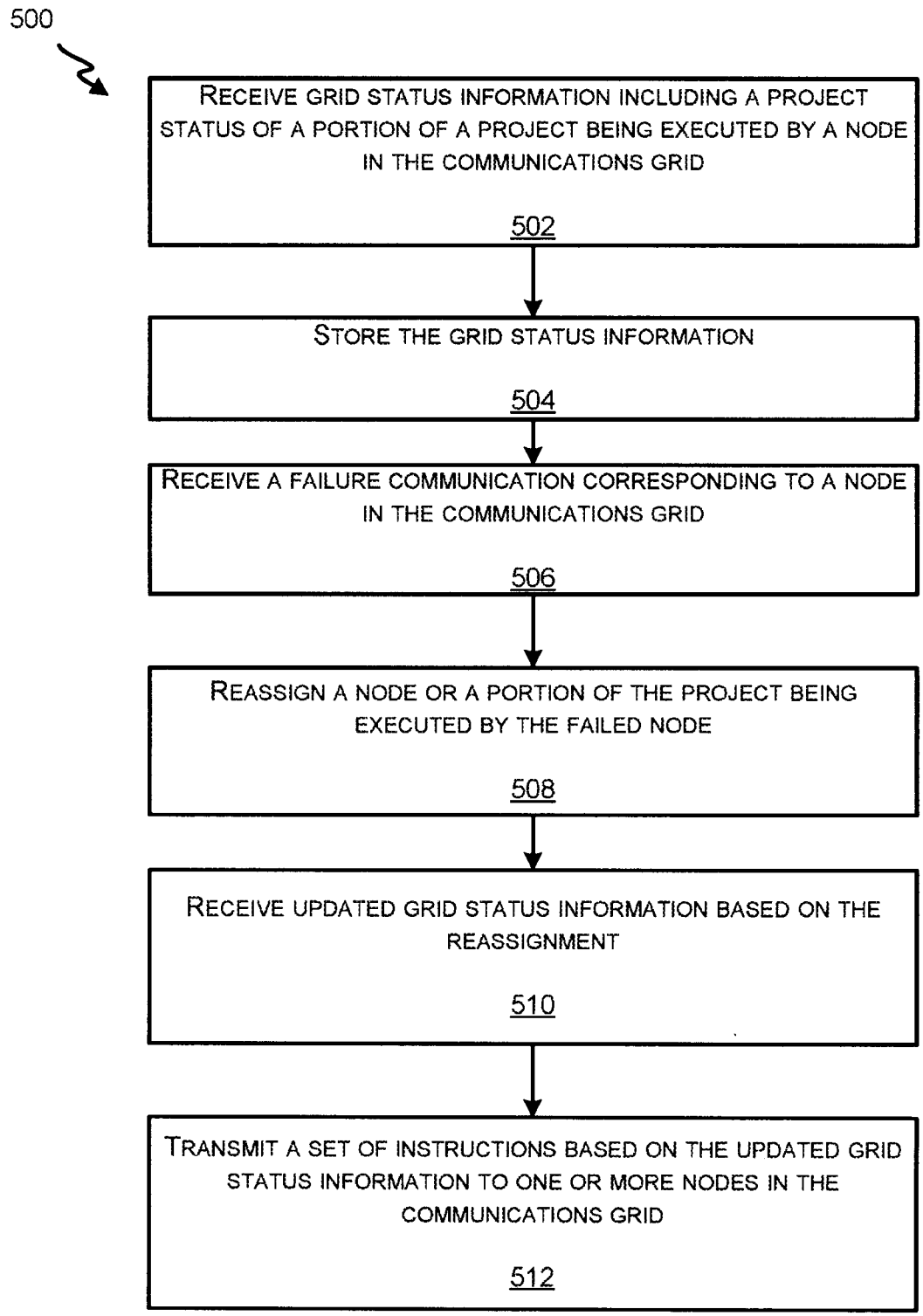
FIG. 5 illustrates a flow chart showing an example process for adjusting a communications grid or a work project in a communications grid after a failure of a node, according to at least one embodiment of the present technology.

FIG. 5 illustrates a flow chart 500 showing an example process for adjusting a communications grid or a work project in a communications grid after a failure of a node, according to embodiments of the present technology. The process may include, for example, receiving grid status information including a project status of a portion of a project being executed by a node in the communications grid, as described in operation 502. For example, a control node (e.g., a backup control node connected to a primary control node and a worker node on a communications grid) may receive grid status information, where the grid status information includes a project status of the primary control node or a project status of the worker node. The project status of the primary control node and the project status of the worker node may include a status of one or more portions of a project being executed by the primary and worker nodes in the communications grid. The process may also include storing the grid status information, as described in operation 504. For example, a control node (e.g., a backup control node) may store the received grid status information locally within the control node. Alternatively, the grid status information may be sent to another device for storage where the control node may have access to the information.

The process may also include receiving a failure communication corresponding to a node in the communications grid in operation 506. For example, a node may receive a failure communication including an indication that the primary control node has failed, prompting a backup control node to take over for the primary control node. In an alternative embodiment, a node may receive a failure that a worker node has failed, prompting a control node to reassign the work being performed by the worker node. The process may also include reassigning a node or a portion of the project being executed by the failed node, as described in operation 508. For example, a control node may designate the backup control node as a new primary control node based on the failure communication upon receiving the failure communication. If the failed node is a worker node, a control node may identify a project status of the failed worker node using the snapshot of the communications grid, where the project status of the failed worker node includes a status of a portion of the project being executed by the failed worker node at the failure time.

The process may also include receiving updated grid status information based on the reassignment, as described in operation 510, and transmitting a set of instructions based on the updated grid status information to one or more nodes in the communications grid, as described in operation 512. The updated grid status information may include an updated project status of the primary control node or an updated project status of the worker node. The updated information may be transmitted to the other nodes in the grid to update their stale stored information.

Figure 6:
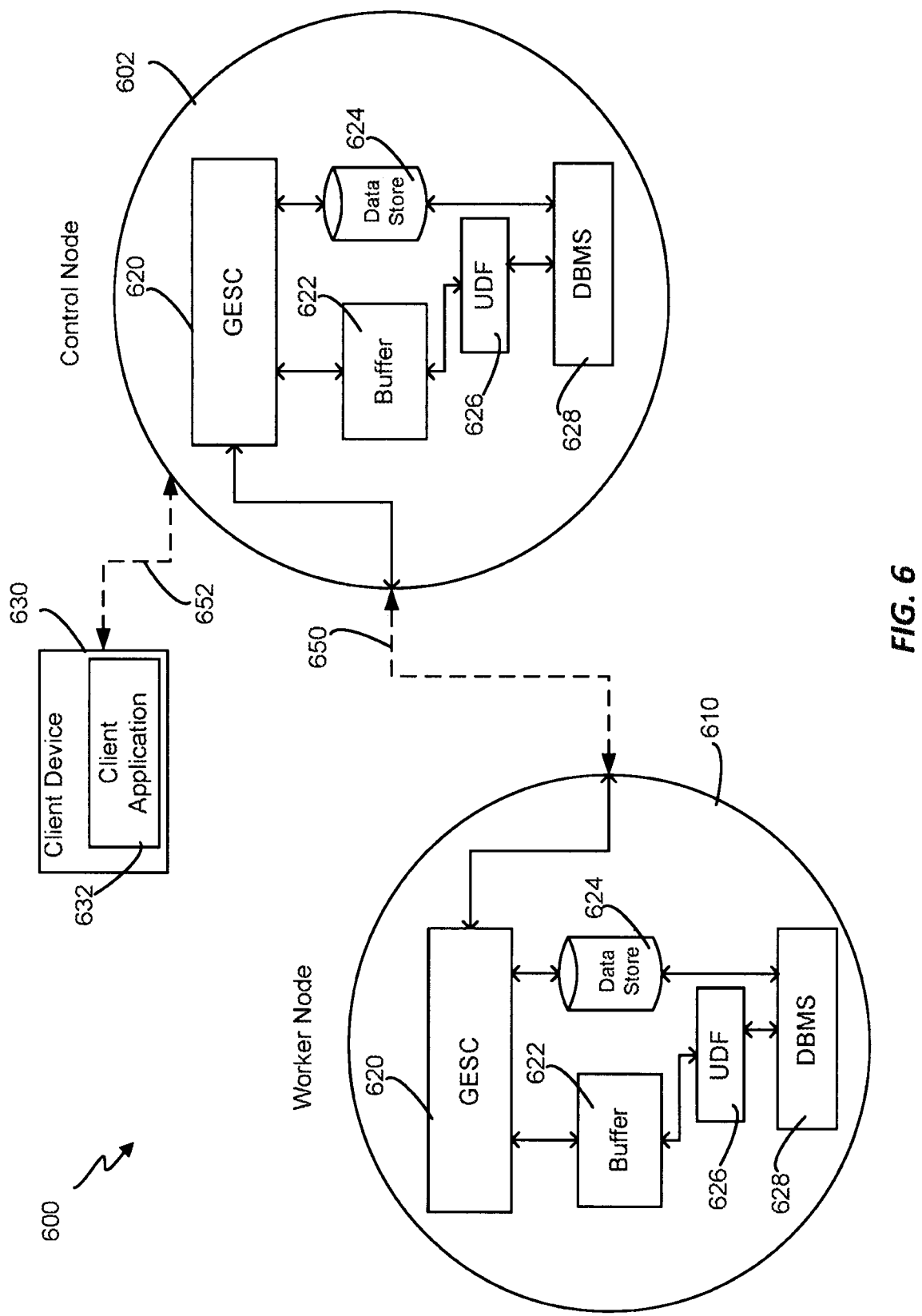
FIG. 6 illustrates a portion of a communications grid computing system including a control node and a worker node, according to at least one embodiment of the present technology.

FIG. 6 illustrates a portion of a communications grid computing system 600 including a control node and a worker node, according to embodiments of the present technology. Communications grid 600 computing system includes one control node (control node 602) and one worker node (worker node 610) for purposes of illustration, but may include more worker and/or control nodes. The control node 602 is communicatively connected to worker node 610 via communication path 650. Therefore, control node 602 may transmit information (e.g., related to the communications grid or notifications), to and receive information from worker node 610 via path 650.

Similar to in FIG. 4, communications grid computing system (or just "communications grid") 600 includes data processing nodes (control node 602 and worker node 610). Nodes 602 and 610 include multi-core data processors. Each node 602 and 610 includes a grid-enabled software component (GESC) 620 that executes on the data processor associated with that node and interfaces with buffer memory 622 also associated with that node. Each node 602 and 610 includes a database management software (DBMS) 628 that executes on a database server (not shown) at control node 602 and on a database server (not shown) at worker node 610.

Each node also includes a data store 624. Data stores 624, similar to network-attached data stores 110 in FIG. 1 and data stores 235 in FIG. 2, are used to store data to be processed by the nodes in the computing environment. Data stores 624 may also store any intermediate or final data generated by the computing system after being processed, for example in non-volatile memory. However in certain embodiments, the configuration of the grid computing environment allows its operations to be performed such that intermediate and final data results can be stored solely in volatile memory (e.g., RAM), without a requirement that intermediate or final data results be stored to non-volatile types of memory. Storing such data in volatile memory may be useful in certain situations, such as when the grid receives queries (e.g., ad hoc) from a client and when responses, which are generated by processing large amounts of data, need to be generated quickly or on-the-fly. In such a situation, the grid may be configured to retain the data within memory so that responses can be generated at different levels of detail and so that a client may interactively query against this information.

Each node also includes a user-defined function (UDF) 626. The UDF provides a mechanism for the DBMS 628 to transfer data to or receive data from the database stored in the data stores 624 that are managed by the DBMS. For example, UDF 626 can be invoked by the DBMS to provide data to the GESC for processing. The UDF 626 may establish a socket connection (not shown) with the GESC to transfer the data. Alternatively, the UDF 626 can transfer data to the GESC by writing data to shared memory accessible by both the UDF and the GESC.

The GESC 620 at the nodes 602 and 610 may be connected via a network, such as network 108 shown in FIG. 1. Therefore, nodes 602 and 610 can communicate with each other via the network using a predetermined communication protocol such as, for example, the Message Passing Interface (MPI). Each GESC 620 can engage in point-to-point communication with the GESC at another node or in collective communication with multiple GESCs via the network. The GESC 620 at each node may contain identical (or nearly identical) software instructions. Each node may be capable of operating as either a control node or a worker node. The GESC at the control node 602 can communicate, over a communication path 652, with a client device 630. More specifically, control node 602 may communicate with client application 632 hosted by the client device 630 to receive queries and to respond to those queries after processing large amounts of data.

DBMS 628 may control the creation, maintenance, and use of database or data structure (not shown) within a nodes 602 or 610. The database may organize data stored in data stores 624. The DBMS 628 at control node 602 may accept requests for data and transfer the appropriate data for the request. With such a process, collections of data may be distributed across multiple physical locations. In this example, each node 602 and 610 stores a portion of the total data managed by the management system in its associated data store 624.

Furthermore, the DBMS may be responsible for protecting against data loss using replication techniques. Replication includes providing a backup copy of data stored on one node on one or more other nodes. Therefore, if one node fails, the data from the failed node can be recovered from a replicated copy residing at another node. However, as described herein with respect to FIG. 4, data or status information for each node in the communications grid may also be shared with each node on the grid.

Figure 7:
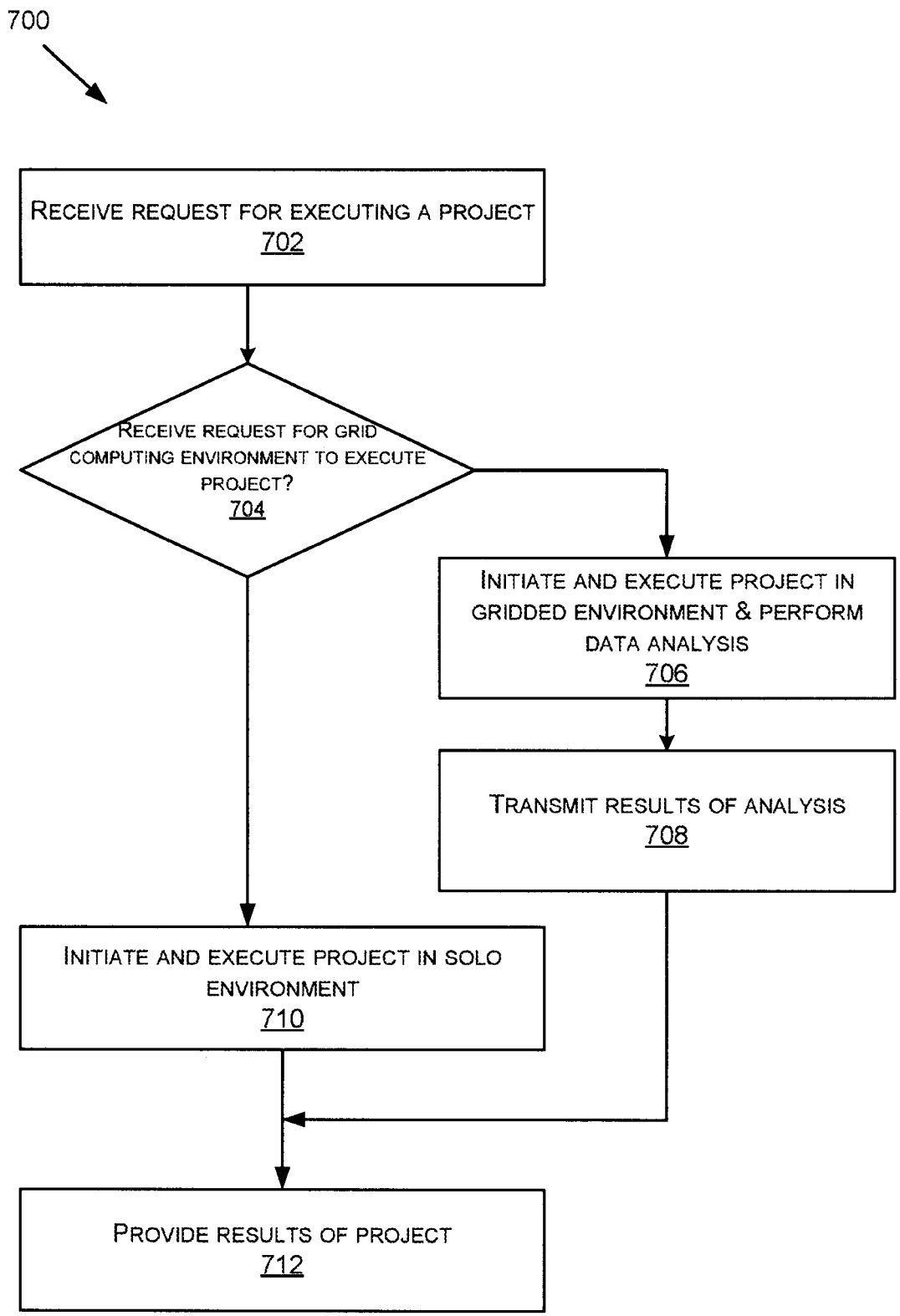
FIG. 7 illustrates a flow chart showing an example process for executing a data analysis or processing project, according to at least one embodiment of the present technology.

FIG. 7 illustrates a flow chart 700 showing an example method for executing a project within a grid computing system, according to embodiments of the present technology. As described with respect to FIG. 6, the GESC at the control node may transmit data with a client device (e.g., client device 630) to receive queries for executing a project and to respond to those queries after large amounts of data have been processed. The query may be transmitted to the control node, where the query may include a request for executing a project, as described in operation 702. The query can contain instructions on the type of data analysis to be performed in the project and whether the project should be executed using the grid-based computing environment, as shown in operation 704.

To initiate the project, the control node may determine if the query requests use of the grid-based computing environment to execute the project. If the determination is no, then the control node initiates execution of the project in a solo environment (e.g., at the control node), as described in operation 710. If the determination is yes, the control node may initiate execution of the project in the grid-based computing environment, as described in operation 706. In such a situation, the request may include a requested configuration of the grid. For example, the request may include a number of control nodes and a number of worker nodes to be used in the grid when executing the project. After the project has been completed, the control node may transmit results of the analysis yielded by the grid, as described in operation 708. Whether the project is executed in a solo or grid-based environment, the control node provides the results of the project in operation 712.

As noted with respect to FIG. 2, the computing environments described herein may collect data (e.g., as received from network devices, such as sensors, such as network devices 204-209 in FIG. 2, and client devices or other sources) to be processed as part of a data analytics project, and data may be received in real time as part of a streaming analytics environment (e.g., ESP). Data may be collected using a variety of sources as communicated via different kinds of networks or locally, such as on a real-time streaming basis. For example, network devices may receive data periodically from network device sensors as the sensors continuously sense, monitor and track changes in their environments. More specifically, an increasing number of distributed applications develop or produce continuously flowing data from distributed sources by applying queries to the data before distributing the data to geographically distributed recipients. An event stream processing engine (ESPE) may continuously apply the queries to the data as it is received and determines which entities should receive the data. Client or other devices may also subscribe to the ESPE or other devices processing ESP data so that they can receive data after processing, based on for example the entities determined by the processing engine. For example, client devices 230 in FIG. 2 may subscribe to the ESPE in computing environment 214. In another example, event subscription devices 1024a-c, described further with respect to FIG. 10, may also subscribe to the ESPE. The ESPE may determine or define how input data or event streams from network devices or other publishers (e.g., network devices 204-209 in FIG. 2) are transformed into meaningful output data to be consumed by subscribers, such as for example client devices 230 in FIG. 2.

FIG. 8 illustrates a block diagram including components of an Event Stream Processing Engine (ESPE), according to embodiments of the present technology. ESPE 800 may include one or more projects 802. A project may be described as a second-level container in an engine model managed by ESPE 800 where a thread pool size for the project may be defined by a user. Each project of the one or more projects 802 may include one or more continuous queries 804 that contain data flows, which are data transformations of incoming event streams. The one or more continuous queries 804 may include one or more source windows 806 and one or more derived windows 808.

The ESPE may receive streaming data over a period of time related to certain events, such as events or other data sensed by one or more network devices. The ESPE may perform operations associated with processing data created by the one or more devices. For example, the ESPE may receive data from the one or more network devices 204-209 shown in FIG. 2. As noted, the network devices may include sensors that sense different aspects of their environments, and may collect data over time based on those sensed observations. For example, the ESPE may be implemented within one or more of machines 220 and 240 shown in FIG. 2. The ESPE may be implemented within such a machine by an ESP application. An ESP application may embed an ESPE with its own dedicated thread pool or pools into its application space where the main application thread can do application-specific work and the ESPE processes event streams at least by creating an instance of a model into processing objects.

The engine container is the top-level container in a model that manages the resources of the one or more projects 802. In an illustrative embodiment, for example, there may be only one ESPE 800 for each instance of the ESP application, and ESPE 800 may have a unique engine name. Additionally, the one or more projects 802 may each have unique project names, and each query may have a unique continuous query name and begin with a uniquely named source window of the one or more source windows 806. ESPE 800 may or may not be persistent.

Continuous query modeling involves defining directed graphs of windows for event stream manipulation and transformation. A window in the context of event stream manipulation and transformation is a processing node in an event stream processing model. A window in a continuous query can perform aggregations, computations, pattern-matching, and other operations on data flowing through the window. A continuous query may be described as a directed graph of source, relational, pattern matching, and procedural windows. The one or more source windows 806 and the one or more derived windows 808 represent continuously executing queries that generate updates to a query result set as new event blocks stream through ESPE 800. A directed graph, for example, is a set of nodes connected by edges, where the edges have a direction associated with them.

An event object may be described as a packet of data accessible as a collection of fields, with at least one of the fields defined as a key or unique identifier (ID). The event object may be created using a variety of formats including binary, alphanumeric, XML, etc. Each event object may include one or more fields designated as a primary identifier (ID) for the event so ESPE 800 can support operation codes (opcodes) for events including insert, update, upsert, and delete. Upsert opcodes update the event if the key field already exists; otherwise, the event is inserted. For illustration, an event object may be a packed binary representation of a set of field values and include both metadata and field data associated with an event. The metadata may include an opcode indicating if the event represents an insert, update, delete, or upsert, a set of flags indicating if the event is a normal, partial-update, or a retention generated event from retention policy management, and a set of microsecond timestamps that can be used for latency measurements.

An event block object may be described as a grouping or package of event objects. An event stream may be described as a flow of event block objects. A continuous query of the one or more continuous queries 804 transforms a source event stream made up of streaming event block objects published into ESPE 800 into one or more output event streams using the one or more source windows 806 and the one or more derived windows 808. A continuous query can also be thought of as data flow modeling.

The one or more source windows 806 are at the top of the directed graph and have no windows feeding into them. Event streams are published into the one or more source windows 806, and from there, the event streams may be directed to the next set of connected windows as defined by the directed graph. The one or more derived windows 808 are all instantiated windows that are not source windows and that have other windows streaming events into them. The one or more derived windows 808 may perform computations or transformations on the incoming event streams. The one or more derived windows 808 transform event streams based on the window type (that is operators such as join, filter, compute, aggregate, copy, pattern match, procedural, union, etc.) and window settings. As event streams are published into ESPE 800, they are continuously queried, and the resulting sets of derived windows in these queries are continuously updated.

FIG. 9 illustrates a flow chart showing an example process including operations performed by an event stream processing engine, according to some embodiments of the present technology. As noted, the ESPE 800 (or an associated ESP application) defines how input event streams are transformed into meaningful output event streams. More specifically, the ESP application may define how input event streams from publishers (e.g., network devices providing sensed data) are transformed into meaningful output event streams consumed by subscribers (e.g., a data analytics project being executed by a machine or set of machines).

Within the application, a user may interact with one or more user interface windows presented to the user in a display under control of the ESPE independently or through a browser application in an order selectable by the user. For example, a user may execute an ESP application, which causes presentation of a first user interface window, which may include a plurality of menus and selectors such as drop down menus, buttons, text boxes, hyperlinks, etc. associated with the ESP application as understood by a person of skill in the art. As further understood by a person of skill in the art, various operations may be performed in parallel, for example, using a plurality of threads.

At operation 900, an ESP application may define and start an ESPE, thereby instantiating an ESPE at a device, such as machine 220 and/or 240. In an operation 902, the engine container is created. For illustration, ESPE 800 may be instantiated using a function call that specifies the engine container as a manager for the model.

In an operation 904, the one or more continuous queries 804 are instantiated by ESPE 800 as a model. The one or more continuous queries 804 may be instantiated with a dedicated thread pool or pools that generate updates as new events stream through ESPE 800. For illustration, the one or more continuous queries 804 may be created to model business processing logic within ESPE 800, to predict events within ESPE 800, to model a physical system within ESPE 800, to predict the physical system state within ESPE 800, etc. For example, as noted, ESPE 800 may be used to support sensor data monitoring and management (e.g., sensing may include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, or electrical current, etc.). ESPE 800 may analyze and process events in motion or "event streams." Instead of storing data and running queries against the stored data, ESPE 800 may store queries and stream data through them to allow continuous analysis of data as it is received. The one or more source windows 806 and the one or more derived windows 808 may be created based on the relational, pattern matching, and procedural algorithms that transform the input event streams into the output event streams to model, simulate, score, test, predict, etc. based on the continuous query model defined and application to the streamed data.

In an operation 906, a publish/subscribe (pub/sub) capability is initialized for ESPE 800. In an illustrative embodiment, a pub/sub capability is initialized for each project of the one or more projects 802. To initialize and enable pub/sub capability for ESPE 800, a port number may be provided. Pub/sub clients can use a host name of an ESP device running the ESPE and the port number to establish pub/sub connections to ESPE 800.

FIG. 10 illustrates an ESP system 1000 interfacing between publishing device 1022 and event subscribing devices 1024*a-c*, according to embodiments of the present technology. ESP system 1000 may include ESP device or subsystem 1001, event publishing device 1022, an event subscribing device A 1024*a*, an event subscribing device B 1024*b*, and an event subscribing device C 1024*c*. Input event streams are output to ESP device 1001 by publishing device 1022. In alternative embodiments, the input event streams may be created by a plurality of publishing devices. The plurality of publishing devices further may publish event streams to other ESP devices. The one or more continuous queries instantiated by ESPE 800 may analyze and process the input event streams to form output event streams output to event subscribing device A 1024*a*, event subscribing device B 1024*b*, and event subscribing device C 1024*c*. ESP system 1000 may include a greater or a fewer number of event subscribing devices of event subscribing devices.

Publish-subscribe is a message-oriented interaction paradigm based on indirect addressing. Processed data recipients specify their interest in receiving information from ESPE 800 by subscribing to specific classes of events, while information sources publish events to ESPE 800 without directly addressing the receiving parties. ESPE 800 coordinates the interactions and processes the data. In some cases, the data source receives confirmation that the published information has been received by a data recipient.

A publish/subscribe API may be described as a library that enables an event publisher, such as publishing device 1022, to publish event streams into ESPE 800 or an event subscriber, such as event subscribing device A 1024a, event subscribing device B 1024b, and event subscribing device C 1024c, to subscribe to event streams from ESPE 800. For illustration, one or more publish/subscribe APIs may be defined. Using the publish/subscribe API, an event publishing application may publish event streams into a running event stream processor project source window of ESPE 800, and the event subscription application may subscribe to an event stream processor project source window of ESPE 800.

The publish/subscribe API provides cross-platform connectivity and endianness compatibility between ESP application and other networked applications, such as event publishing applications instantiated at publishing device 1022, and event subscription applications instantiated at one or more of event subscribing device A 1024a, event subscribing device B 1024b, and event subscribing device C 1024c.

Referring back to FIG. 9, operation 906 initializes the publish/subscribe capability of ESPE 800. In an operation 908, the one or more projects 802 are started. The one or more started projects may run in the background on an ESP device. In an operation 910, an event block object is received from one or more computing device of the event publishing device 1022.

ESP subsystem 1001 may include a publishing client 1002, ESPE 800, a subscribing client A 1004, a subscribing client B 1006, and a subscribing client C 1008. Publishing client 1002 may be started by an event publishing application executing at publishing device 1022 using the publish/subscribe API. Subscribing client A 1004 may be started by an event subscription application A, executing at event subscribing device A 1024a using the publish/subscribe API. Subscribing client B 1006 may be started by an event subscription application B executing at event subscribing device B 1024b using the publish/subscribe API. Subscribing client C 1008 may be started by an event subscription application C executing at event subscribing device C 1024c using the publish/subscribe API.

An event block object containing one or more event objects is injected into a source window of the one or more source windows 806 from an instance of an event publishing application on event publishing device 1022. The event block object may be generated, for example, by the event publishing application and may be received by publishing client 1002. A unique ID may be maintained as the event block object is passed between the one or more source windows 806 and/or the one or more derived windows 808 of ESPE 800, and to subscribing client A 1004, subscribing client B 1006, and subscribing client C 1008 and to event subscription device A 1024a, event subscription device B 1024b, and event subscription device C 1024c. Publishing client 1002 may further generate and include a unique embedded transaction ID in the event block object as the event block object is processed by a continuous query, as well as the unique ID that publishing device 1022 assigned to the event block object.

In an operation 912, the event block object is processed through the one or more continuous queries 804. In an operation 914, the processed event block object is output to one or more computing devices of the event subscribing devices 1024a-c. For example, subscribing client A 1004, subscribing client B 1006, and subscribing client C 1008 may send the received event block object to event subscription device A 1024a, event subscription device B 1024b, and event subscription device C 1024c, respectively.

ESPE 800 maintains the event block containership aspect of the received event blocks from when the event block is published into a source window and works its way through the directed graph defined by the one or more continuous queries 804 with the various event translations before being output to subscribers. Subscribers can correlate a group of subscribed events back to a group of published events by comparing the unique ID of the event block object that a publisher, such as publishing device 1022, attached to the event block object with the event block ID received by the subscriber.

In an operation 916, a determination is made concerning whether or not processing is stopped. If processing is not stopped, processing continues in operation 910 to continue receiving the one or more event streams containing event block objects from the, for example, one or more network devices. If processing is stopped, processing continues in an operation 918. In operation 918, the started projects are stopped. In operation 920, the ESPE is shutdown.

As noted, in some embodiments, big data is processed for an analytics project after the data is received and stored. In other embodiments, distributed applications process continuously flowing data in real-time from distributed sources by applying queries to the data before distributing the data to geographically distributed recipients. As noted, an event stream processing engine (ESPE) may continuously apply the queries to the data as it is received and determines which entities receive the processed data. This allows for large amounts of data being received and/or collected in a variety of environments to be processed and distributed in real time. For example, as shown with respect to FIG. 2, data may be collected from network devices that may include devices within the internet of things, such as devices within a home automation network. However, such data may be collected from a variety of different resources in a variety of different environments. In any such situation, embodiments of the present technology allow for real-time processing of such data.

Aspects of the current disclosure provide technical solutions to technical problems, such as computing problems that arise when an ESP device fails which results in a complete service interruption and potentially significant data loss. The data loss can be catastrophic when the streamed data is supporting mission critical operations such as those in support of an ongoing manufacturing or drilling operation. An embodiment of an ESP system achieves a rapid and seamless failover of ESPE running at the plurality of ESP devices without service interruption or data loss, thus significantly improving the reliability of an operational system that relies on the live or real-time processing of the data streams. The event publishing systems, the event subscribing systems, and each ESPE not executing at a failed ESP device are not aware of or effected by the failed ESP device. The ESP system may include thousands of event publishing systems and event subscribing systems. The ESP system keeps the failover logic and awareness within the boundaries of out-messaging network connector and out-messaging network device.

In one example embodiment, a system is provided to support a failover when event stream processing (ESP) event blocks. The system includes, but is not limited to, an out-messaging network device and a computing device. The computing device includes, but is not limited to, a processor and a computer-readable medium operably coupled to the processor. The processor is configured to execute an ESP engine (ESPE). The computer-readable medium has instructions stored thereon that, when executed by the processor, cause the computing device to support the failover. An event block object is received from the ESPE that includes a unique identifier. A first status of the computing device as active or standby is determined. When the first status is active, a second status of the computing device as newly active or not newly active is determined. Newly active is determined when the computing device is switched from a standby status to an active status. When the second status is newly active, a last published event block object identifier that uniquely identifies a last published event block object is determined. A next event block object is selected from a non-transitory computer-readable medium accessible by the computing device. The next event block object has an event block object identifier that is greater than the determined last published event block object identifier. The selected next event block object is published to an out-messaging network device. When the second status of the computing device is not newly active, the received event block object is published to the out-messaging network device. When the first status of the computing device is standby, the received event block object is stored in the non-transitory computer-readable medium.

Figure 11:
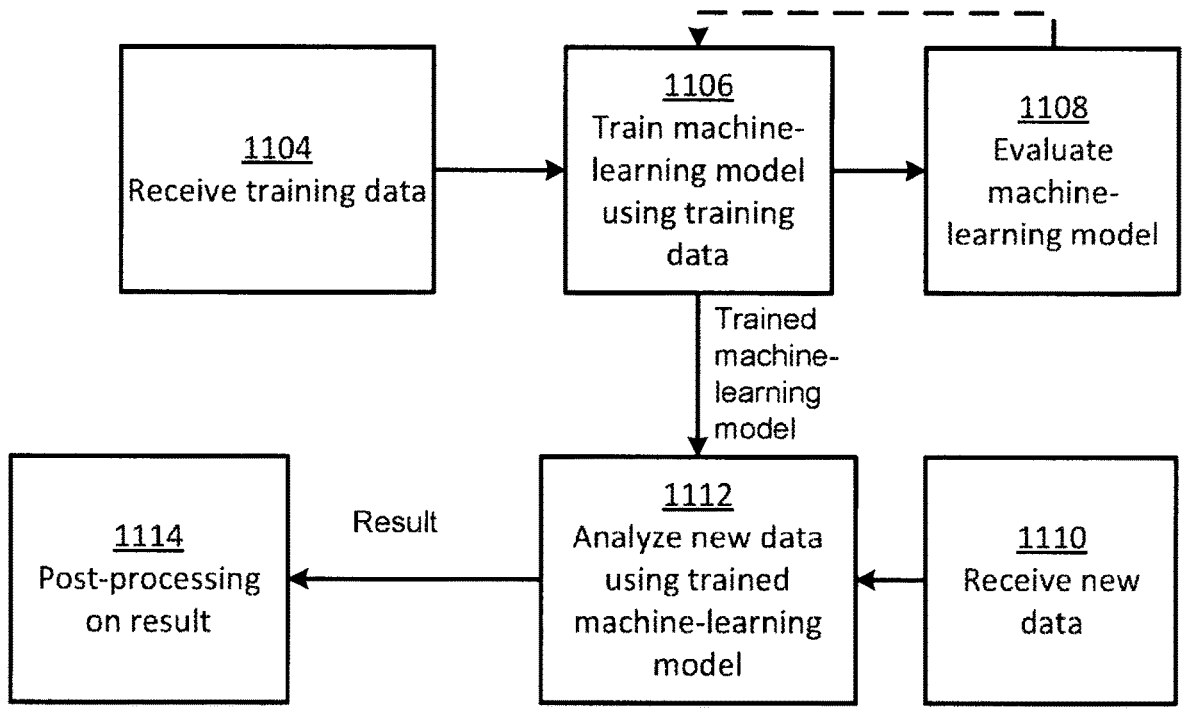
FIG. 11 illustrates a flow chart of an example of a process for generating and using a machine-learning model according to at least one embodiment of the present technology.

FIG. 11 is a flow chart of an example of a process for generating and using a machine-learning model according to some aspects. Machine learning is a branch of artificial intelligence that relates to mathematical models that can learn from, categorize, and make predictions about data. Such mathematical models, which can be referred to as machine-learning models, can classify input data among two or more classes; cluster input data among two or more groups; predict a result based on input data; identify patterns or trends in input data; identify a distribution of input data in a space; or any combination of these. Examples of machine-learning models can include (i) neural networks; (ii) decision trees, such as classification trees and regression trees; (iii) classifiers, such as Naïve bias classifiers, logistic regression classifiers, ridge regression classifiers, random forest classifiers, least absolute shrinkage and selector (LASSO) classifiers, and support vector machines; (iv) clusterers, such as k-means clusterers, mean-shift clusterers, and spectral clusterers; (v) factorizers, such as factorization machines, principal component analyzers and kernel principal component analyzers; and (vi) ensembles or other combinations of machine-learning models. In some examples, neural networks can include deep neural networks, feed-forward neural networks, recurrent neural networks, convolutional neural networks, radial basis function (RBF) neural networks, echo state neural networks, long short-term memory neural networks, bi-directional recurrent neural networks, gated neural networks, hierarchical recurrent neural networks, stochastic neural networks, modular neural networks, spiking neural networks, dynamic neural networks, cascading neural networks, neuro-fuzzy neural networks, or any combination of these.

Different machine-learning models may be used interchangeably to perform a task. Examples of tasks that can be performed at least partially using machine-learning models include various types of scoring; bioinformatics; cheminformatics; software engineering; fraud detection; customer segmentation; generating online recommendations; adaptive websites; determining customer lifetime value; search engines; placing advertisements in real time or near real time; classifying DNA sequences; affective computing; performing natural language processing and understanding; object recognition and computer vision; robotic locomotion; playing games; optimization and metaheuristics; detecting network intrusions; medical diagnosis and monitoring; or predicting when an asset, such as a machine, will need maintenance.

Any number and combination of tools can be used to create machine-learning models. Examples of tools for creating and managing machine-learning models can include SAS® Enterprise Miner, SAS® Rapid Predictive Modeler, and SAS® Model Manager, SAS Cloud Analytic Services (CAS)®, SAS Viya® of all which are by SAS Institute Inc. of Cary, N.C.

Machine-learning models can be constructed through an at least partially automated (e.g., with little or no human involvement) process called training. During training, input data can be iteratively supplied to a machine-learning model to enable the machine-learning model to identify patterns related to the input data or to identify relationships between the input data and output data. With training, the machine-learning model can be transformed from an untrained state to a trained state. Input data can be split into one or more training sets and one or more validation sets, and the training process may be repeated multiple times. The splitting may follow a k-fold cross-validation rule, a leave-one-out-rule, a leave-p-out rule, or a holdout rule. An overview of training and using a machine-learning model is described below with respect to the flow chart of FIG. 11.

In block 1104, training data is received. In some examples, the training data is received from a remote database or a local database, constructed from various subsets of data, or input by a user. The training data can be used in its raw form for training a machine-learning model or pre-processed into another form, which can then be used for training the machine-learning model. For example, the raw form of the training data can be smoothed, truncated, aggregated, clustered, or otherwise manipulated into another form, which can then be used for training the machine-learning model.

In block 1106, a machine-learning model is trained using the training data. The machine-learning model can be trained in a supervised, unsupervised, or semi-supervised manner. In supervised training, each input in the training data is correlated to a desired output. This desired output may be a scalar, a vector, or a different type of data structure such as text or an image. This may enable the machine-learning model to learn a mapping between the inputs and desired outputs. In unsupervised training, the training data includes inputs, but not desired outputs, so that the machine-learning model has to find structure in the inputs on its own. In semi-supervised training, only some of the inputs in the training data are correlated to desired outputs.

In block 1108, the machine-learning model is evaluated. For example, an evaluation dataset can be obtained, for example, via user input or from a database. The evaluation dataset can include inputs correlated to desired outputs. The inputs can be provided to the machine-learning model and the outputs from the machine-learning model can be compared to the desired outputs. If the outputs from the machine-learning model closely correspond with the desired outputs, the machine-learning model may have a high degree of accuracy. For example, if 90% or more of the outputs from the machine-learning model are the same as the desired outputs in the evaluation dataset, the machine-learning model may have a high degree of accuracy. Otherwise, the machine-learning model may have a low degree of accuracy. The 90% number is an example only. A realistic and desirable accuracy percentage is dependent on the problem and the data.

In some examples, if the machine-learning model has an inadequate degree of accuracy for a particular task, the process can return to block 1106, where the machine-learning model can be further trained using additional training data or otherwise modified to improve accuracy. If the machine-learning model has an adequate degree of accuracy for the particular task, the process can continue to block 1110.

In block 1110, new data is received. In some examples, the new data is received from a remote database or a local database, constructed from various subsets of data, or input by a user. The new data may be unknown to the machine-learning model. For example, the machine-learning model may not have previously processed or analyzed the new data.

In block 1112, the trained machine-learning model is used to analyze the new data and provide a result. For example, the new data can be provided as input to the trained machine-learning model. The trained machine-learning model can analyze the new data and provide a result that includes a classification of the new data into a particular class, a clustering of the new data into a particular group, a prediction based on the new data, or any combination of these.

In block 1114, the result is post-processed. For example, the result can be added to, multiplied with, or otherwise combined with other data as part of a job. As another example, the result can be transformed from a first format, such as a time series format, into another format, such as a count series format. Any number and combination of operations can be performed on the result during post-processing.

Figure 12:
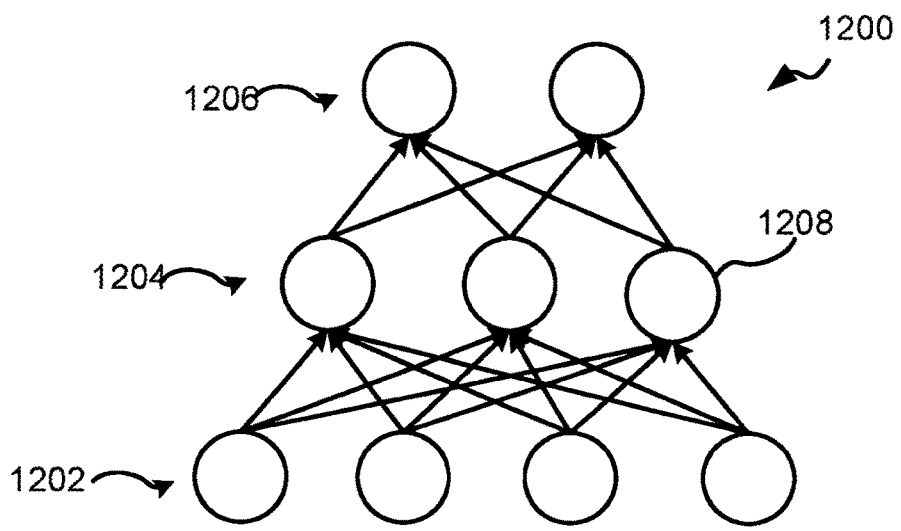
FIG. 12 illustrates an example of a machine-learning model as a neural network according to at least one embodiment of the present technology.

A more specific example of a machine-learning model is the neural network 1200 shown in FIG. 12. The neural network 1200 is represented as multiple layers of interconnected neurons, such as neuron 1208, that can exchange data between one another. The layers include an input layer 1202 for receiving input data, a hidden layer 1204, and an output layer 1206 for providing a result. The hidden layer 1204 is referred to as hidden because it may not be directly observable or have its input directly accessible during the normal functioning of the neural network 1200. Although the neural network 1200 is shown as having a specific number of layers and neurons for exemplary purposes, the neural network 1200 can have any number and combination of layers, and each layer can have any number and combination of neurons.

The neurons and connections between the neurons can have numeric weights, which can be tuned during training. For example, training data can be provided to the input layer 1202 of the neural network 1200, and the neural network 1200 can use the training data to tune one or more numeric weights of the neural network 1200. In some examples, the neural network 1200 can be trained using backpropagation. Backpropagation can include determining a gradient of a particular numeric weight based on a difference between an actual output of the neural network 1200 and a desired output of the neural network 1200. Based on the gradient, one or more numeric weights of the neural network 1200 can be updated to reduce the difference, thereby increasing the accuracy of the neural network 1200. This process can be repeated multiple times to train the neural network 1200. For example, this process can be repeated hundreds or thousands of times to train the neural network 1200.

In some examples, the neural network 1200 is a feed-forward neural network. In a feed-forward neural network, every neuron only propagates an output value to a subsequent layer of the neural network 1200. For example, data may only move one direction (forward) from one neuron to the next neuron in a feed-forward neural network.

In other examples, the neural network 1200 is a recurrent neural network. A recurrent neural network can include one or more feedback loops, allowing data to propagate in both forward and backward through the neural network 1200. This can allow for information to persist within the recurrent neural network. For example, a recurrent neural network can determine an output based at least partially on information that the recurrent neural network has seen before, giving the recurrent neural network the ability to use previous input to inform the output.

In some examples, the neural network 1200 operates by receiving a vector of numbers from one layer; transforming the vector of numbers into a new vector of numbers using a matrix of numeric weights, a nonlinearity, or both; and providing the new vector of numbers to a subsequent layer of the neural network 1200. Each subsequent layer of the neural network 1200 can repeat this process until the neural network 1200 outputs a final result at the output layer 1206. For example, the neural network 1200 can receive a vector of numbers as an input at the input layer 1202. The neural network 1200 can multiply the vector of numbers by a matrix of numeric weights to determine a weighted vector. The matrix of numeric weights can be tuned during the training of the neural network 1200. The neural network 1200 can transform the weighted vector using a nonlinearity, such as a sigmoid tangent or the hyperbolic tangent. In some examples, the nonlinearity can include a rectified linear unit, which can be expressed using the following equation:

$$y = \max(x, 0)$$

where y is the output and x is an input value from the weighted vector. The transformed output can be supplied to a subsequent layer, such as the hidden layer 1204, of the neural network 1200. The subsequent layer of the neural network 1200 can receive the transformed output, multiply the transformed output by a matrix of numeric weights and a nonlinearity, and provide the result to yet another layer of the neural network 1200. This process continues until the neural network 1200 outputs a final result at the output layer 1206.

Other examples of the present disclosure may include any number and combination of machine-learning models having any number and combination of characteristics. The machine-learning model(s) can be trained in a supervised, semi-supervised, or unsupervised manner, or any combination of these. The machine-learning model(s) can be implemented using a single computing device or multiple computing devices, such as the communications grid computing system 400 discussed above.

Implementing some examples of the present disclosure at least in part by using machine-learning models can reduce the total number of processing iterations, time, memory, electrical power, or any combination of these consumed by a computing device when analyzing data. For example, a neural network may more readily identify patterns in data than other approaches. This may enable the neural network to analyze the data using fewer processing cycles and less memory than other approaches, while obtaining a similar or greater level of accuracy.

Some machine-learning approaches may be more efficiently and speedily executed and processed with machine-learning specific processors (e.g., not a generic CPU). Such processors may also provide an energy savings when compared to generic CPUs. For example, some of these processors can include a graphical processing unit (GPU), an application-specific integrated circuit (ASIC), a field-programmable gate array (FPGA), an artificial intelligence (AI) accelerator, a neural computing core, a neural computing engine, a neural processing unit, a purpose-built chip architecture for deep learning, and/or some other machine-learning specific processor that implements a machine learning approach or one or more neural networks using semiconductor (e.g., silicon (Si), gallium arsenide (GaAs)) devices. Furthermore, these processors may also be employed in heterogeneous computing architectures with a number of and a variety of different types of cores, engines, nodes, and/or layers to achieve various energy efficiencies, processing speed improvements, data communication speed improvements, and/or data efficiency targets and improvements throughout various parts of the system when compared to a homogeneous computing architecture that employs CPUs for general purpose computing.

Figure 13:
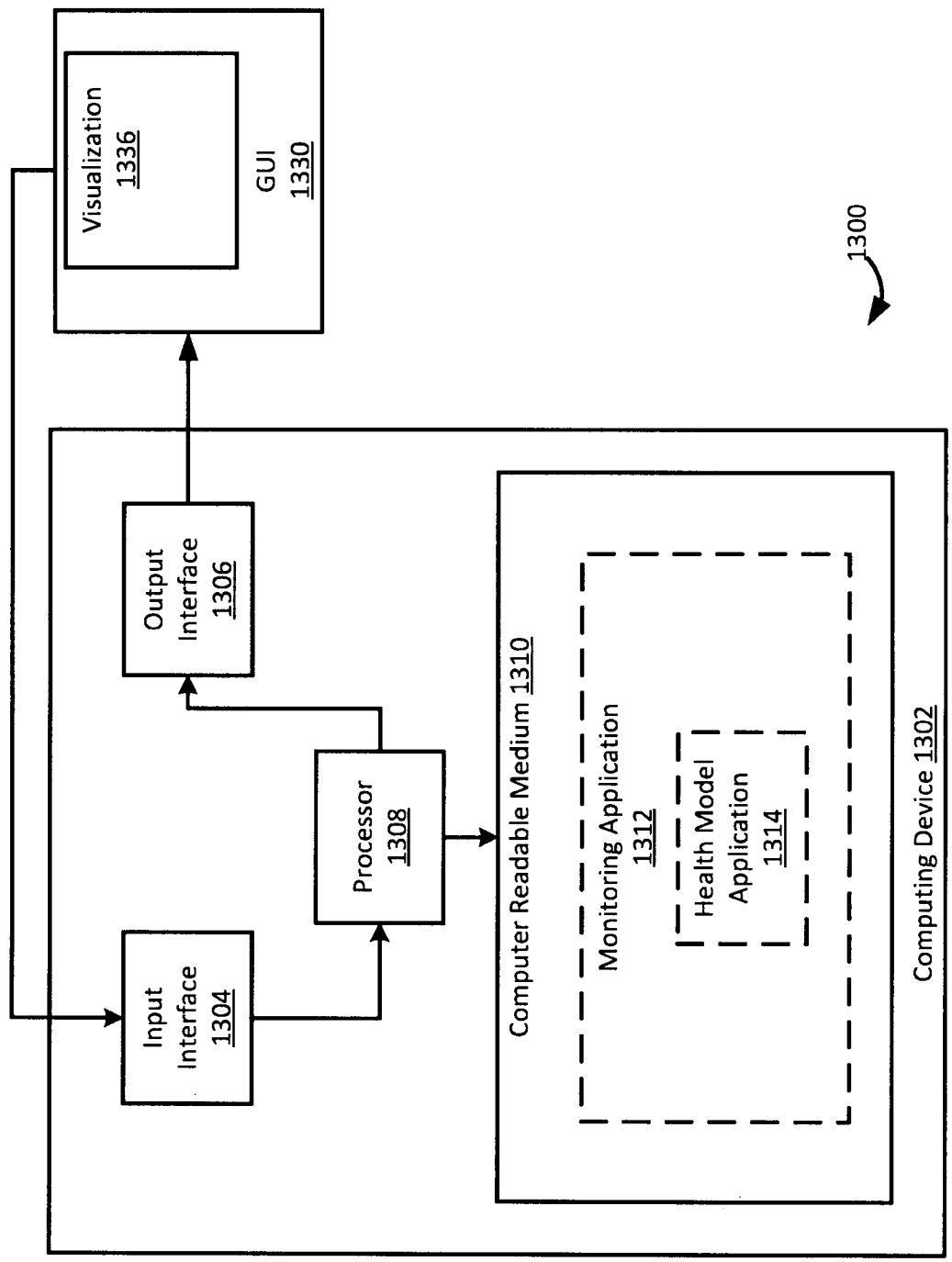
FIG. 13 illustrates a block diagram of a system for monitoring one or more systems according to at least one embodiment of the present technology.

FIG. 13 illustrates a block diagram of a system 1300 for monitoring one or more systems (e.g., systems providing one or more computer models, other systems not shown). System 1300 includes a computing device 1302 and optionally one or more input devices and/or output devices (e.g., a device providing graphical user interface 1330). The system 1300 is configured to exchange information using input interface 1304 and output interface 1306 between devices in the system (e.g., via wired and/or wireless transmission). For example, a network (not shown) can connect one or more devices of system 1300 to one or more other devices of system 1300. Alternatively, or additionally, the system is integrated into one device (e.g., with internal interfaces). For instance, computing device 1302 could be a device with an integrated graphical user interface 1330 (e.g., a laptop, a tablet, a device with a touch screen).

The computing device 1302 has a computer-readable medium 1310 and a processor 1308. In one or more embodiments, computer-readable medium 1310 stores instructions for execution by processor 1308. As an example, computer-readable medium 1310 can store one or more applications implemented in software (e.g., computer-readable and/or computer-executable instructions) stored in computer-readable medium 1310 and accessible by processor 1308 for execution of the instructions.

For example, in one or more embodiments, the computer-readable medium 1310 comprises instructions for one or more monitoring application 1312. The monitoring application 1312 can be used to for monitoring systems (not shown). For instance, the systems could have layers of information or measurements pertaining to the system (e.g., information or measurements arranged or associated in a hierarchy). The monitoring application 1312 can be used to establish a hierarchy or layers pertaining to the monitored system. For example, the hierarchy can have an association between each of multiple measures of a measure level of the hierarchy and one or more intermediate levels of the hierarchy (e.g., a measurement category or analysis type for the monitored system). For example, if the monitored system is a computing system, then analysis could pertain to analysis of the performance of the computing system, analysis of the inputs to the computing system, analysis of the outputs from the computing system, analysis of the users of the computing system, or analysis of other systems interfacing with the monitored computing system. The established hierarchy could have an association between these intermediate levels and the monitored system.

The monitoring application 1312 could be used to monitor the system by generating measurements according to the levels of the established hierarchy and update the visualization responsive to an updated measurement for a measurement in the visualization. For instance, the timing of measurements taken for monitoring could be based, for example, on a schedule, in response to a system change (e.g., exceeding a threshold) and in response to a user request (e.g., to update a visualization). The measurements could be user-defined or pre-configured (e.g., the measurements of the monitored system could pertain to average processing time, percent of utilization, and counts of outputs exceeding a threshold). The measurements could be measured by the monitored system, or another system, and communicated to the monitoring application 1312 (e.g., by sending out alerts). Additionally, or alternatively, the monitoring application 1312 can take measurements itself of the monitored system.

In one or more embodiments, the monitoring application 1312 can be used to generate a visualization 1336 in the graphical user interface 1330 pertaining to the monitored system. For instance, the visualization could be a graphical representation, a diagram, a dynamic representation and/or an interactive representation. For instance, it could be a diagram with symbolic representations of information (e.g., concentric circles representing levels in a hierarchy and colors representing health codes). For instance, FIGS. 16A-16D or FIGS. 23A-23D, described in more detail herein, provide example visualizations. Information represented in the visualization could be dynamically updated and/or the visualization could be interactive in that the user is able to select aspects of the visualization for influencing a monitored system or receiving more information pertaining to a monitored system. Accordingly, embodiments herein may be useful for monitoring systems that may have changing measurements where a visual representation of the changing measurements is useful.

As an example, the monitoring application 1312 could include, or be used as, a health model application 1314 for monitoring one or more models (e.g., health of trained models and/or models being dynamically updated). A generated hierarchy could include an association between one or more intermediate levels (e.g., an intermediate level pertaining to a measurement category or analysis type) and at least one model (e.g., one or more trained models). The health model application 1314 could be used to monitor the one or more models by generating health measurements. A health measurement can correspond to a measure in the hierarchy. A health measurement can indicate a performance of a monitored model according to a measurement category or analysis type associated in the hierarchy with the respective measure. For example, the performance could be an efficacy, metric, or tracking indication performed for measuring an aspect of a model. The visualization 1336 could include a graphical representation of an indication of a health measurement for each of one or more measures of the multiple measures. Additionally, or alternatively, the visualization 1336 could include a graphical representation of associations, in the hierarchy, with the one or more measures of the multiple measures, the measure level of the hierarchy, the intermediate level, and the at least one model (e.g., a trained model).

Computer-readable medium 1310 is an electronic holding place or storage for information so the information can be accessed by processor 1308. Computer-readable medium 1310 can include, but is not limited to, any type of random access memory (RAM), any type of read only memory (ROM), any type of flash memory, etc. such as magnetic storage devices (e.g., hard disk, floppy disk, magnetic strips), optical disks (e.g., compact disc (CD), digital versatile disc (DVD)), smart cards, flash memory devices, etc.

Processor 1308 executes instructions (e.g., stored at the computer-readable medium 1310). The instructions can be carried out by a special purpose computer, logic circuits, or hardware circuits. In one or more embodiments, processor 1308 is implemented in hardware and/or firmware. Processor 1308 executes an instruction, meaning it performs or controls the operations called for by that instruction. The term "execution" is the process of running an application or the carrying out of the operation called for by an instruction. The instructions can be written using one or more programming language, scripting language, assembly language, etc. Processor 1308 in one or more embodiments can retrieve a set of instructions from a permanent memory device and copy the instructions in an executable form to a temporary memory device that is generally some form of RAM, for example. Processor 1308 operably couples with components of computing device 1302 (e.g., input interface 1304, with output interface 1306 and with computer-readable medium 1310) to receive, to send, and to process information. Accordingly, a computing system as referred to herein can include, as for example, computing device 1302 or system 1300.

In one or more embodiments, fewer, different, and additional components can be incorporated into computing device 1302. For instance, in one or more embodiments, there are multiple input devices or computing systems (e.g., one to input different measures pertaining to a monitored system). In the same or different embodiments, there are multiple output devices or computing systems (e.g., one to display the graphical user interface 1330 and one to control a monitored system).

As another example, the same interface supports both input interface 1304 and output interface 1306. For example, a touch screen provides a mechanism for user input and for presentation of output to the user. Alternatively, the input interface 1304 has more than one input interface that uses the same or different interface technology. Alternatively, or additionally, the output interface 1306 has more than one output interface that uses the same or different interface technology.

System 1300 is applicable for monitoring any types of system (e.g., one with updating measurements and/or one with hierarchical associations). For example, the monitored system could be an industry system, and monitoring the industry system could involve monitoring aspects of one or more of a manufactured product, manufacturing equipment, manufacturing model, regulatory approval process, or manufacturing plant. As another example, the monitored system could be a health system for monitoring a patient, a health care device, a health model, or a hospital system. For simplicity, one or more examples herein are described with reference to monitoring a computer model system comprising one or more models without regard to a particular industry. One of ordinary skill in the art will appreciate that the examples could be applied to other systems besides computer model systems (e.g., other processes or systems).

In one or more embodiments, the system 1300 implements a method as described herein (e.g., a method shown in FIGS. 14A and/or FIG. 14B) for monitoring a system. For example, FIG. 14A comprises a method 1400 with an operation 1401 of monitoring a system (e.g., a health model indicating the health of a computing model). The method 1400 comprises an operation 1402 of outputting a visualization in a graphical user interface. When monitoring is done in fragmented systems, it can become error prone, tedious to digest and may not provide an overall or comprehensive picture of model performance across dimensions. For instance, one or more embodiments provide a more centralized approach to visualization of a system. A centralized monitoring approach as described herein is particularly helpful for addressing the increase in utilization and sophistication of risk models, including machine learning models, for decision making.

Figure 14A:
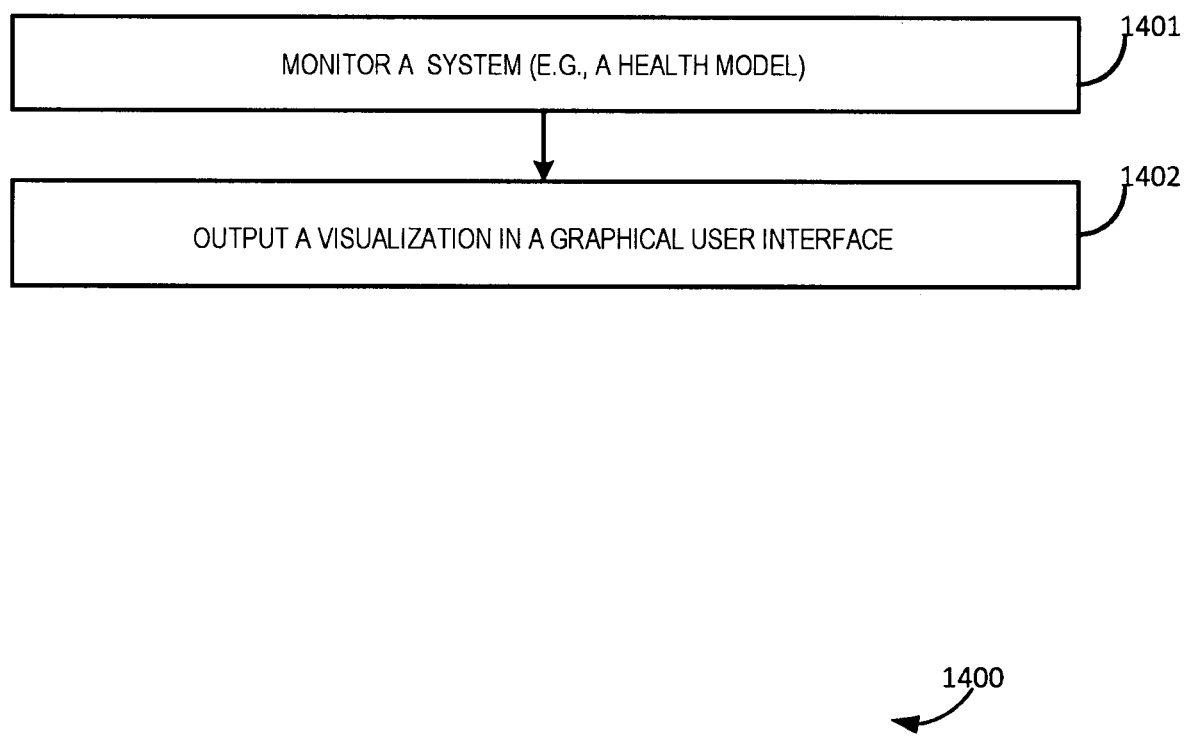
FIGS. 14A-14B illustrates flow diagrams for monitoring one or more systems according to at least one embodiment of the present technology.
Figure 14B:
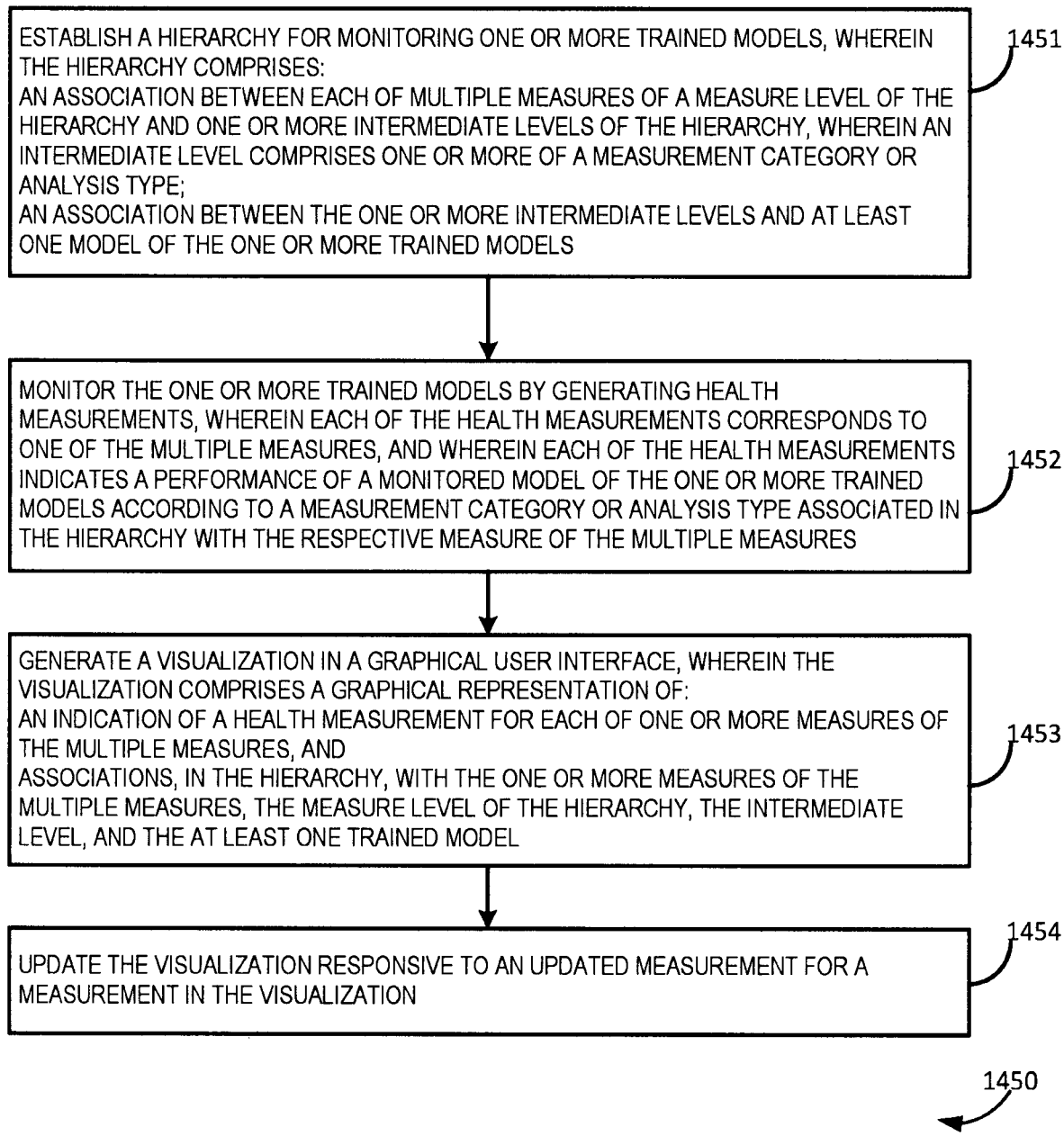

FIG. 14B illustrates a flow diagram of a method 1450 that is a more detailed example of a method implemented according to the method in FIG. 14A for monitoring a computer model. An operation 1451 of method 1450 includes establishing a hierarchy for monitoring one or more trained models. Trained models could be fully trained and put into production or could be partially trained (e.g., as part of a model champion process to select or combine models). In many institutions, model monitoring is an indispensable task typically performed by the model development, model validation or internal audit teams. Model monitoring can be helpful, for instance, in both model training and monitoring (e.g., in pre-deployment and post-deployment phases).

During a pre-deployment phase, monitoring can be used to compare and choose a best models or models among multiple trained models (e.g., developed or generated models that are being evaluated or further trained). During a post-deployment phase, monitoring can be used to keep track of the health of an individual model and to compare multiple models (e.g., champion and challenger models).

Typically monitoring is performed without establishing a hierarchy such as by simply scoring data and applying statistical calculations to the outcomes and maintaining the results in databases or spreadsheets for each monitoring cycle. However, this approach can make it very difficult to visualize or identify root causes. For example, during the COVID-19 pandemic both traditional models and newer machine learning models broke down in a number of industries including retail institutions.

A hierarchy can include an association between each of multiple measures of a measure level of the hierarchy and one or more intermediate levels of the hierarchy. An intermediate level comprises one or more of a measurement category or analysis type. The hierarchy includes an association between the one or more intermediate levels (e.g., a measurement category or analysis type) and at least one trained model of the one or more trained models. The hierarchy can enable a user to more quickly find root causes of issues of monitored systems.

For instance, an operation 1452 of method 1450 includes monitoring the one or more trained models by generating health measurements (e.g., measurements of performance outcomes for a model or measurements of inputs for a model). Each of the health measurements corresponds to one of the multiple measures. Each of the health measurements indicates a performance of a monitored model of the one or more trained models according to a measurement category or analysis type associated in the hierarchy with the respective measure of the multiple measures.

An operation 1453 includes generating a visualization in a graphical user interface (e.g., a visualization shown in FIGS. 16A-16D and FIGS. 23A-23D). The visualization includes an indication of a generated measurement for each of one or more measures of the multiple measures (e.g., an image icon, color, or pattern indicating a measurement percentage, count, value, and/or threshold). The visualization includes associations, in the hierarchy, with the one or more measures of the multiple measures. For instance, the arrangement of the visualization can indicate graphical associations.

An operation 1454 includes updating the visualization responsive to an updated measurement for a measurement in the visualization. Trained models can be dynamic computer models that are updated overtime (e.g., in response to new data or according to a schedule). It is important to have an evolving view of the health of a model overtime by updating the visualization. In one or more embodiments, a computing system monitors one or more models (e.g., trained and/or dynamically updated models) by generating health measurements that indicate one or more health statuses or health objectives for the one or more dynamic computer models. One or more embodiments, introduce a circular approach rather than taking a siloed approach to monitoring. By providing well-rounded information, it can improve decision-making for a computing system or user.

Figure 15:
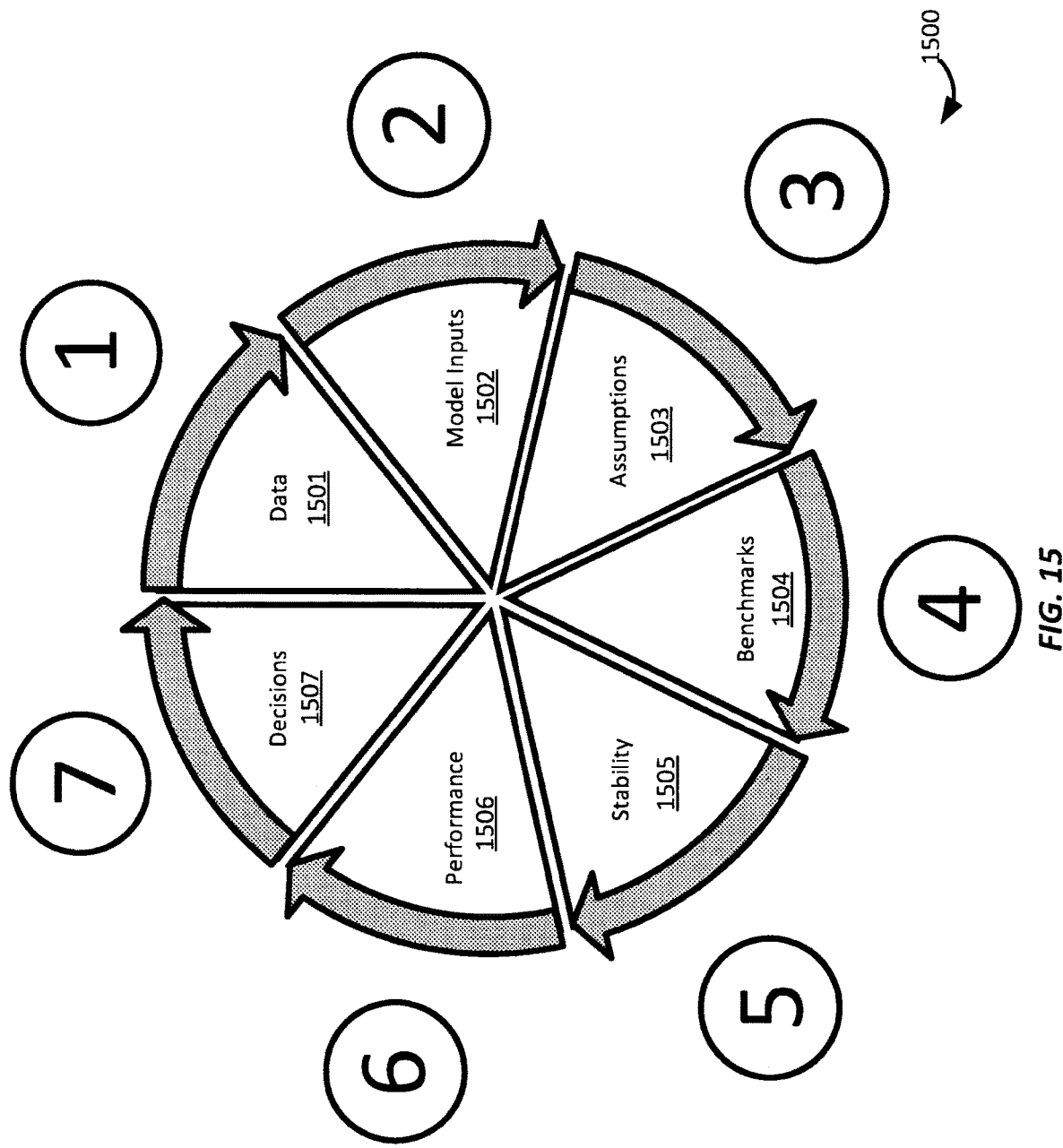
FIG. 15 illustrates a graphical user interface displaying a visualization of dimensions of monitoring model health according to at least one embodiment of the present technology.

The number of, and applicability of, models is increasing (e.g., risk models, artificial intelligence, and machine learning models). Models are becoming more data-dependent and interconnected. New issues arise in model governance, explainability and bias especially for high stakes risk models. FIG. 15 illustrates a diagram 1500 displaying the interconnectedness of dimensions useful in analyzing even a single model. In this example, modeling dimensions of data 1501 are used to develop a model. It may be important to monitor data 1501 to determine if good quality data is feeding into the model. Further, the data 1501 can influence how the model responds to model inputs 1502 during use of a developed model. The model inputs themselves can have stability issues or cause model drift overtime. The model inputs 1502 may also influence how the model treats assumptions 1503 regarding the developed model.

Data 1501, model inputs 1502, and assumptions 1503 can influence how benchmarks 1504 for the model are considered. Benchmarks 1504 are important to monitor because they are used for finding alternatives if the model breaks or performs poorly. Benchmarks 1504 are therefore interconnected with assessing the overall stability 1505 of the model, which affects the overall performance 1506, and subsequently decisions 1507 based on the model. Decisions 1507 are monitored for determining if, for instance, decisions based on the model are fair and unbiased. Stability 1505, performance 1506, and decisions 1507, may in turn feed into what data 1510 is used to update the model. One or more embodiments provide a visualization approach that makes it easier to understand components of individual models or a model system. This may be useful for finding issues when monitoring the system involves analyzing several dimensions that may be interconnected.

Figure 16A:
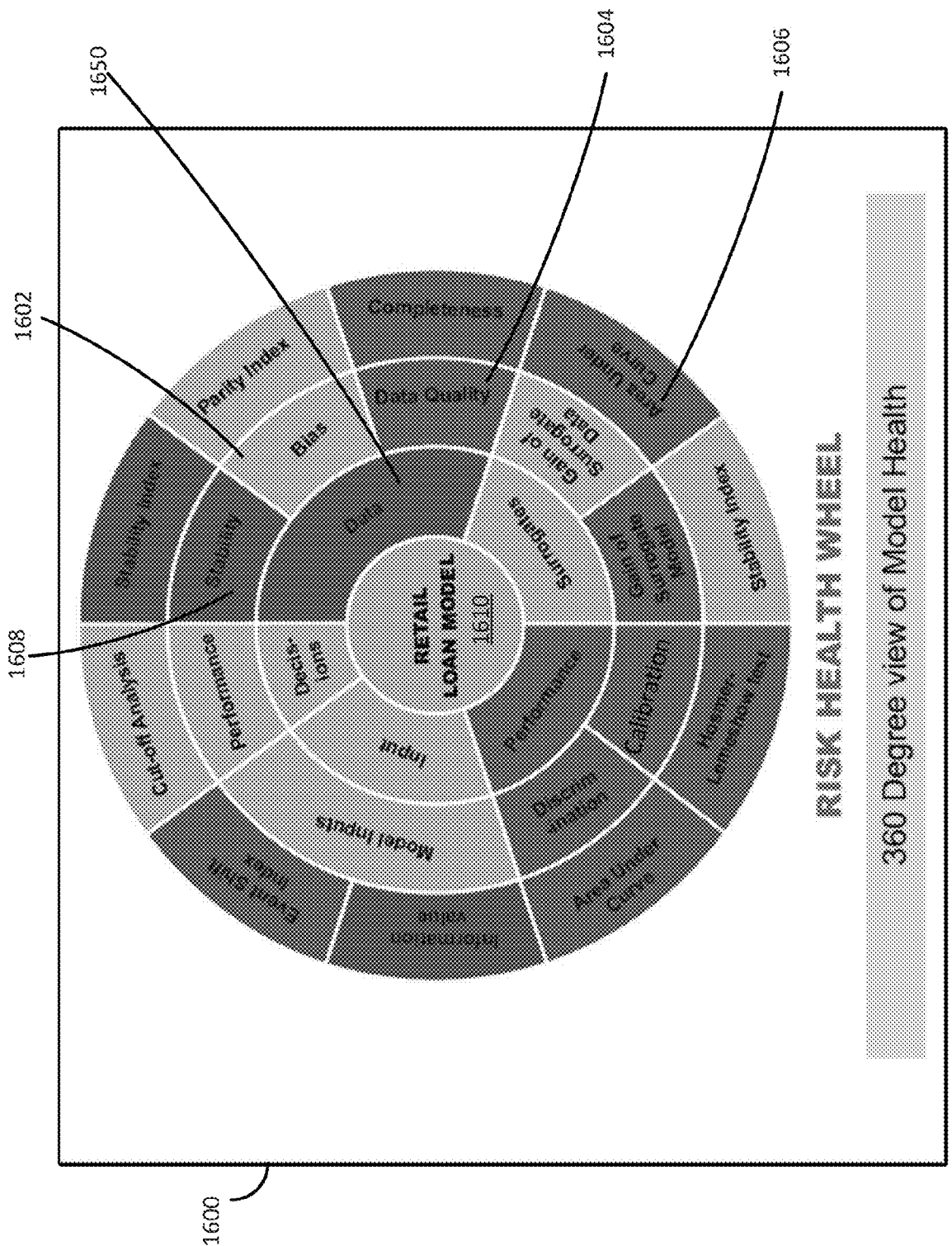
FIGS. 16A-16D illustrate an interactive graphical user interface 1600 displaying a visualization with a wheel design for monitoring a model according to at least one embodiment of the present technology.

FIGS. 16A-16D illustrate an interactive graphical user interface displaying a visualization with a wheel design for monitoring a model. FIG. 16A presents a graphical user interface 1600 for an approach for representing results in a hierarchy. The hierarchy is depicted as a circular diagram representing the levels in the form of circular layers. In this example visualization, the computing system generates the visualization by representing the hierarchy with concentric shapes. In this example, the shape is a circle. Each shape or circle of the concentric shapes represents a single level of multiple levels of the hierarchy. An outer level of the visualization represents the multiple measures in the hierarchy. The outermost layer displays the measure layer and each block (e.g., "Area Under Curve" block 1606) in the outermost layer represents an individual measure (e.g., a summation of area under a curve). Similarly, the inner layers are measure categories, analysis types, and analysis object types. Each layer except the innermost (e.g., central object 1610) has blocks that represent the individual dimension in the layer. Accordingly, the wheel design provides a more circular approach visually to dimensions of monitoring model health (such as the dimensions with a circular relationship discussed in FIG. 15). This wheel design is also reflective of the internal computations by the computing system to monitor dimensions with a circular relationship. The measures in the example wheel design have a color (e.g., red, amber, green) associated with it that indicates the health of the metric (e.g., the color is derived by threshold rules defined for the measure not visible in the diagrammatic example).

Any number of analysis types, measure categories and measures can be configured with corresponding reports. For instance, this wheel diagram can be used to give a comprehensive view of the health of an analysis object type such as a model, modeling system, or model component. Some analysis types may be pre-configured or available out of the box for users. For instance, in a scenario in which the object type is a model, it may be helpful to have Data analysis type (represented by "Data" block 1650) with preconfigured measure categories of data quality (represented by "Data Quality" block 1604) and bias (represented by "Bias" block 1602). The user can add other measure categories such as stability (represented by "Stability" block 1608). FIG. 16A shows other analysis types and measure categories that may be pre-configured. For instance, analysis types could include inputs (e.g., with model inputs and stability measure categories), performance (e.g., with discrimination, bias, calibration, accuracy, explainability, robustness, and stability measure categories), surrogates (e.g., with gain of surrogate model measure category), and decisions (e.g., with performance measure category). Other options not shown in FIG. 16A may be pre-configured but not selected for a particular visualization (e.g., model assumptions, benchmarks for champion or challenger models analysis types) or not visible because of the number of selected monitoring options. For instance, a user may have prioritized certain options.

In this example, the graphical user interface 1600 provides a 360-degree reporting view of a model as its central object 1610. For example, the central object 1610 in this case is a retail loan model which could be used in the retail industry domain for forecasting and demand planning models that manage supply chains. However, any other central object could be used to represent associations with a central object (e.g., other models and other systems). The visualization is useful to capture all dimensions of monitoring the central object in a single dashboard. This is an example of a wheel diagram that represents a comprehensive view of the health status of the analytical object. It shows the current status of each dimension and visually depicts the hierarchy and associations.

A visualization can display health indicators in each of different blocks of the visualization. Each block in the visualization can be defined by different rules for displaying the health indicators. For instance, each block in every layer of this example has an associated color that indicates the health of that dimension. The associated color is derived through threshold rules defined for the measure. The threshold rules can use aggregation logic to aggregate the effects of lower dimensions on a higher level in the hierarchy. For example, health indicators for a measure category can be defined based on multiple measures in that measure category. For example, logic could be used to determine a color of the measure category based on a count of measures of a certain color or a percentage of measures of a certain color. Similarly, health indicators for an analysis type can be defined based on the measure category or an individual measure. FIGS. 24A and 24D provide example logic for determining a visual indicator based on considering multiple components in a sub-level of a hierarchy.

In the graphical user interface 1600 the options for each level of the hierarchy are associated with multiple image codes. The image codes comprise computer instructions for displaying one or more of a color, icon, and pattern in the visualization in a position associated with a respective option of the options for each level of the hierarchy. In the example in FIG. 16A, computer instructions are used for a computing system to select a color between red, amber and green for each of the options. For instance, the "Data" block 1650 is currently red.

Figure 16B:
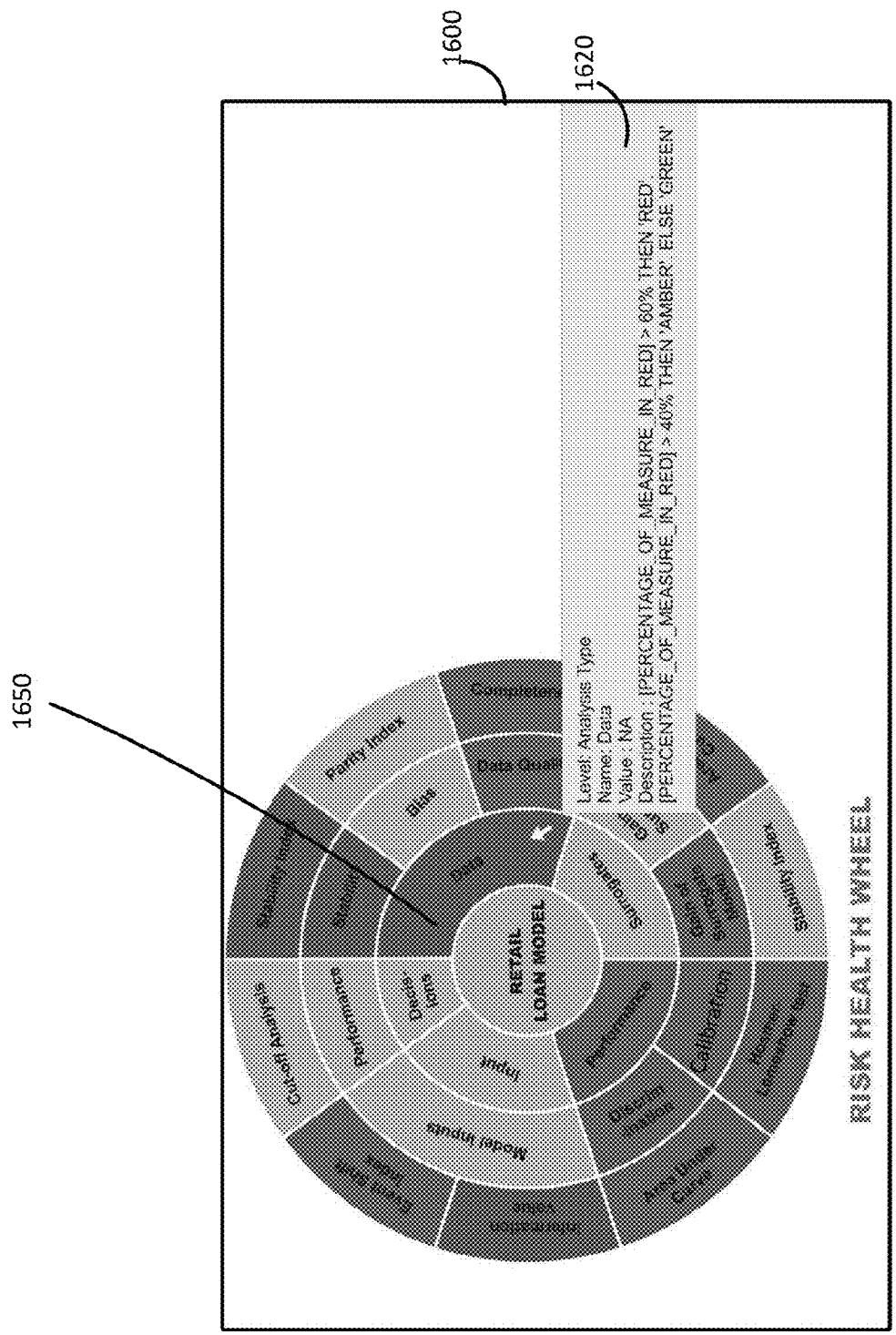

One or more embodiments, provide an interactive visualization. For instance, FIG. 16B shows that by hovering over an option, a user can see a user-interpretable description of the computer instructions (e.g., hovering a curser over "Data" block 1650 generates information block 1620 in response). According to the computer instructions when the percentage of measurements for the data modeling analysis associated with the "Data" block 1650 are greater than 60%, a red color is shown, and when lower than 40%, a green color is shown. In between the color is amber.

Figure 16C:
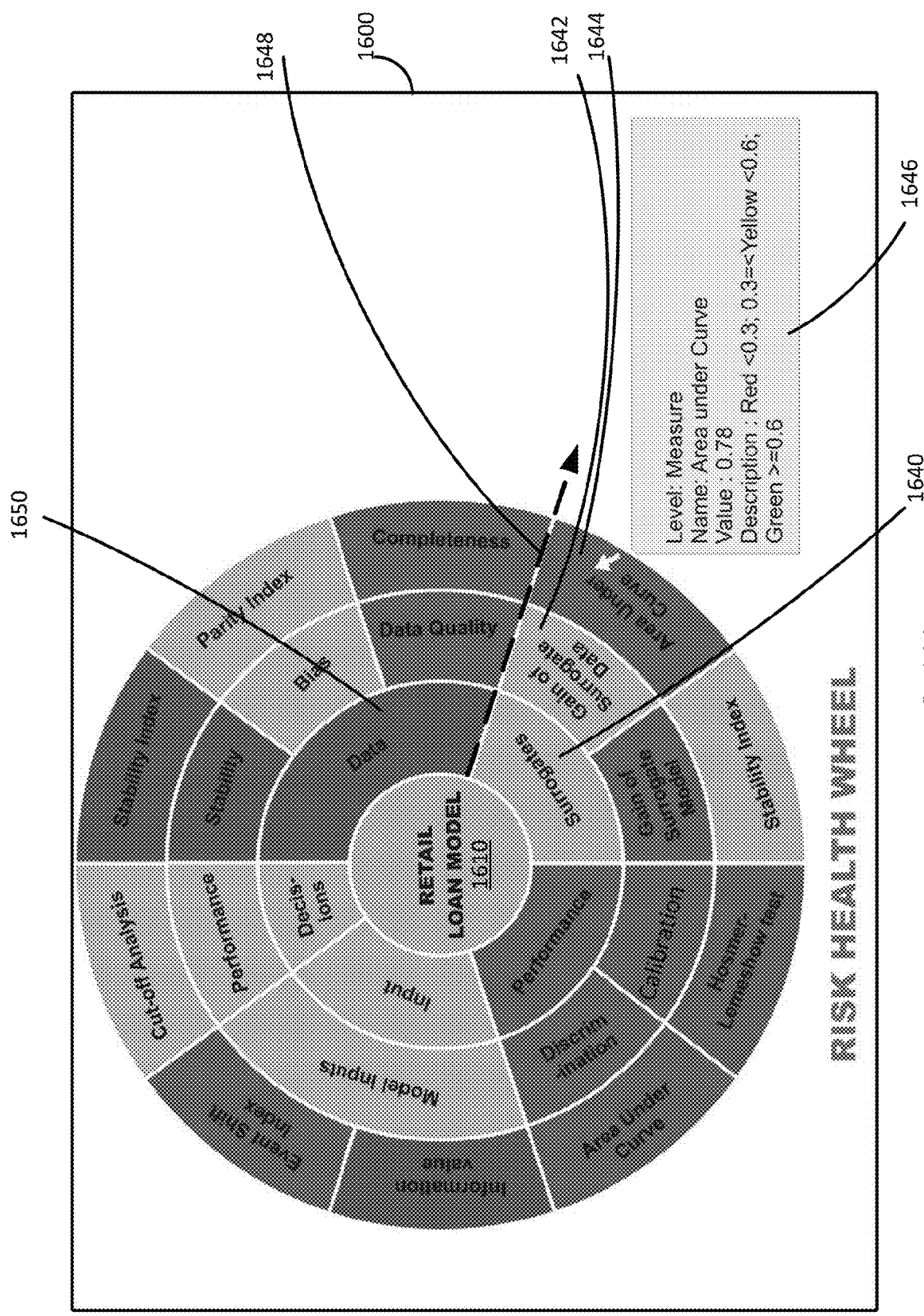
Figure 16D:
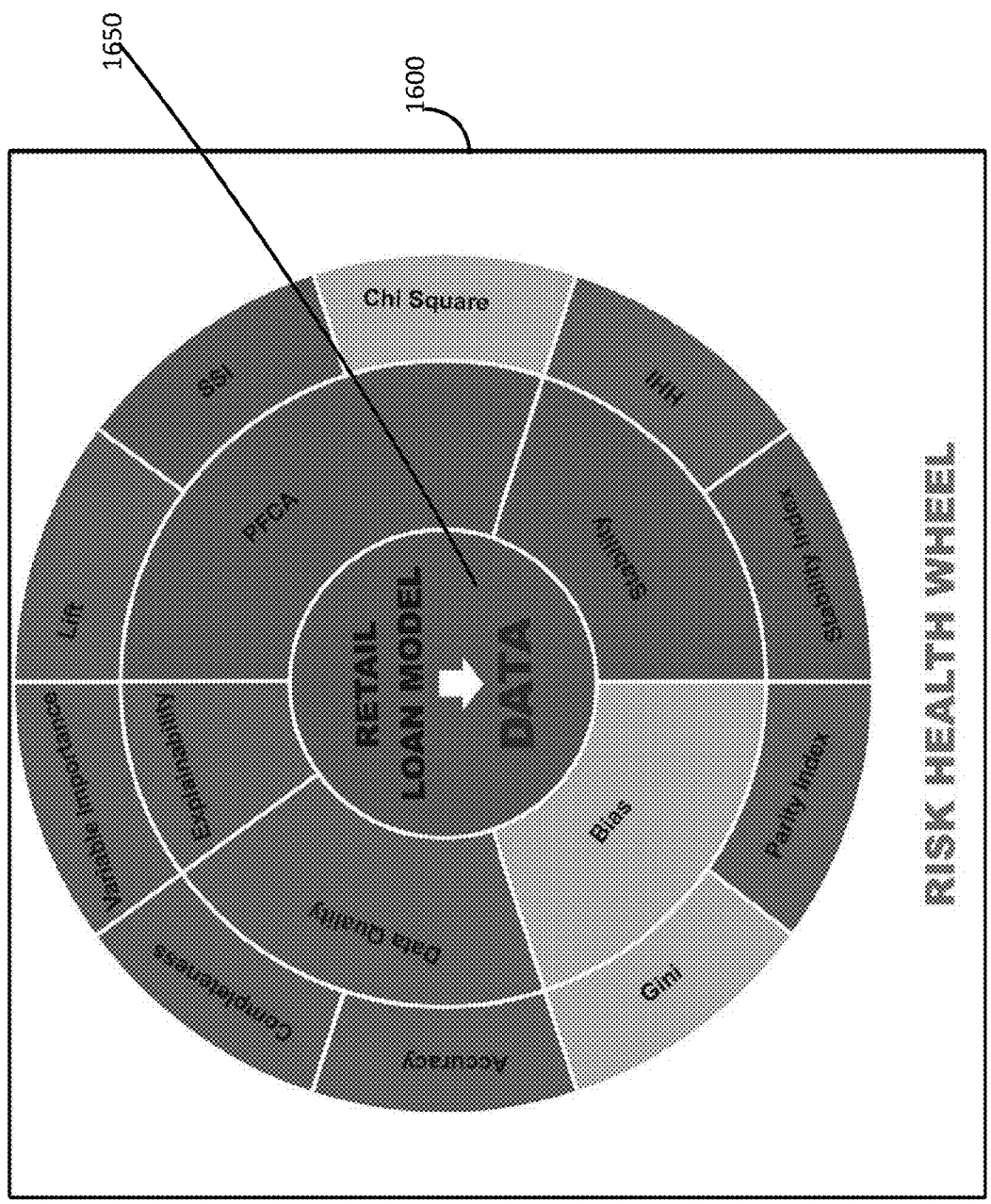

FIG. 16C shows the user hovering over the "Area Under Curve block" 1644, a different option in a hierarchy. As shown, each block can have its own set of rules. For instance, this "Area Under Curve block" 1644 is a measure and displays a code of green when the measure is greater than or equal to 0.6 in information block 1646. The hovering can also display the current measure of 0.78. Alternatively, the measure could itself be displayed as part of the block.

Accordingly, as shown in FIG. 16C, the computing system can generate a visualization providing a wheel design. Each concentric shape of the wheel design has a circular edge. In this case each shape has one edge that forms a complete circle, but in other cases, each shape could have more than one edge (e.g., a semi-circle shape). Each of the blocks of the outer level comprises a respective spoke for each of the multiple measures. A spoke is a block or rung that helps connect an inner layer of a wheel to an outer layer of a wheel. The visualization represents a respective health measurement of the health measurements by depicting an image within the respective spoke (e.g., "Area Under Curve block" 1644) representing a respective measure within the outer level of the wheel design. In this case the image is a color indicating the health of a measure (e.g., green for good and red for concern). The visualization represents associations with the respective measure in the hierarchy by presenting associated options of layers in radial proximity with the spoke. For example, "Area Under Curve" block 1644 is in radial proximity to "Gain of Surrogate Data" block 1642 to show association in a hierarchy because block 1644 is near block 1642 along a radius 1648 from the central object 1610. "Area Under Curve block" 1644 and "Gain of Surrogate Data" block 1642 are also in radial proximity with "Surrogates" block 1640 in a hierarchy.

The image codes can be used in indicate a root problem associated in the hierarchy with a model, or an aspect of a model, for further investigation. For instance, in this case red can be used to indicate a problem with a specific member or component in a hierarchy. In one or more embodiments, the visualization is interactive such that the user can change the visualization itself (e.g., the user can click on an option to further investigate it. For instance, in FIG. 16C, the computing system receives a user selection of a selected option in a level. For example, in FIG. 16C, the user selects the "Data" block 1650. As shown, in FIG. 16D, the graphical user interface 1600 shows an updated visualization to display only components associated with that selected option in the hierarchy. For example, "Surrogates" block 1640 is no longer apart of the visualization. In the example in FIG. 16D, the computing system updates the visualization in response to the user selection such that the selected option is a center shape in the concentric shapes of the visualization. This approach can allow more components than in the previous visualization to display that are associated in the hierarchy with the selected option. For instance, in FIG. 16C, only 3 blocks were a part of the outer layer for the "Data" block 1650. In contrast, in FIG. 16D, 10 blocks are a part of the outer layer for the "Data" block 1650. This can allow the user to view dynamically or selectively more data measures pertaining to a particular aspect of model monitoring.

Some models (e.g., a forecast model) are very dependent on data. By being able to drill into the "Data" block 1650, or another respective area, it can be helpful with monitoring the overall solution health, or can be helpful to address a problem, such as allowing the user to be able to quickly triage and remediate (e.g., excluding data sets) to ensure the model is producing the best answers.

Figure 17A:
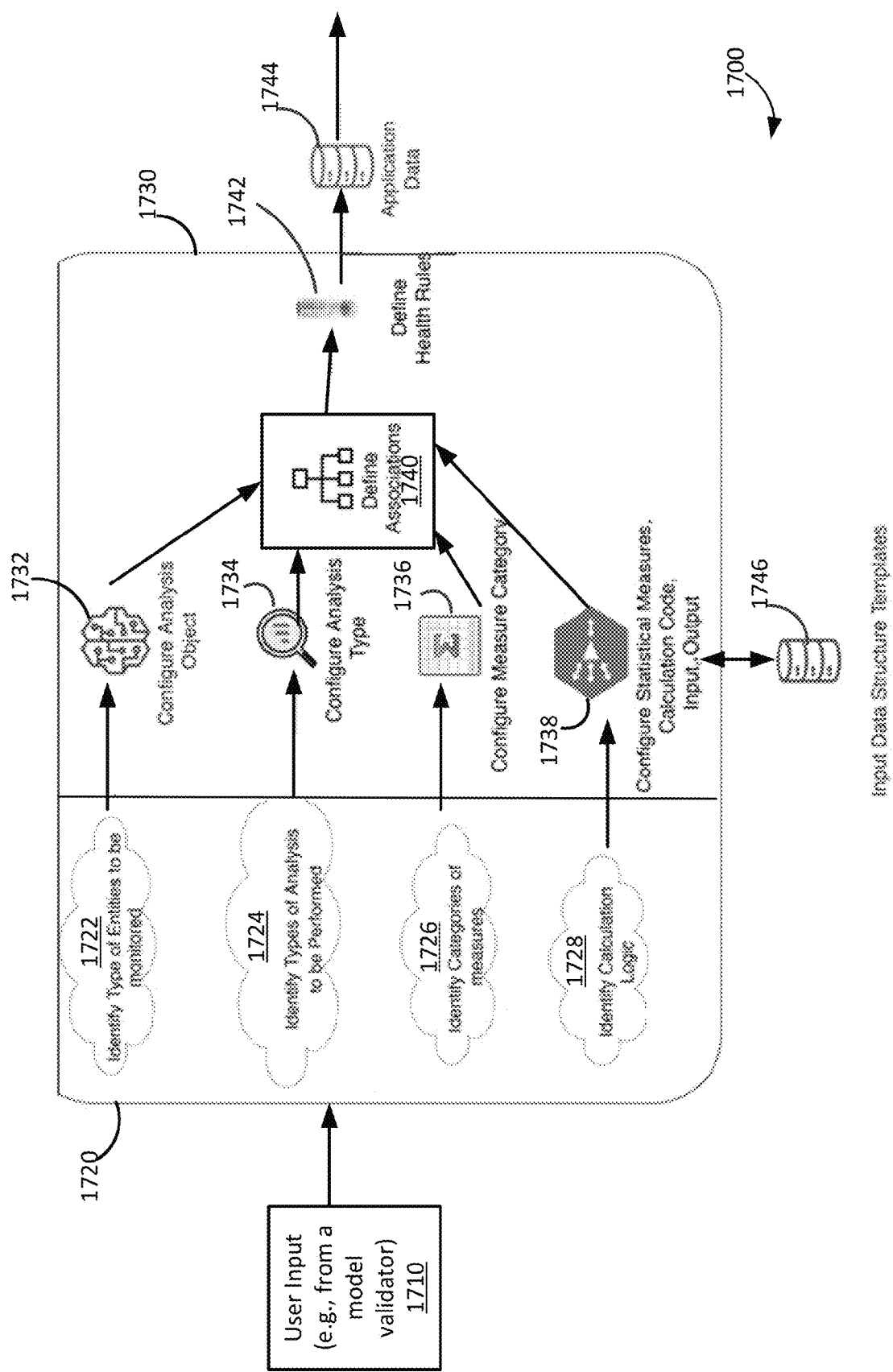
FIGS. 17A-17B illustrate an example of a block diagram of a system for monitoring a model according to at least one embodiment of the present technology.
Figure 17B:
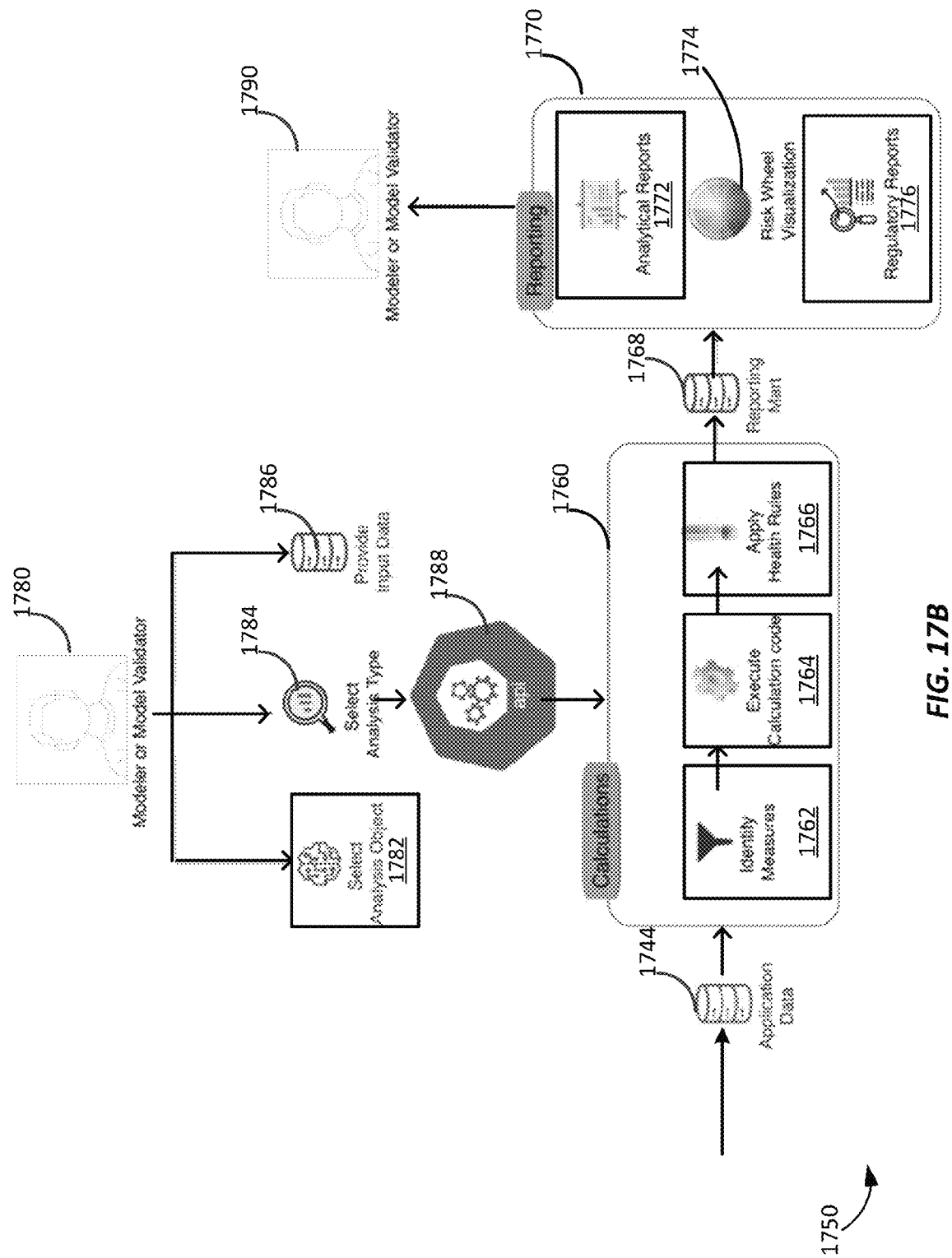

FIGS. 17A-17B illustrate an example of a block diagram of a system for monitoring a model. Most of the software solutions for model monitoring offer basic statistical measures but are not customizable or expandable to define, customize and monitor a range of dimensions related to the health of models.

FIG. 17A shows a system 1700 for supporting a configuration module 1730. FIG. 17B shows a system 1750 for supporting a calculation module 1760.

In this example, the calculation module 1760 is decoupled from the configuration module 1730 merely for example and could instead be integrated into one system. The configuration module 1730 is used for adding new dimensions in model monitoring. Some dimensions can be pre-configured or provided for configuring out of the box (OOTB) (so-called OOTB dimensions). OOTB dimensions can be applied to risk models and can be customized according to the user's needs. For instance, the configuration module can receive user input 1710. A user could include, for example, a model developer, model validator, or internal audit team. For example, the user could be performing model monitoring which is typically performed prior to implementation of models in a production environment or on an ongoing basis to ensure that the models are functioning as intended.

For example, the user input 1710 can be from a model validator and configure dimensions for monitoring related to data, model inputs, assumptions, benchmarks, population stability, model performance and decisions. In this example, the configuration module obtains module input 1720 comprising received user input and out OOTB dimensions. The module input can be received over one or more networks as shown. Additionally, or alternatively, the module input can be received over other means (e.g., input devices such as keyboards, graphical user interfaces, mouses).

In this example, the configuration module 1730 receives data 1722 identifying a type of entities to be monitored, data 1724 identifying types of analysis to be performed, data 1726 identifying categories of measures and data 1728 identifying calculation logic.

For each analysis object type, the dimensions follow a hierarchical structure configured by the configuration module 1730. The hierarchical structure in this example comprises an analysis object type configured in a component 1732 of the configuration module 1730 for configuring one or more analysis objects. An analysis object type is an abstraction of objects under consideration for performance monitoring. A typical example of an object type is a type of model for which the user wants to perform monitoring. One example of a model type is a binary target prediction model (e.g., model predicting percent of target population that will act on a coupon, model predicting percent of population that will default, and a prepayment model). Another example of a model type is a continuous target prediction model (loss given default or credit conversion factor model).

The hierarchical structure in this example comprises an analysis type configured in component 1734 of configuration module 1730 for configuring one or more analysis types. An analysis type is an analysis that the user wants to perform for an analysis object type (e.g., model input monitoring, data monitoring, decision monitoring, and performance monitoring).

The hierarchical structure in this example comprises a measure category configured in a component 1736 of configuration module 1730 for configuring one or more measure categories. A measure category includes various statistical measures that are used for the associated analysis type. The user can use the OOTB categories, create new categories, or use an existing category and associate new measures to it. For example, data drift, model performance, and calibration are typically specified as measure categories.

The hierarchical structure in this example comprises component 1738 of configuration module 1730 for receiving and/or deriving measures. A measure can be a statistical test or key performance indicator used in monitoring. It can be a main component of the monitoring calculations (e.g., a system stability index and receiver operating curve). A measure can be associated with a health indicator that is derived from the thresholds on the calculated value of the measure.

Measures can be received from one or more databases 1746 (e.g., with data populated on a schedule according to an input data structure template). The configuration module 1730 has a component 1738 for receiving input and output from the one or more databases 1746 and for performing operations on the measures (e.g., configure statistical measures and prepare calculation code). The calculation code is a repository of user-defined logic that is used for a computer to calculate a measure. The user can define the structure of the dataset type required in the logic for calculation, parameters, the expressions that define the logic, and the set of measures to which it applies. Calculation code can be used to calculate multiple measures. Calculation codes can be stored in the one or more databases 1746.

Output from the components 1732, 1734, 1736 and 1738 can be used by a user to define associations between analysis object, analysis type, measure category and measures in a component 1740. A component 1742 can be used to define one or more health rules. A health rule can be based on aggregation logic that is applied to the associated analysis object type, analysis type and measure categories. Health rules can be used to generate health indicators at each level and give an overall idea of monitoring (e.g., to a management user).

Application data from the configuration module 1730 can be stored and/or updated in one or more databases 1744 for use by other systems and/or modules. For example, FIG. 17B shows a system 1750 for performing calculations and reports. The system 1750 includes a calculation module 1760 used to perform calculations. For instance, the calculation module 1760 can receive application data from the one or more databases 1744. This application data can be generated after the analysis object, analysis type, measure category, and measures are associated (e.g., using system 1700 in FIG. 17A).

The calculation module 1760 can work in the background when a model is developed (e.g., using the SAS Risk modeling solution). In other words, the calculations are not dependent on a developed model. The calculation module 1760 stores the results in one or more databases 1768 (such as a data mart or reporting mart used for generating monitoring reports). A reporting module 1770 can retrieve the data for generating reports. For instance, the reporting module 1770 can generate analytical reports 1772, visualizations 1774 (e.g., a risk wheel visualization) and/or regulatory reports 1776. For example, the OOTB reports on SAS Visual Analytics adds flexibility for customizations of reports for a reporting module 1770.

The application data and results from the calculation module 1760 can be updated periodically such that one or more embodiments approximate continuous monitoring rather than considering discrete time intervals for calculations and reporting.

The system 1750 can be used for model monitoring. For example, a user 1780 (such as a modeler or model validator) could provide a selection 1782 of an analysis object (such as type and name of a model) a selection 1784 of an analysis type (e.g., types of analysis that needs to be calculated during model monitoring) and/or other user inputs 1786 such as key dimensions to monitor in the selected analysis, statistical tests to be executed for the dimensions, threshold values to indicate the nature of the results (favorable/unfavorable). These selections and inputs could be provided to the calculations module 1760 using an application programing interface (API) 1788.

The calculations module 1760 can be pre-configured and/or user-defined to identify measures 1762 (e.g., from application data) and execute 1764 calculation code on the identified measures 1762. For instance, after inputs are pre-configured or provided by the user, the calculations can be scheduled (e.g., every few seconds or every day). Results can be represented in such a way that it is intuitive, consolidated and support decision making related to the models. For instance, the calculations module 1760 can be used to apply health rules 1766 (e.g., to generate a visualization). Based on the results, an informed decision can be made about use of a model when the user has the information readily available about aspects of monitoring.

For example, a computing system may monitor one or more champion models and one or more challenger models deployed in production. Actual decisions may be taken on the champion model or some averaging strategy of champion models. Challenger models can be used to evaluate whether the challenger model performance is better than the champion model(s). In that case, the current champion(s) gets replaced by the challenger model(s). For instance, reporting module 1770 can be used to report on which one or more models should be used in decision making and which should be kept for other purposes (e.g., as challenger models).

One or more embodiments, provide holistic monitoring to analyze various aspects about models. For instance, reporting can be used to compare champion and challenger models based on various analysis types under consideration. Reports can provide early feedback if the currently deployed model is not performing well. For example, if the analysis of input data of a champion model indicates instability, then it will indicate that there is a high chance of performance of model to go down very soon.

The database(s) 1768 (e.g., a reporting mart) can also be used to store information gathered over time for reports (e.g., stored key performance indicator values and health indicators). This can be used for reporting on historical trends of various analysis of model and target population. It can also allow for comparison of the trend across various models, inform the margin of model error, and/or identify associations that lead to model failures. In addition, it will allow the system to track model degradation via historical data in reporting mart 1768. This information on model degradation can be fed back to the modeler or model validator 1790 for improving a model development process (e.g., to redevelop or recalibrate deployed models).

Figure 18A:
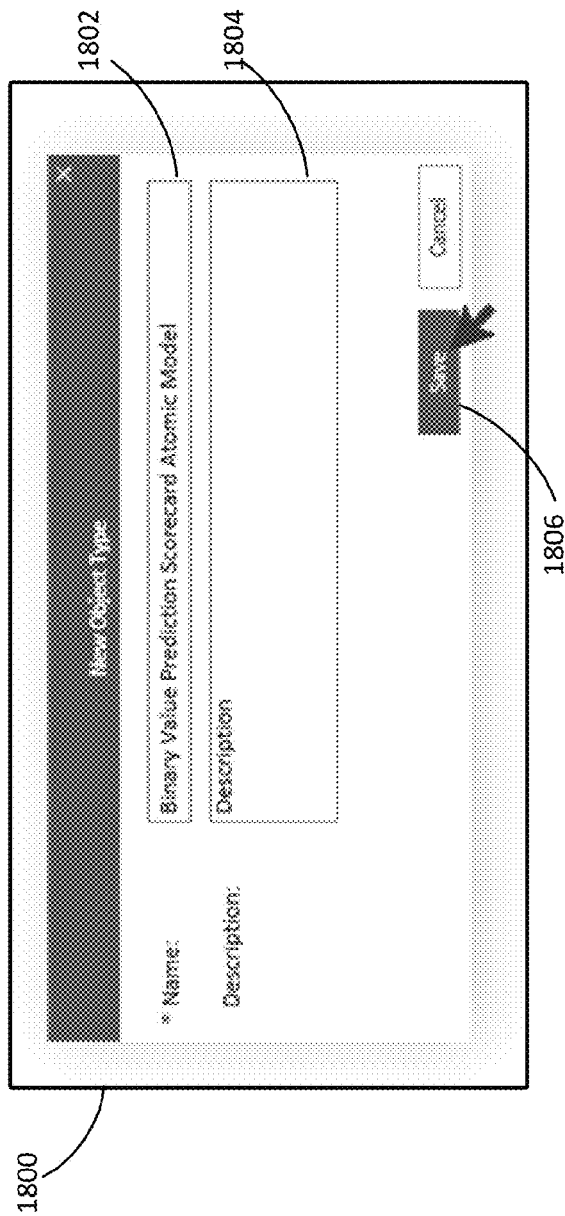
FIGS. 18A-18B illustrate example interactive graphical user interfaces for generating an analysis object according to at least one embodiment of the present technology.
Figure 18B:
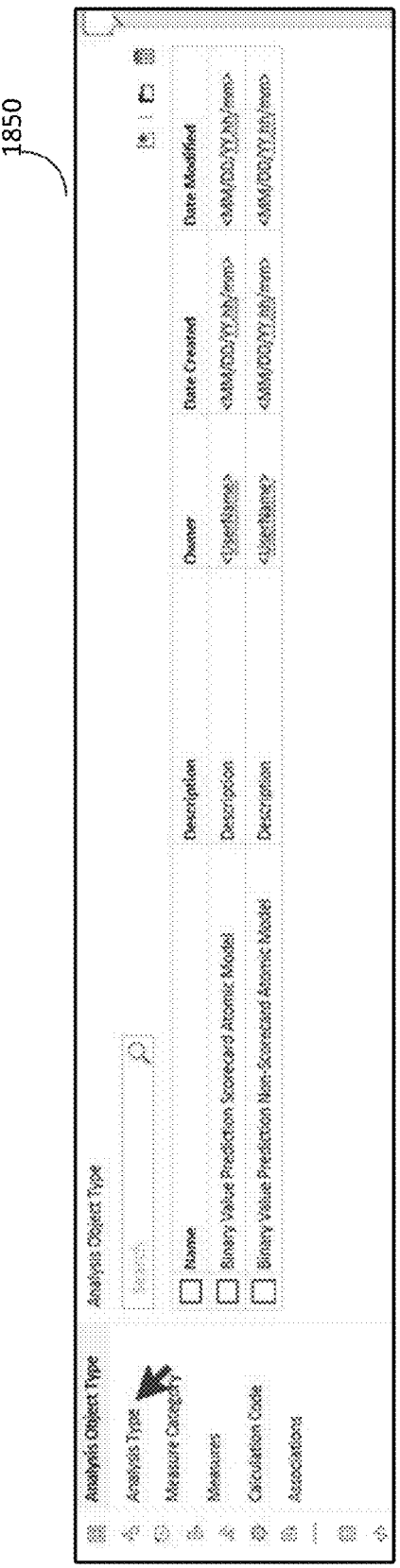

FIGS. 18A-18B illustrate example interactive graphical user interfaces for generating an analysis object. FIG. 18B provides an example graphical user interface 1850 for a system to configure performance entities (e.g., Object Type, Analysis Type, Measure Category, and Measures) all in one workspace and create associations within it to an analysis object. Once the entities are created, a user can establish the mapping, by using Calculation Code and Associations tools. For instance, in FIG. 18A the user creates a new object type and provides an identity 1802 and description 1804. In this example, the user is analyzing a computer model (a binary value prediction scorecard atomic model). The user can select a save control 1806 to save the new object type, which appears in the graphical user interface 1850 in FIG. 18B under the analysis object type tab.

In one or more embodiments, the health measurements are for assessing multiple models. For instance, in FIG. 18B the computing system shows a graphical user interface 1850 regarding analysis objects. In this example, the computing system has two analysis objects to monitor two different models (a binary value prediction scorecard atomic model and a binary value prediction non-scorecard atomic model). For instance, the computing system could monitor two different models as a challenger and a champion model as explained in more detail with respect to FIG. 17B.

In one or more embodiments, a computing system can generate a visualization representing a subset of the multiple models. For example, the visualizations in FIGS. 16A-16D only visualized a single monitored model.

FIGS. 19A-19B illustrate example interactive graphical user interfaces for generating an intermediate level. FIG. 19A shows an example analysis type tab 1910 in graphical user interface 1900. Each analysis type comprises a distinct dimension for monitoring one or more trained models. Analysis types can be selected to associate with an object type (like a model) or analysis types added or removed. FIG. 19B shows an example measure categories tab 1960 in graphical user interface 1950. The measure categories can be associated with the analysis types. For instance, categories such as description, owner, date created, date modified can be used for a user to select analysis types to associate with an object type (like a model) and to select measure categories to associate with an analysis type. A user can define health rules to control how these areas are portrayed in a visualization (e.g., the visualization in FIGS. 16A-16D). In the example shown in FIG. 19B, the user selects the measures tab 1970 to create measures to associate with the measure category.

Figure 20A:
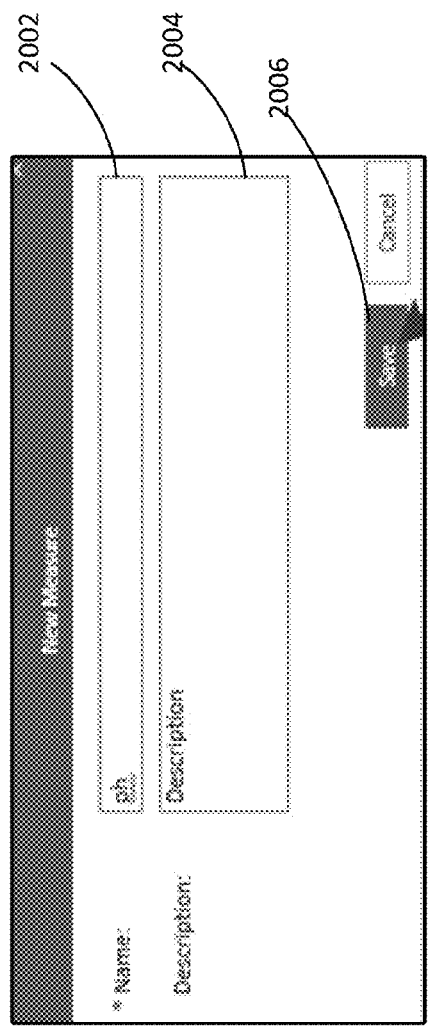
Figure 20B:
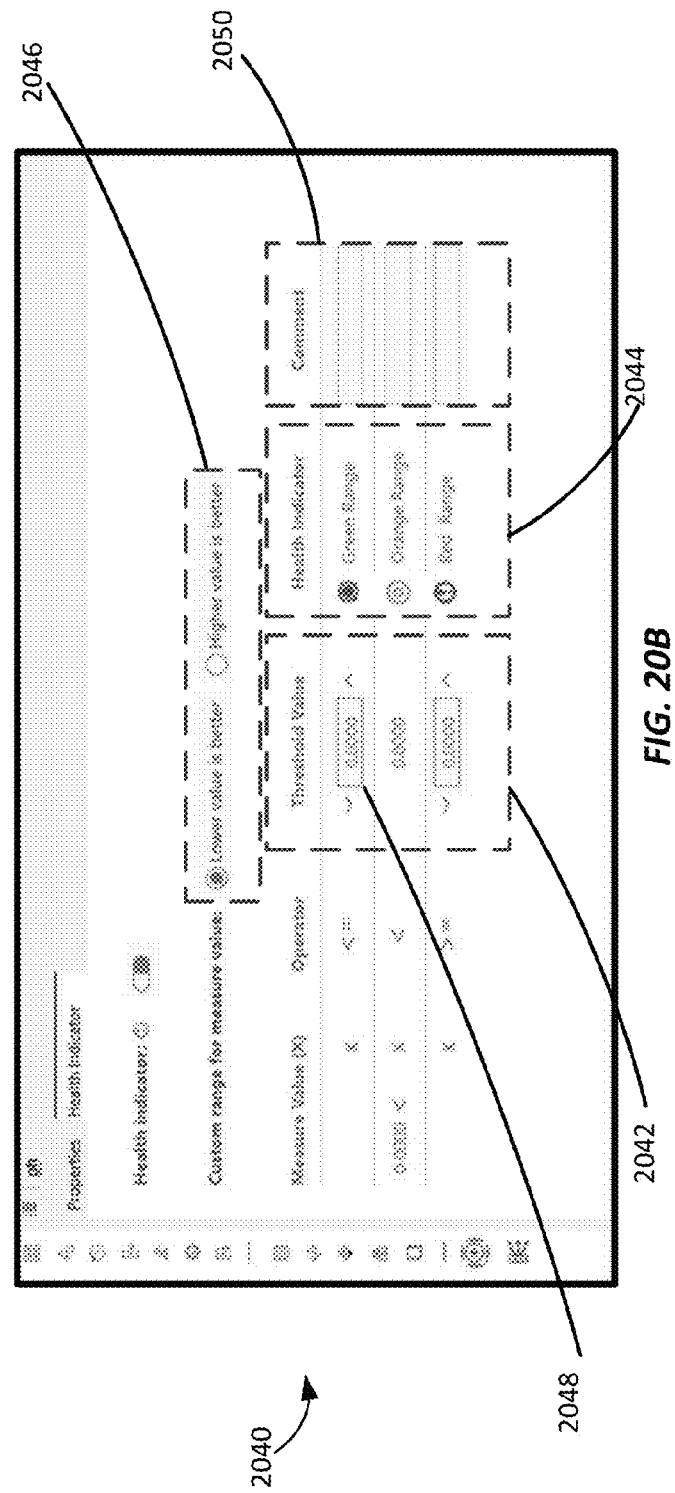
Figure 20C:
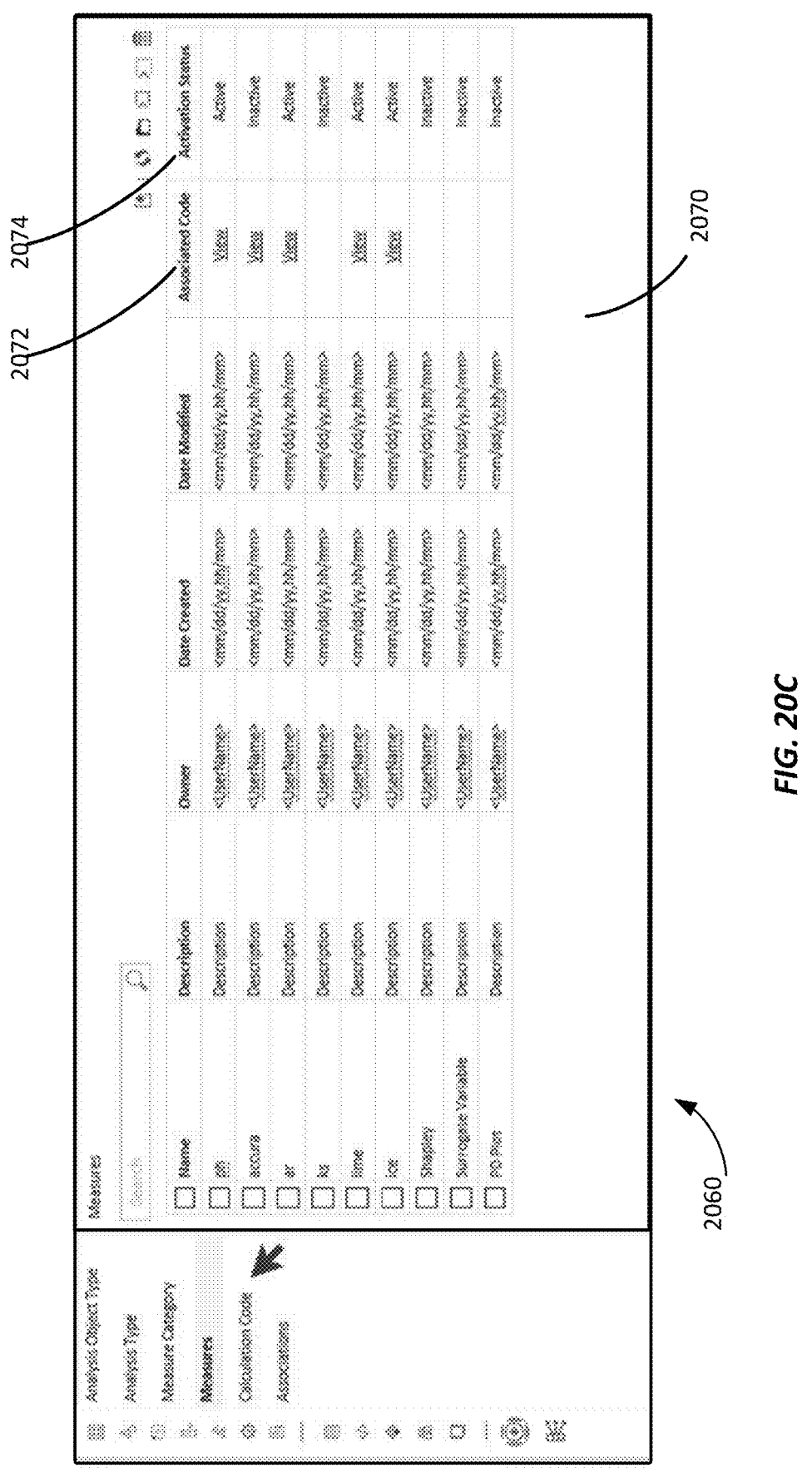

FIGS. 20A-20C illustrate example interactive graphical user interfaces for generating a measure. FIG. 20A shows a graphical user interface 2000 for adding a new measure. The user can specify properties for the new measure (such as a name 2002 for the measure and user-interpretable description 2004 for the measure). Using the save option 2006, the user can save the measure and its properties for associating in a hierarchy.

In one or more embodiments, a computing system receives a computer rule set associating one of multiple image codes with a measurement threshold. For instance, FIG. 20B shows customizable threshold values 2042 for each of multiple measurement thresholds for a given new measure ph. A specific health indicator 2044 can be associated with each of the customized thresholds. The computing system can monitor the one or more trained models by determining the updated measurement has crossed a measurement threshold of the multiple measurement thresholds. The computing system can update the visualization by changing an image according to the updated measurement and the computer rule set. For instance, in this example, ph is used as a measure for monitoring a biological system. A ph of less than or equal to zero may be associated with a red range since ph should not read less than 0 since ph is normally on a 0 to 14 scale. A value lower than zero may indicate a problem with measurement of ph. The options may be guided for some known measurement types. For instance, the computing system may set the middle threshold based on the user's answer to questions 2046. If the user had selected "Higher value is better", the amber threshold value may have defaulted to 14. Given the specific application, a particular measure may be more desirable or appropriate. In this example, the user can change the threshold 2048 from transitioning from green to amber to indicate a threshold closer to desired or appropriate ph measure results.

The graphical user interface 2040 may have other customizable options for controlling the visualization. For instance, a comments area 2050 may allow the user to provide appropriate messages should the user explore a measurement in the visualization at a particular time. For example, if the measure is showing green in the visualization, then a comment displayed could indicate expected range for ph is 6-7. Additionally, or alternatively, if the measure is showing amber or red, the comment displayed could indicate to drop this measure from monitoring the model until investigated further.

In one or more embodiments, where multiple models are monitored, a computing system can determine a measurement has crossed a measurement threshold associated with a measure of the hierarchy (e.g., the ph measure goes below zero). The comment can indicate a recommendation to use an alternative one or subset of the multiple models (e.g., one not using ph as a measure).

FIG. 20C shows example measures on a measures tab 2070 in a graphical user interface 2060. An activation status column 2074 allows a user to control monitoring of particular defined measures (e.g., as part of a visualization described herein). For instance, active measures can be monitored whereas inactivate measures can be ignored for the particular monitoring scenario. An associate code column 2072 allows a user to associate code with a particular measure (e.g., for associating computer instructions for gathering or performing the measurements).

FIGS. 21A-21E illustrate example interactive graphical user interfaces for generating or editing computer instructions associated with a particular measure.

Figure 21A:
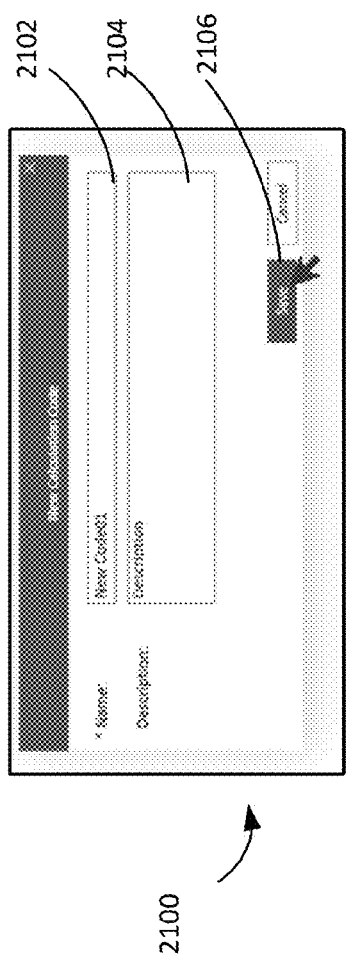
FIGS. 21A-21E illustrate example interactive graphical user interfaces for editing computer instructions according to at least one embodiment of the present technology.

FIG. 21A shows a graphical user interface 2100 for adding a new code for associating with a measure (e.g., a measure on the measures tab 2070 in FIG. 20C). The user can specify properties for the new code (such as a name 2102 for the code and user-interpretable description 2104 for the code). Using the save option 2106 the user can save the code and its properties for associating with a particular measure.

Figure 21B:
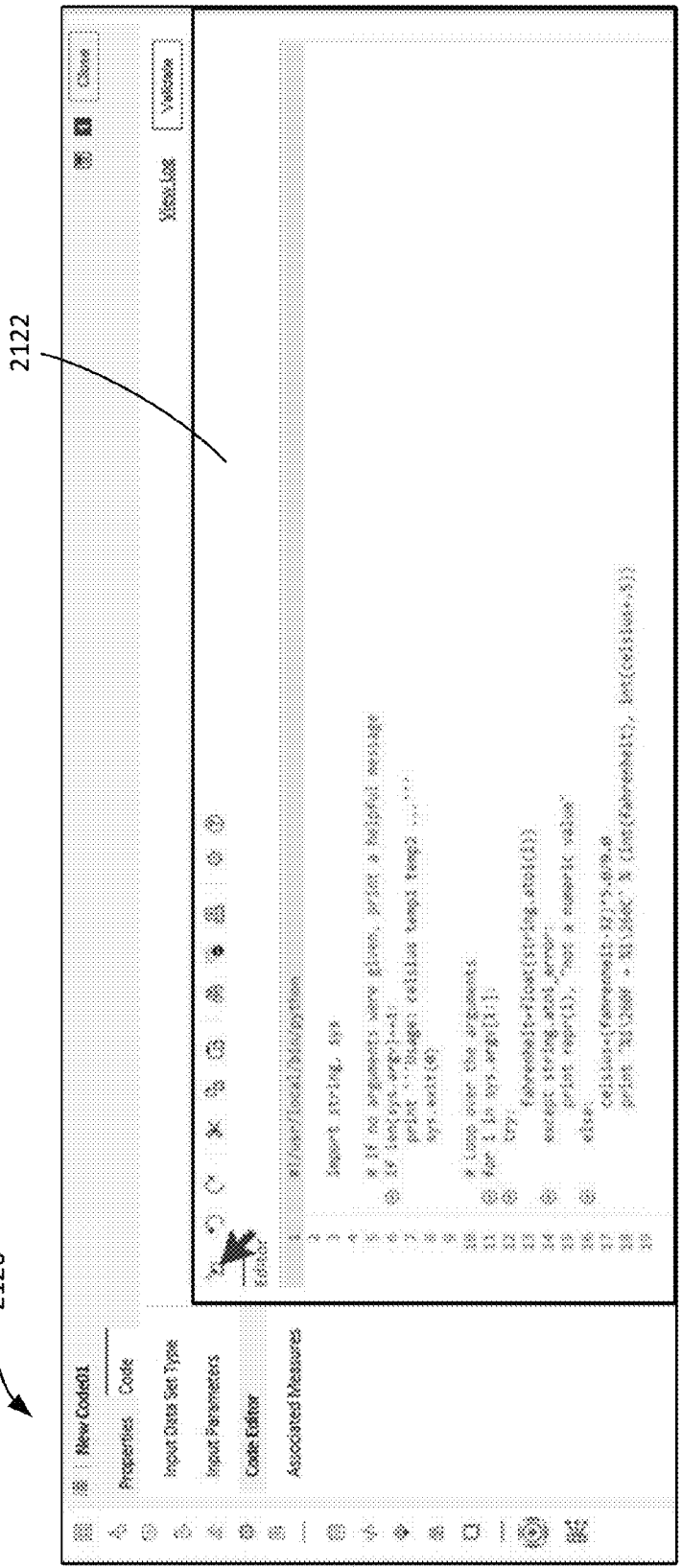

FIG. 21B shows an example of a graphical user interface 2120 for editing a code in a code editor 2122. For instance, the code can be set up by the user such that a computing system receives a user-configured schedule for generating, autonomously, a respective measurement for each of multiple measures. The computing system can generate a plurality of updated measurements according to the user-configured schedule. In this example, the code pertains to performing measurements. The computing system receives computer instructions to pull temperature measurements as part a code execution loop. The computing system can generate an indication of a risk category for the one or more trained models according to each of the updated measurements. For instance, a first recorded temperature could be associated with a green risk category, and then when the code loops again and pulls in a measurement, the new risk category could go to an amber risk category.

Figure 21C:
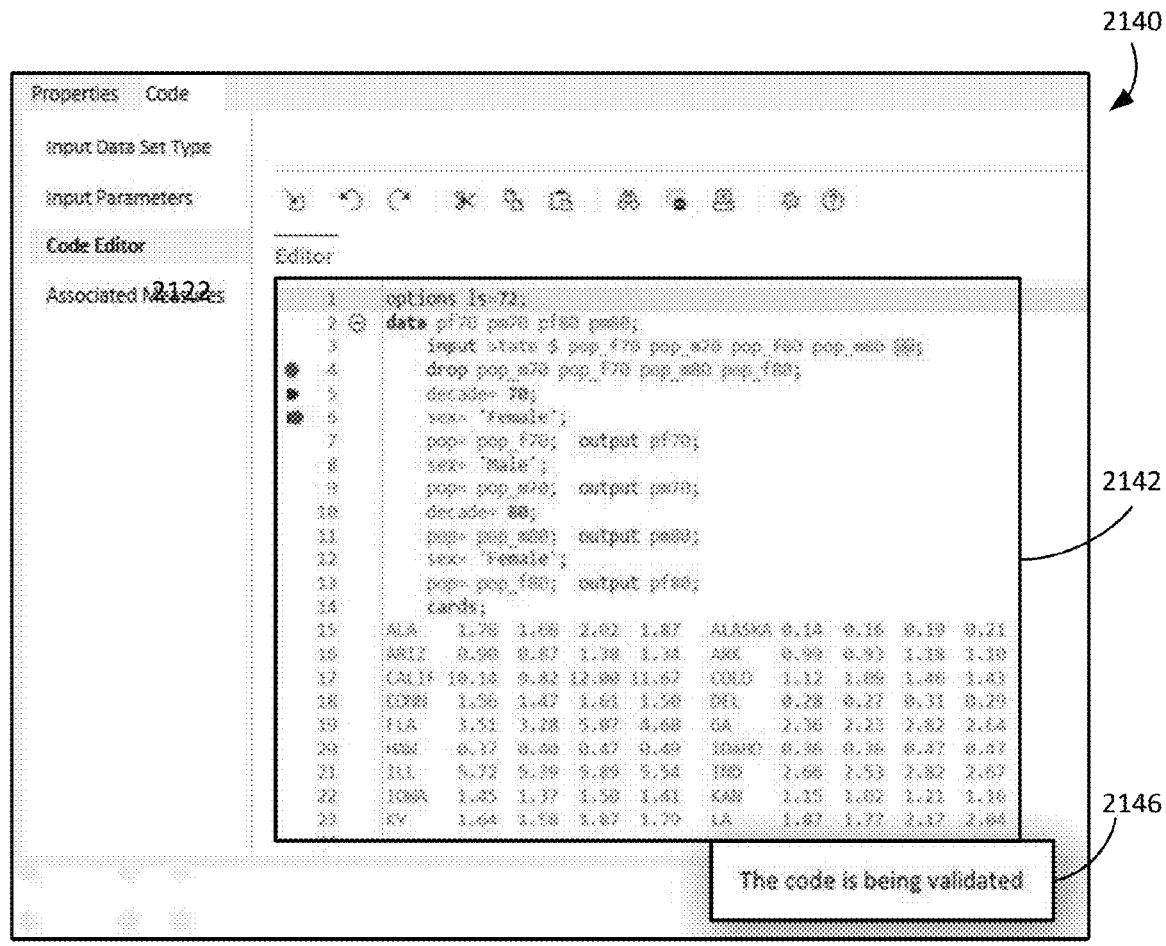
Figure 21D:
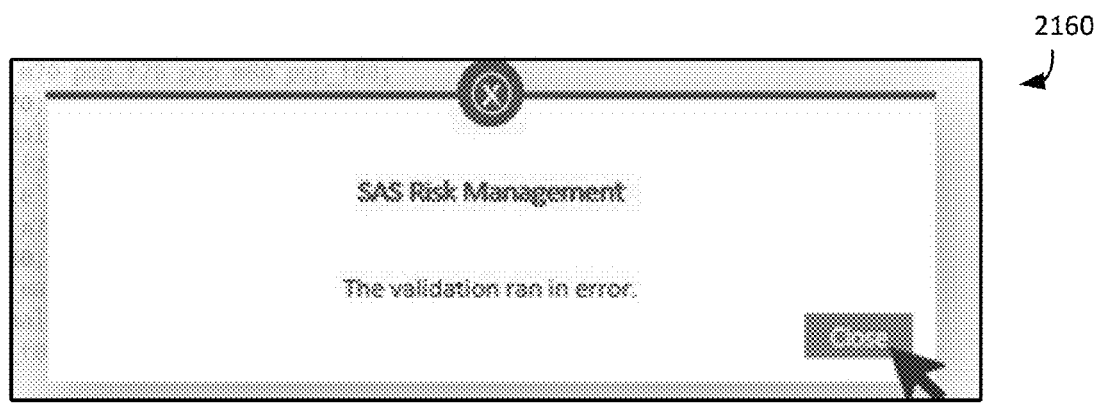

FIG. 21C shows an updated graphical user interface 2140 that has an updated code portion 2142 (e.g., for a different type of measurement). The computing system can check to see if the code can be validated or otherwise preform correctly. This can be helpful for user-defined code. In FIG. 21C, the computing system can display a message 2146 indicating that it is checking the code. The computing system can send an error message to the user to correct the code if the computing system does discover an error. FIG. 21D shows an example error message 2160 indicating that the validation ran in error.

Figure 21E:
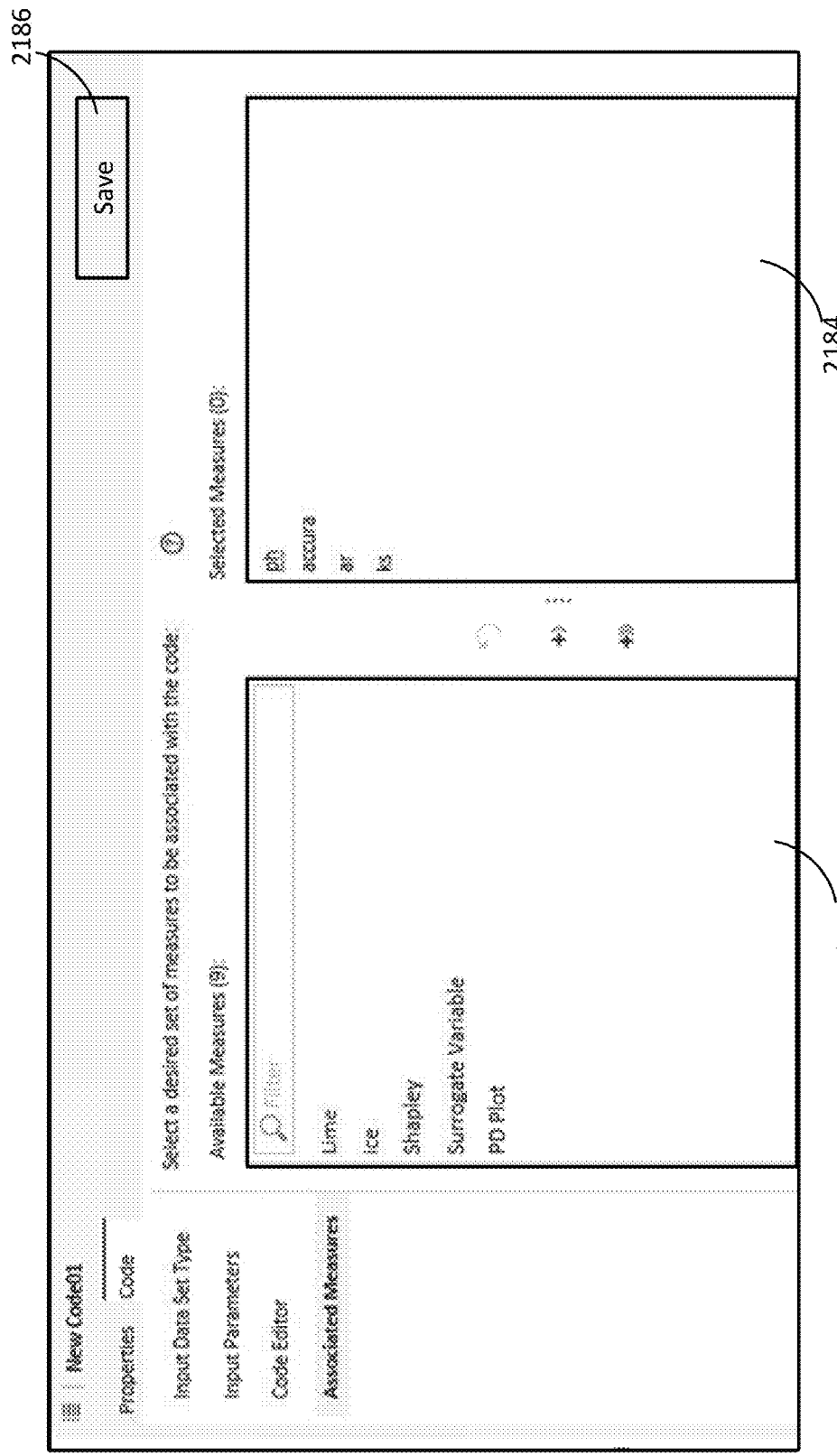

Once a code is validated, the code can be associated with particular input data set types, input parameters, or associated measures. For example, FIG. 21E shows an example graphical user interface 2180 displaying available measures 2182. A user can search for and select one or more measures 2182 to associate with the code. For example, the user can drag selected measures to a selected measures region 2184. The user can select a save option 2186 on this dialog of the graphical user interface 2180 to explicitly associate the desired measures with a code entity.

Figures 22A, 22B:
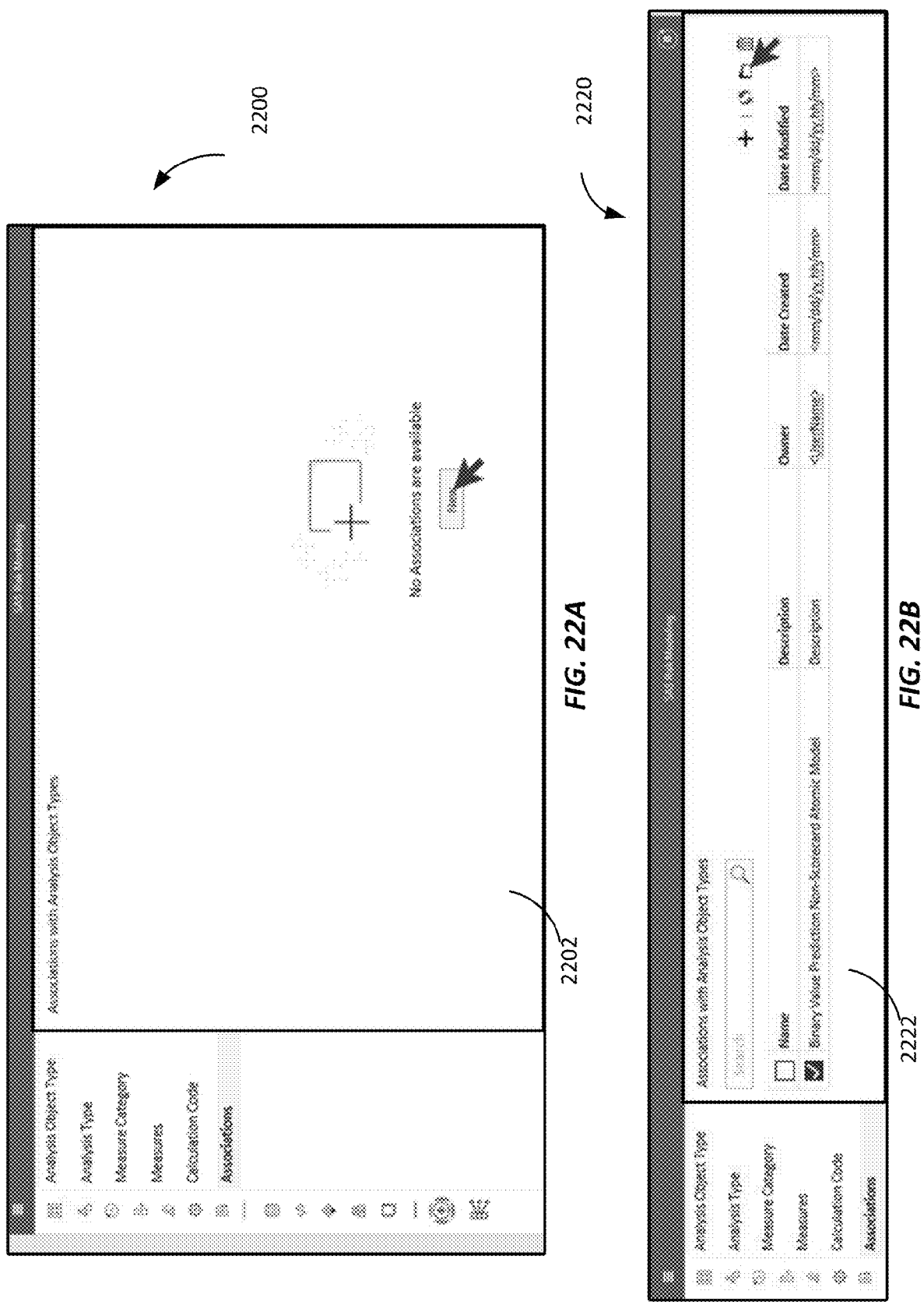
FIGS. 22A-22C illustrate example interactive graphical user interfaces for establishing a hierarchy according to at least one embodiment of the present technology.
Figure 22C:
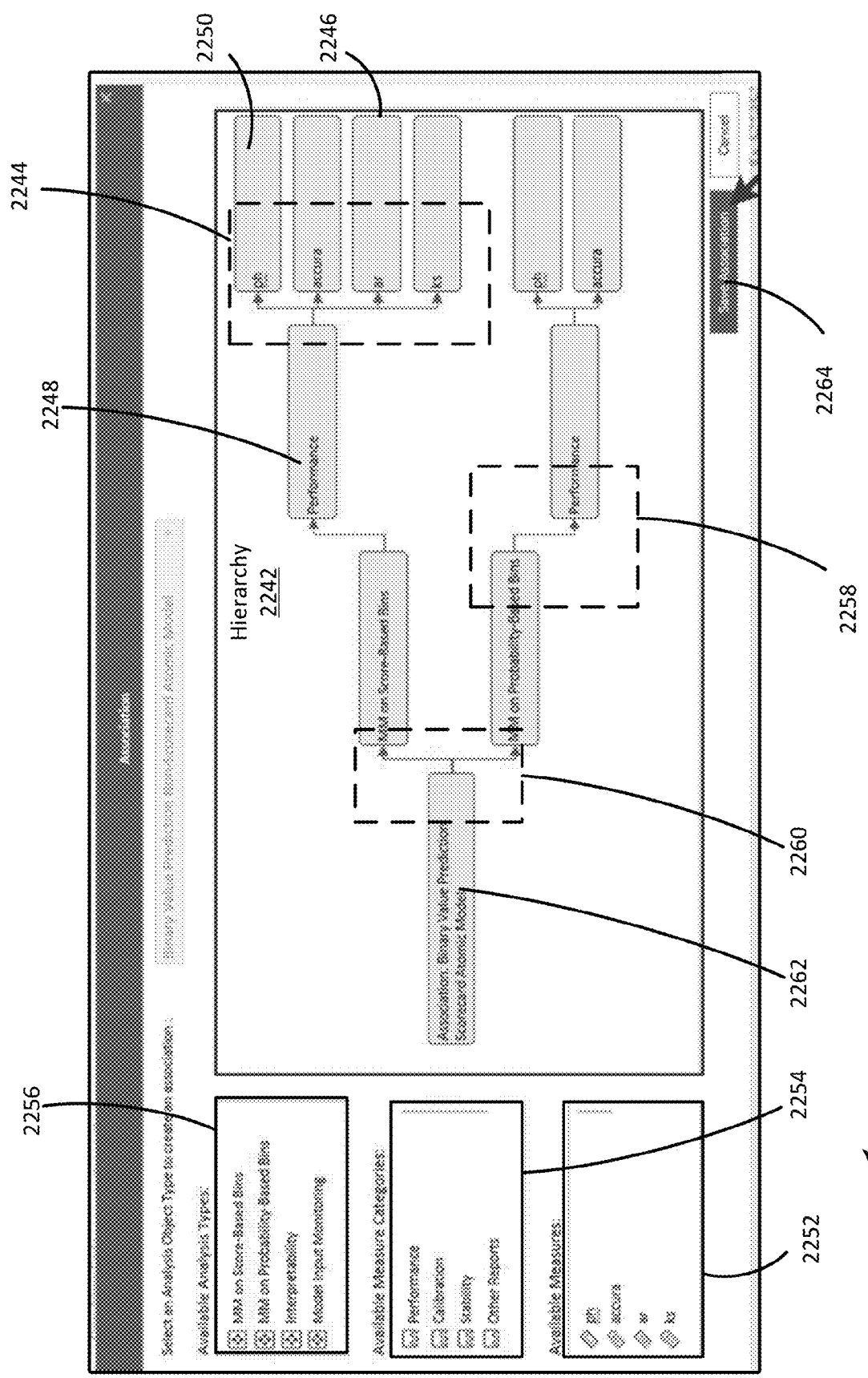

FIGS. 22A-22C illustrate example interactive graphical user interfaces for establishing a hierarchy. FIG. 22A shows a graphical user interface 2200 for building a hierarchy from the associations tab 2202. FIG. 22B shows a graphical user interface 2220 with an updated associations tab 2222 displaying a newly added hierarchy. The hierarchy can be selected for use for monitoring and/or a visualization.

FIG. 22C shows a graphical user interface 2240 for a user to form or edit a hierarchy (e.g., a hierarchy referenced on the associations tab 2222 of FIG. 22). In this example, the hierarchy 2242 includes an association 2244 between each of the multiple measures 2252 and a measurement category of multiple measurement categories 2254. A given measure of the multiple measures can be associated with only one of the multiple measurement categories. For instance, measure 2246 is associated with measurement category 2248. Additionally, some measures can be used for multiple measurement categories (e.g., the user-defined ph measure 2250 created as shown in FIG. 20A). In this example, the hierarchy 2242 includes an association between measurement categories 2254 and analysis types 2256. For example, association 2258 associates a measurement type of performance with an analysis related to probability-based bias. As with measures, a measurement type can be associated with only one of the analysis types 2256 or multiple ones. In this example, the hierarchy 2242 includes an association 2260 between one or more analysis types 2256 and the at least one model 2262. By associating the analysis type with the analyzed model, the analysis types can be a distinct dimension for monitoring the one or more trained models. Each analysis type can form a distinct hierarchy structure for a visualization (e.g., for a wheel design described herein or other visualization types such as those shown in FIGS. 23A-23D).

The computing system generates the visualization in a graphical user interface of a user-configured hierarchy. For example, a user-configured hierarchy 2242 associating each of the multiple measures with a given one of the one or more intermediate levels of the hierarchy, and each of the one of the intermediate levels of the hierarchy with the at least one model.

The computing system can allow a user to edit this hierarchy to change a resulting visualization. For example, the computing system can receive a user indication to change an association in the user-configured hierarchy (e.g., by deleting ph measure 2250) or add an association in the user-configured hierarchy (e.g., dragging an additional analysis type of the analysis types 2256 into the hierarchy 2242). The computing system can establish an updated hierarchy according to the user indication (e.g., in response to the user selecting the save association option 2264). The computing system can update the visualization responsive to updated measurements according to the updated hierarchy.

Accordingly, embodiments herein provide user interfaces for establishing and customizing components of monitoring of a system (e.g., a computing model), and establishing a hierarchy for visualizing dimensions of monitoring the system. One or ordinary skill in the art will appreciate other interface designs other than shown herein.

Figure 23A:
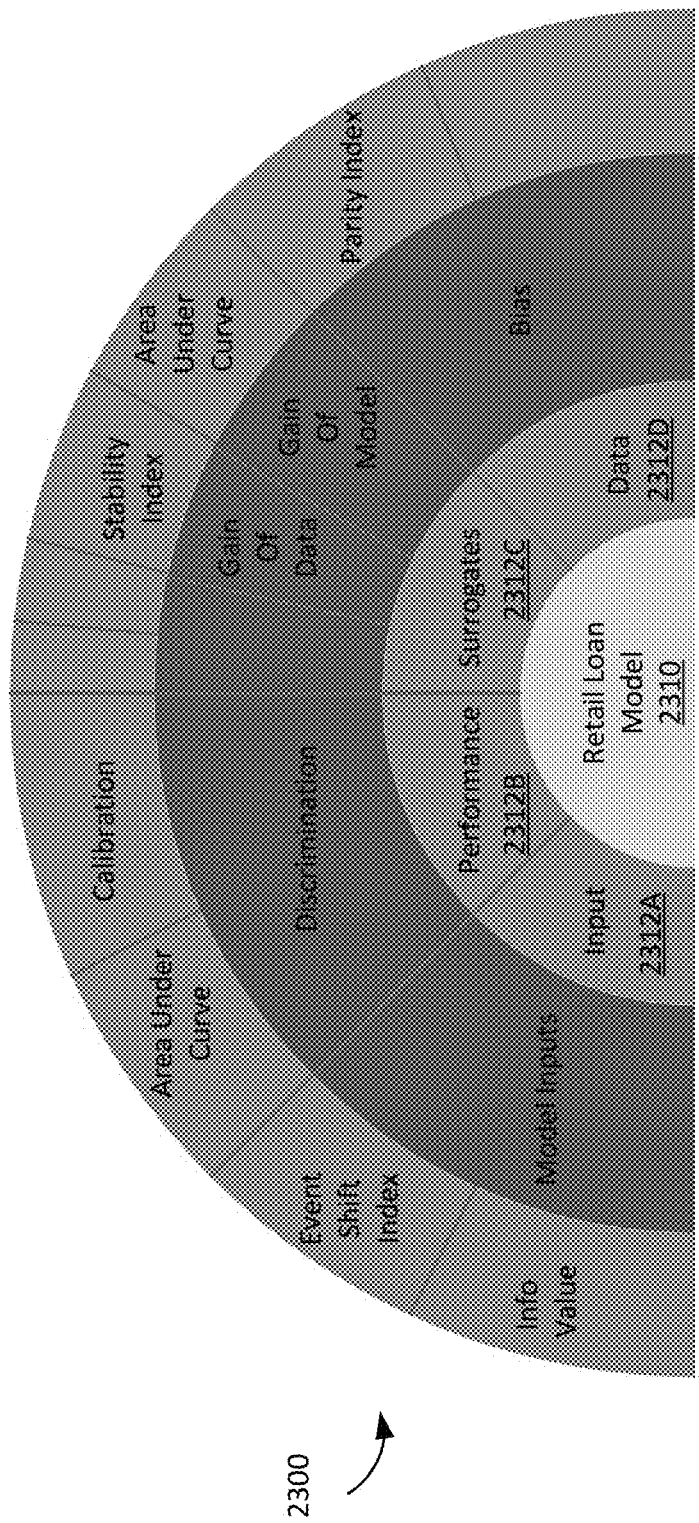
FIGS. 23A-23D illustrate example graphical user interfaces with visualizations for monitoring a model according to embodiments of the present technology.

One or more embodiments, also allow a user to change the form of the visualizations. FIGS. 23A-23D illustrate example graphical user interfaces with visualizations for monitoring a model. FIG. 23A represents an example visualization 2300 with concentric shapes. In this example, the concentric shapes are semi-circles. As with the wheel design discussed with respect to FIGS. 16A-16D, each of one or more shapes of the concentric shapes comprises one or more sub-components in the visualization according to a hierarchy. Each sub-component of a given shape of the concentric shapes in the visualization is a variable shape based on an amount of sub-components in the given shape. For example, the sub-components 2312 of the analysis-type layer around the model layer 2310, divide the analysis-type layer evenly. In other examples, higher prioritized components may receive a greater share of a layer. Accordingly, because sub-components can expand or contract for the shape and space of the layer, any concentric shape is possible (e.g., in the form of a wedge, or three quarters of a circle, and a polygon).

Figure 23B:
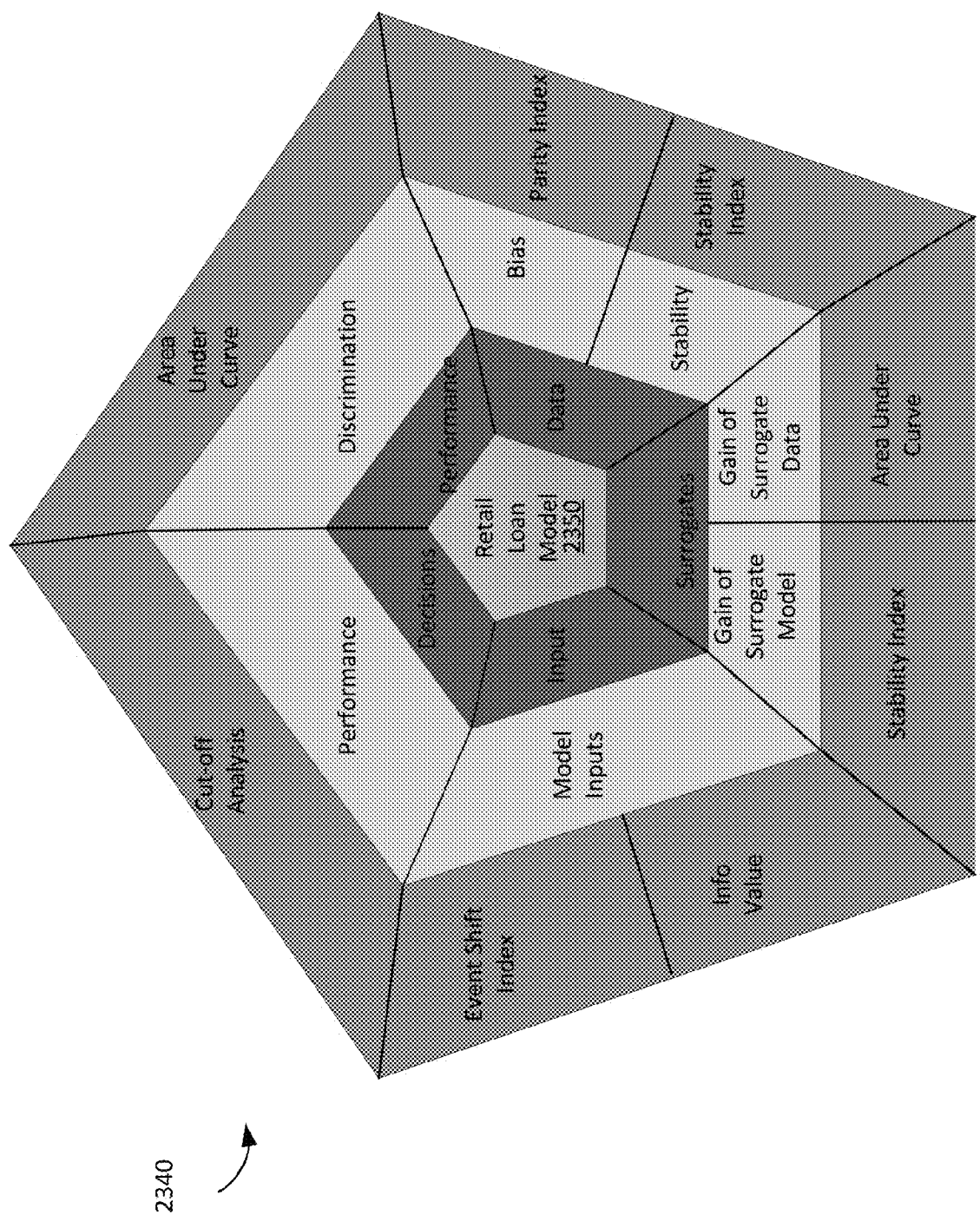
Figure 23C:
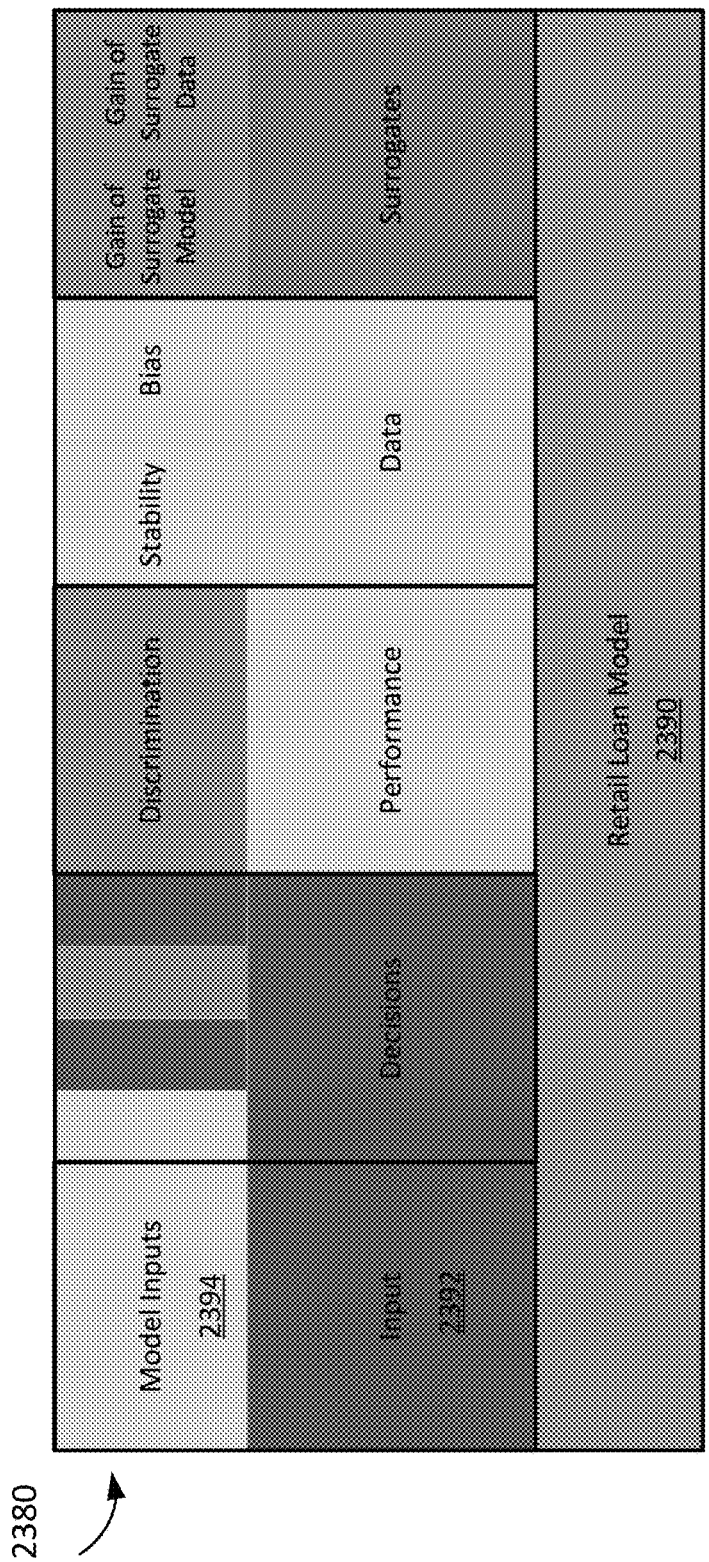

FIG. 23B shows an example of a visualization 2340 where the concentric shapes are pentagons. In embodiments where the central shape is a polygon, the central shape could adopt a variable polygon based on the number of components of the layer around the central shape. For instance, in FIG. 23B, the central shape 2350 representing a monitored model is a pentagon because the first layer around the pentagon has five analysis types. If the user had selected six analysis types, the central shape 2350 could have been a hexagon. A default or user-configured minimum or maximum could be set to preserve a range for the number of sides of the central shape (e.g., for aesthetic purposes). Components can fill-in around the central shape as, for instance, with the wheel designed discussed with respect to FIGS. 16A-16D and the semicircle design discussed with respect to FIG. 23A.

In one or more embodiments, a visualization does not have concentric shapes. For instance, in FIG. 23C components are stacked on top of one another to show a hierarchy relationship. A central shape 2390 representing the monitored system is shown on the bottom. In this example, there are five analysis types monitored for that monitored system (e.g., input 2392). Model inputs 2394 is a measure category stacked on top of input 2392 to show its relationship in a hierarchy to input 2392.

It is also possible to show more or fewer levels in a visualization. For instance, individual measures are not displayed as a box in the example in FIG. 23C. Instead, the overall color of the measurement category component (e.g., model inputs 2394 is yellow) can represent individual measurements. Additionally, individual measurements could be displayed if the user explored a measurement category component (e.g., by clicking on a component to make it a central shape or hovering over it). Accordingly, hierarchy relationships can be represented implicitly by the visualization.

Figure 23D:
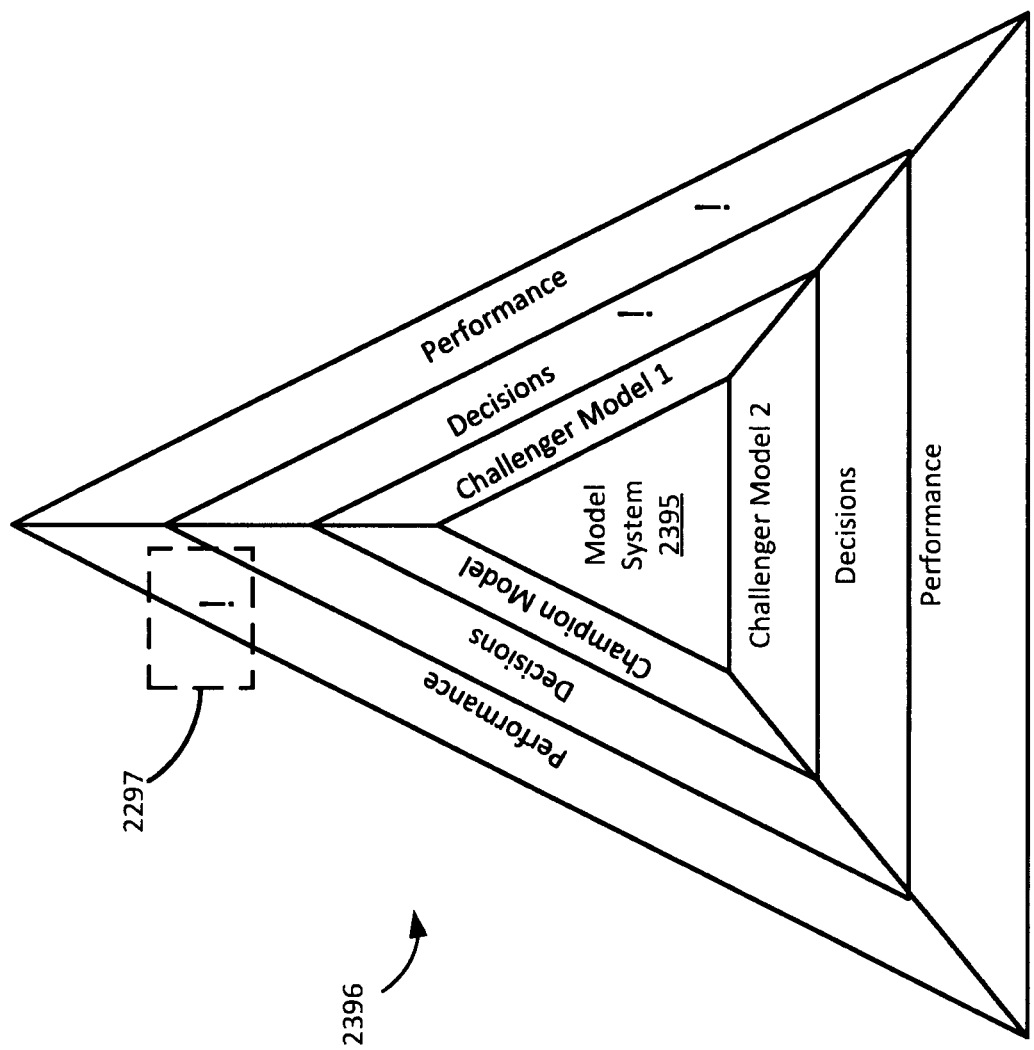

As another example of a model with more or fewer levels, FIG. 23D shows an example of a visualization 2396 for monitoring a model system. The central object 2395 in FIG. 23D is a model system. The first level in this example has individual models in blocks surrounding the central object 2395 (e.g., champion model, challenger model 1, and challenger model 2). Individual layers pertaining to each of those models can continue out as in other examples. For instance, visualization 2396 includes an analysis type layer related to analyzing decisions and a measure category layer relating to measuring performance. For simplicity of explanation, only one component is displayed per layer, but multiple components could be displayed as described with respect to other examples. Instead of using color to convey information, this visualization 2396 uses symbols (e.g., an "!" symbol 2297 displayed in a block for an area needing user caution or intervention). This can help inform a user quickly whether they should switch away from a champion model or intervene to improve the champion model (e.g., if challenger models have more "!" symbols).

One of ordinary skill in the art will appreciate other designs than shown herein. For instance, visualizations in FIGS. 23A-23D were shown with green, yellow, and red to represent model health or symbols, but one of ordinary skill in the art could appreciate other patterns, different colors, or different symbols to represent more or different degrees of model health.

FIGS. 24A-24D illustrate example graphical user interfaces for configuring a visualization. In this example, the rules were created for monitoring model health, but different visualization rules could be applied in other examples.

FIG. 24A shows an example graphical user interface 2400 of variables that can be used for building a computer expression for control of the visualization display. For example, "Of Measure Category" column 2402 shows example variables for referencing measurement types (such as measurements that would provide a percentage, a count, a measure category, and a value). For example, measurement options 2408 allow a user to specify percentage of measurements that should display as red, amber or green. As another example, measurement options 2410 allow a user to specify a measure category for particular values of measurement. Health rules can be applied for each level of a visualization. For instance, "Of Analysis Type" column 2404 and "Of Analysis Object" column 2406 also provide options for referencing particular analysis types and objects, respectively (such as percentages, counts, and categories).

Figure 24B:
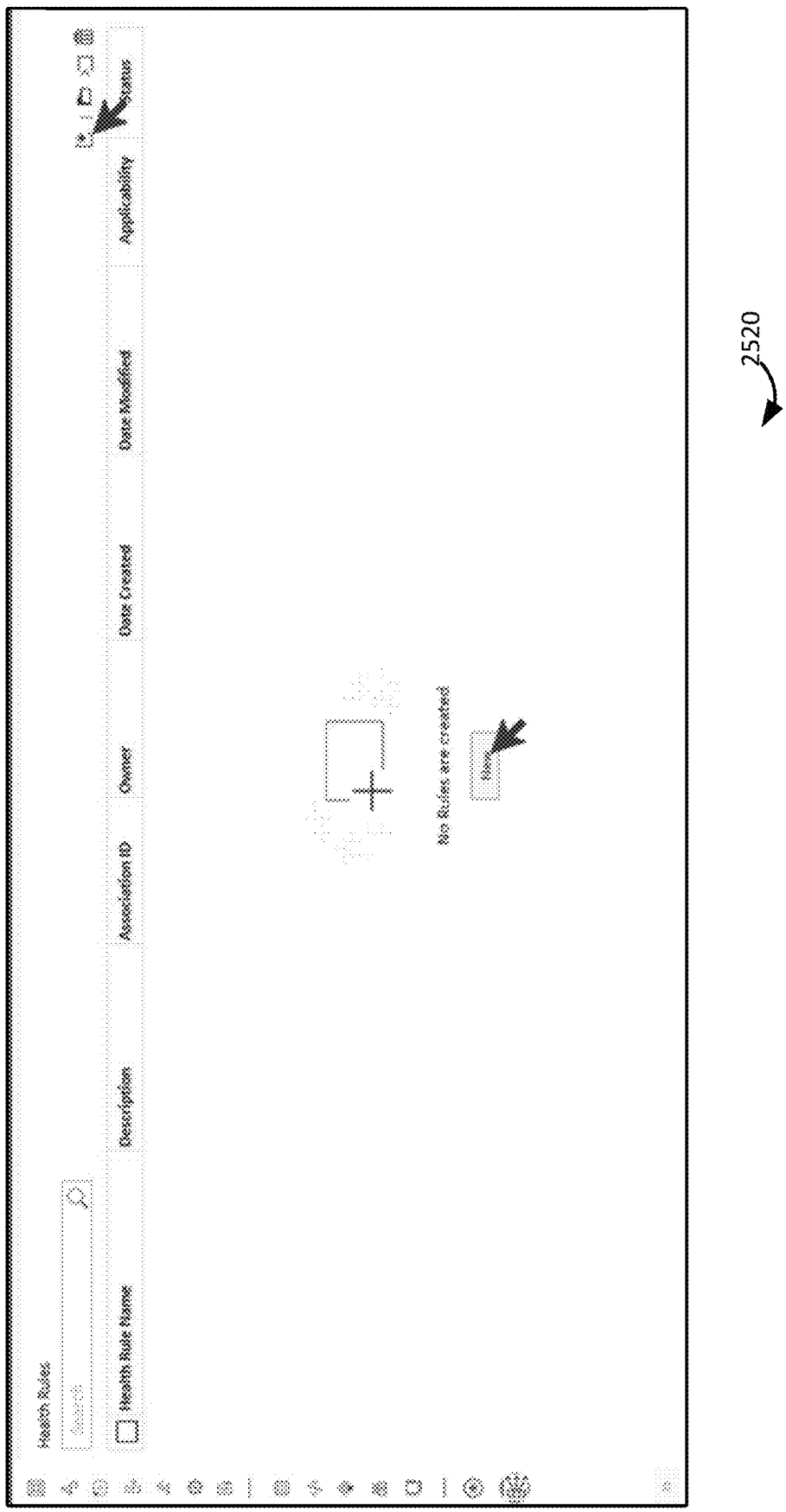

FIG. 24B shows an example graphical user interface 2420 for a user to define particular health rules.

Figure 24C:
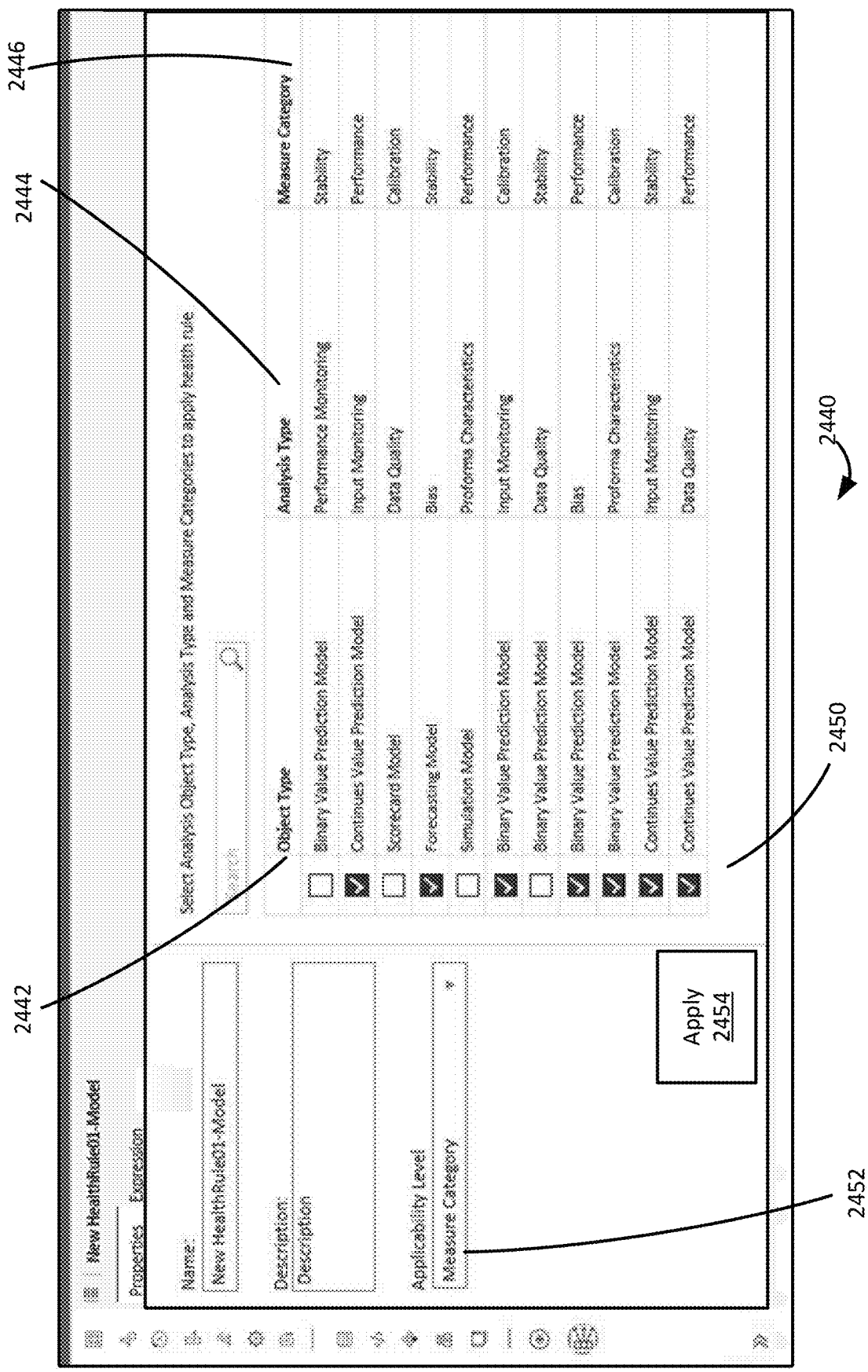
Figure 24D:
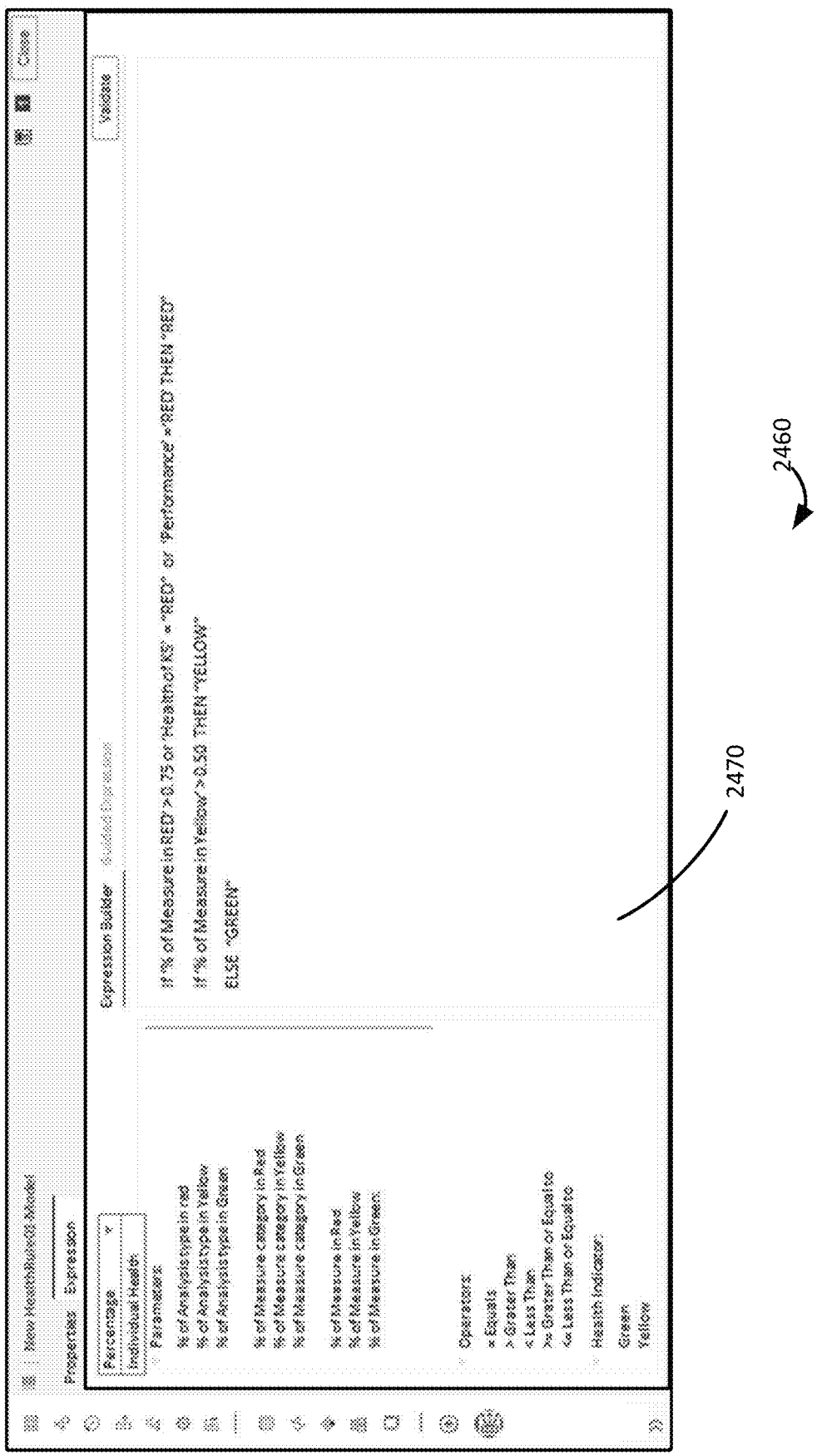

In one or more embodiments, a computing system receives a user indication to select a preconfigured hierarchy with a set of associations comprising: an association between one or more measures and one or more measurement categories, and an association between one or more measurement categories and one or more analysis types. For example, FIG. 24C shows forming a visualization by selecting particular models (displayed in object type column 2442) with particular analysis types (displayed in analysis type column 2444) and measure categories (displayed in measure category column 2446) to set health rules for the visualization. In this example, the user can associate the selected preconfigured hierarchy with one or more user selected models, or associating the selected preconfigured hierarchy with one or more user selected systems of models (e.g., by selecting multiple object types).

FIG. 24C shows an example of a graphical user interface 2440 in which the user has added a new health rule model. In this example, the properties tab 2450 allows the user to specify what associated aspects of a hierarchy are associated with a particular health rule model by selecting a row indicating an item from object type column 2442, analysis type column 2444, and measure category column 2446. As shown in this example, several items can be associated with a health rule, and the user can use an applicability level control 2452 to specify which rules are relevant to associated levels. In this example, the user has selected the applicability level of "measure category" to make the rule relevant to visualizations for items in the measure category column 2446. The user can select the apply control 2454 to apply the new rules to a visualization.

FIG. 24D illustrates the graphical user interface 2460 showing the expression tab 2470, which indicates the rules for displaying the visualization. In this example, the user has indicated that this rule is relevant to measurement percentages and will display particular colors (red, yellow or green) when the measurement percentages are in certain ranges. The user can edit this expressions tab to control the visualizations. One of ordinary skill in the art will appreciate other tools for controlling rules associated with displaying a visualization.

Embodiments herein provided improved tools for monitoring model health. One of ordinary skill in the art will appreciate that the tools described herein could be apply to monitoring other systems.

What is claimed is:

1. A computer-program product tangibly embodied in a non-transitory machine-readable storage medium, the computer-program product including system instructions operable to cause a computing system to:

establish a hierarchy for monitoring one or more trained models, wherein the hierarchy comprises:
  a hierarchical relationship between each of multiple measures of a measure level of the hierarchy and one or more intermediate levels of the hierarchy, wherein an intermediate level of the one or more intermediate levels of the hierarchy comprises one or more of:
    a measurement category defining a category of measurements to which a measure of a measure level of the hierarchy belongs; and
    an analysis type defining a type of analysis to be applied to the measure of the measure level of the hierarchy; and
  a hierarchical relationship between the one or more intermediate levels and at least one trained model of the one or more trained models;
monitor the one or more trained models by generating health measurements, wherein each of the health measurements corresponds to one of the multiple measures, and wherein each of the health measurements indicates a performance of a monitored model of the one or more trained models according to a measurement category or an analysis type that is hierarchically related to the respective measure of the multiple measures;
generate a visualization in a graphical user interface, wherein the visualization comprises a graphical representation of:
  an indication of a health measurement for each of one or more measures of the multiple measures; and
  a hierarchical relationship between each of the one or more measures of the multiple measures, the measure level of the hierarchy, the intermediate level, and the at least one trained model; and
update the visualization responsive to an updated measurement for a measurement in the visualization.

2. The computer-program product of claim 1,
wherein options for each level of the hierarchy are associated with multiple image codes;
wherein the image codes comprise computer instructions for displaying one or more of a color, icon, and pattern in the visualization in a position associated with a respective option of the options for each level of the hierarchy; and
wherein at least one image code indicates a root problem associated in the hierarchy with the at least one trained model for further investigation.

3. The computer-program product of claim 1, wherein the system instructions are operable to cause the computing system to:
  receive a computer rule set associating one of multiple image codes with a respective measurement threshold of multiple measurement thresholds for each of the multiple measures;
  monitor the one or more trained models by determining the updated measurement has crossed a measurement threshold of the multiple measurement thresholds; and
  update the visualization by changing an image according to the updated measurement and the computer rule set.

4. The computer-program product of claim 1,
wherein the system instructions are operable to cause the computing system to generate the visualization by representing the hierarchy with concentric shapes;
wherein each shape of the concentric shapes represents a single level of multiple levels of the hierarchy; and
wherein an outer level of the visualization represents the multiple measures in the hierarchy.

5. The computer-program product of claim 4,
wherein each of one or more shapes of the concentric shapes comprises one or more sub-components in the visualization according to the hierarchy; and
wherein each sub-component of a given shape of the concentric shapes in the visualization is a variable shape based on an amount of sub-components in the given shape.

6. The computer-program product of claim 4,
wherein the system instructions are operable to cause the computing system to generate the visualization by providing a wheel design;
wherein each of the concentric shapes of the wheel design has a circular edge;
wherein the outer level comprises a respective spoke for each of the multiple measures;
wherein the visualization represents a respective health measurement of the health measurements by depicting an image within the respective spoke representing a respective measure within the outer level of the wheel design; and
wherein the visualization represents the hierarchical relationships with the respective measure in the hierarchy by presenting associated options of layers in radial proximity with the respective spoke.

7. The computer-program product of claim 4,
wherein the visualization is interactive;
wherein the system instructions are operable to cause the computing system to:
  receive a user selection of a selected option in a level; and
  update the visualization such that the selected option is a center shape in the concentric shapes of the visualization, and more components than in the previous visualization are displayed that are hierarchically related with the selected option.

8. The computer-program product of claim 1,
wherein the visualization is interactive;
wherein the system instructions are operable to cause the computing system to:
  receive a user selection of an option in a level in the visualization; and
  update the visualization to display only components associated with the option in the hierarchy.

9. The computer-program product of claim 1,
wherein the health measurements are for assessing multiple trained models; and
wherein the system instructions are operable to cause the computing system to:
  generate the visualization by generating one or more visualizations representing a subset of the multiple trained models;
  monitor the multiple trained models by determining the updated measurement has crossed a measurement threshold associated with a measure of the hierarchy; and
  responsive to determining the updated measurement has crossed the measurement threshold, generate a recommendation for an alternative subset of the multiple trained models.

10. The computer-program product of claim 1, wherein the hierarchy comprises:
  the hierarchical relationship between each of the multiple measures and each of multiple measurement categories, wherein a given measure of the multiple measures is associated with only one of the multiple measurement categories;

the hierarchical relationship between each of the multiple measurement categories and each of multiple analysis types, wherein a given measurement category of the multiple measurement categories is associated with only one of the multiple analysis types; and the hierarchical relationship between each of the multiple analysis types and the at least one trained model.

11. The computer-program product of claim 10, wherein each of the analysis types:

comprises a distinct dimension for monitoring the one or more trained models, and forms a distinct hierarchy structure in the visualization.

12. The computer-program product of claim 10, wherein the analysis types comprise input monitoring, data monitoring, decision monitoring, and performance monitoring.

13. The computer-program product of claim 1, wherein the system instructions are operable to cause the computing system to establish the hierarchy by:

receiving a user indication to select a preconfigured hierarchy with a set of hierarchical relationships comprising:

the hierarchical relationship between each of the multiple measures and one or more measurement categories, and the hierarchical relationship between each of the one or more measurement categories and one or more analysis types of the one or more intermediate levels; and associating the selected preconfigured hierarchy with one or more user selected models, or associating the selected preconfigured hierarchy with one or more user selected systems of models.

14. The computer-program product of claim 1, wherein the system instructions are operable to cause the computing system to:

establish the hierarchy by receiving a user configuration to hierarchically relate:

each of the multiple measures with a given one of the one or more intermediate levels of the hierarchy; and each of the one of the intermediate levels of the hierarchy with the at least one trained model of the one or more trained models;

generate the visualization by generating the visualization of a user-configured hierarchy according to the user configuration;

receive a user indication to change a hierarchical relationship in the user-configured hierarchy or add a hierarchical relationship in the user-configured hierarchy;

establish an updated hierarchy according to the user indication; and update the visualization responsive to updated measurements according to the updated hierarchy.

15. The computer-program product of claim 1, wherein the system instructions are operable to cause the computing system to:

monitor the one or more trained models by generating a respective measurement for each of the multiple measures; and generate the visualization by displaying prioritized measures that are a subset of the multiple measures.

16. The computer-program product of claim 1, wherein the one or more trained models comprise one or more dynamic computer models that are updated over time; and wherein the system instructions are operable to cause the computing system to monitor the one or more trained models by generating the health measurements that indicate one or more health statuses or health objectives for the one or more dynamic computer models.

17. The computer-program product of claim 1, wherein the system instructions are operable to cause the computing system to:

receive a user-configured schedule for generating, autonomously, a respective measurement for each of the multiple measures;

generate a plurality of updated measurements according to the user-configured schedule; and generate an indication of a risk category for the one or more trained models according to one or more of the plurality of updated measurements.

18. A computer-implemented method comprising:

establishing a hierarchy for monitoring one or more trained models, wherein the hierarchy comprises:

a hierarchical relationship between each of multiple measures of a measure level of the hierarchy and one or more intermediate levels of the hierarchy, wherein an intermediate level of the one or more intermediate levels of the hierarchy comprises one or more of:

a measurement category defining a category of measurements to which a measure of a measure level of the hierarchy belongs; and an analysis type defining a type of analysis to be applied to the measure of the measure level of the hierarchy; and a hierarchical relationship between the one or more intermediate levels and at least one trained model of the one or more trained models;

monitoring the one or more trained models by generating health measurements, wherein each of the health measurements corresponds to one of the multiple measures, and wherein each of the health measurements indicates a performance of a monitored model of the one or more trained models according to a measurement category or an analysis type that is hierarchically related to the respective measure of the multiple measures;

generating a visualization in a graphical user interface, wherein the visualization comprises:

an indication of a generated health measurement for each of one or more measures of the multiple measures; and a hierarchical relationship between each of the one or more measures of the multiple measures, the measure level of the hierarchy, the intermediate level, and the at least one trained model; and updating the visualization responsive to an updated measurement for a measurement in the visualization.

19. The computer-implemented method of claim 18, wherein options for each level of the hierarchy are associated with multiple image codes;

wherein the image codes comprise computer instructions for displaying one or more of a color, icon, and pattern in the visualization in a position associated with a respective option of the options for each level of the hierarchy; and wherein at least one image code indicates a root problem associated in the hierarchy with the at least one trained model for further investigation.

20. The computer-implemented method of claim 18, wherein the monitoring the one or more trained models comprises determining the updated measurement has crossed a measurement threshold of multiple measurement thresholds; and wherein the method further comprises:
receiving a computer rule set associating one of multiple image codes with a respective measurement threshold of multiple measurement thresholds for each of the multiple measures; and
updating the visualization by changing an image according to the updated measurement and the computer rule set.

21. The computer-implemented method of claim 18, wherein the generating the visualization comprises generating the visualization to represent the hierarchy with concentric shapes;
wherein each shape of the concentric shapes represents a single level of multiple levels of the hierarchy; and
wherein an outer level of the visualization represents the multiple measures in the hierarchy.

22. The computer-implemented method of claim 21, wherein each of one or more shapes of the concentric shapes comprises one or more sub-components in the visualization according to the hierarchy; and
wherein each sub-component of a given shape of the concentric shapes in the visualization is a variable shape based on an amount of sub-components in the given shape.

23. The computer-implemented method of claim 21, wherein the generating the visualization comprises generating the visualization to provide a wheel design;
wherein each of the concentric shapes of the wheel design has a circular edge;
wherein the outer level comprises a respective spoke for each of the multiple measures;
wherein the visualization represents a respective health measurement of the health measurements by depicting an image within the respective spoke representing a respective measure within the outer level of the wheel design; and
wherein the visualization represents the hierarchical relationships with the respective measure in the hierarchy by presenting associated options of layers in radial proximity with the respective spoke.

24. The computer-implemented method of claim 18, wherein the visualization is interactive; and
wherein the computer-implemented method comprises:
receiving a user selection of an option in a level in the visualization; and
updating the visualization to display only components that are hierarchically related with the option.

25. The computer-implemented method of claim 18, wherein the health measurements are for assessing multiple models;
wherein the generating the visualization comprises generating one or more visualizations representing a subset of the multiple models; and
wherein the computer-implemented method comprises:
determining the updated measurement has crossed a measurement threshold associated with a measure of the hierarchy; and
responsive to determining the updated measurement has crossed the measurement threshold, generating a recommendation for an alternative subset of the multiple models.

26. The computer-implemented method of claim 18, wherein the hierarchy comprises:
the hierarchical relationship between each of the multiple measures and each of multiple measurement categories, wherein a given measure of the multiple measures is associated with only one of the multiple measurement categories;
the hierarchical relationship between each of the multiple measurement categories and each of multiple analysis types, wherein a given measurement category of the multiple measurement categories is associated with only one of the multiple analysis types; and
the hierarchical relationship between each of the multiple analysis types and the at least one trained model.

27. The computer-implemented method of claim 18, wherein the establishing the hierarchy comprises:
receiving a user indication to select a preconfigured hierarchy with a set of hierarchical relationships comprising:
the hierarchical relationship between each of the multiple measures and one or more measurement categories, and
the hierarchical relationship between each of the one or more measurement categories and one or more analysis types of the one or more intermediate levels; and
associating the selected preconfigured hierarchy with one or more user selected models, or associating the selected preconfigured hierarchy with one or more user selected systems of models.

28. The computer-implemented method of claim 18, wherein the establishing the hierarchy comprises receiving a user configuration to hierarchically relate:
each of the multiple measures with a given one of the one or more intermediate levels of the hierarchy; and
each of the one of the intermediate levels of the hierarchy with the at least one trained model of the one or more trained models;
wherein the generating the visualization comprises generating a user-configured hierarchy according to the user configuration; and
wherein the computer-implemented method comprises:
receiving a user indication to change a hierarchical relationship in the user-configured hierarchy or add a hierarchical relationship in the user-configured hierarchy;
establishing an updated hierarchy according to the user indication; and
updating the visualization responsive to updated measurements according to the updated hierarchy.

29. The computer-implemented method of claim 18, wherein the monitoring the one or more trained models comprises generating a respective measurement for each of the multiple measures; and
wherein the generating the visualization comprises displaying prioritized measures that are a subset of the multiple measures.

30. A computing device comprising processor and memory, the memory containing instructions executable by the processor wherein the computing device is configured to:
establish a hierarchy for monitoring one or more trained models, wherein the hierarchy comprises:
a hierarchical relationship between each of multiple measures of a measure level of the hierarchy and one or more intermediate levels of the hierarchy, wherein an intermediate level of the one or more intermediate levels of the hierarchy comprises one or more of:
a measurement category defining a category of measurements to which a measure of a measure level of the hierarchy belongs; and an analysis type defining a type of analysis to be applied to the measure of the measure level of the hierarchy; and a hierarchical relationship between the one or more intermediate levels and at least one trained model of the one or more trained models;

monitor the one or more trained models by generating health measurements, wherein each of the health measurements corresponds to one of the multiple measures, and wherein each of the health measurements indicates a performance of a monitored model of the one or more trained models according to a measurement category or an analysis type that is hierarchically related to the respective measure of the multiple measures;

generate a visualization in a graphical user interface, wherein the visualization comprises:

an indication of a generated health measurement for each of one or more measures of the multiple measures; and a hierarchical relationship between each of the one or more measures of the multiple measures; and update the visualization responsive to an updated measurement for a measurement in the visualization.

* * * * *

UNITED STATES PATENT AND TRADEMARK OFFICE
CERTIFICATE OF CORRECTION

PATENT NO. : 11,651,535 B2
APPLICATION NO. : 17/860501
DATED : May 16, 2023
INVENTOR(S) : Terisa Roberts, Vipul Manoj Katiyar and Amol Kishor Malani It is certified that error appears in the above-identified patent and that said Letters Patent is hereby corrected as shown below:

In the Specification

Column 1, Line 15, delete "20214052608", and insert --202216039073--, therefor.

Column 33, Line 17, delete "overtime", and insert --over time--, therefor.

Column 33, Line 19, delete "overtime", and insert --over time--, therefor.

Column 33, Line 42, delete "overtime", and insert --over time--, therefor.

Column 36, Line 17, delete "apart of", and insert --a part of--, therefor.

Column 43, Lines 38-39, delete "(e.g., champion model, challenger model 1, and challenger model 2).", and insert --(e.g., a combination of champion models, and challenger models).--, therefor.

Signed and Sealed this
Twenty-sixth Day of November, 2024

Katherine Kelly Vidal
*Director of the United States Patent and Trademark Office*